United States Patent
Kim et al.

(10) Patent No.: US 11,180,573 B2
(45) Date of Patent: Nov. 23, 2021

(54) EXTRACELLULAR MATRIX-PRODUCING COMPOSITION USING MAST4 GENE AND PREPARATION METHOD THEREFOR

(71) Applicants: Seong Jin Kim, Seoul (KR); Saerom Kim, Seoul (KR); Yeung Won June Kim, Seoul (KR); Ypsse Kim, Seoul (KR)

(72) Inventors: Seong Jin Kim, Seoul (KR); Han Sung Jung, Seoul (KR); Satoru Takahashi, Ibaraki (JP)

(73) Assignees: Jin Kim Seong, Seoul (KR); Saerom Kim, Seoul (KR); Yeung Won June Kim, Seoul (KR); Ypsse Kim, Seoul (KR)

( * ) Notice: Subject to any disclaimer, the term of this patent is extended or adjusted under 35 U.S.C. 154(b) by 0 days.

(21) Appl. No.: 16/492,477

(22) PCT Filed: Mar. 8, 2018

(86) PCT No.: PCT/KR2018/002763
§ 371 (c)(1),
(2) Date: Sep. 9, 2019

(87) PCT Pub. No.: WO2018/164507
PCT Pub. Date: Sep. 13, 2018

(65) Prior Publication Data
US 2020/0239596 A1   Jul. 30, 2020

(30) Foreign Application Priority Data

Mar. 8, 2017 (KR) .................. 10-2017-0029607
Mar. 7, 2018 (KR) .................. 10-2018-0027111

(51) Int. Cl.
| C12N 15/11 | (2006.01) |
| C07K 16/40 | (2006.01) |
| A61K 38/18 | (2006.01) |
| C12N 9/22 | (2006.01) |
| C12N 15/113 | (2010.01) |

(52) U.S. Cl.
CPC .......... C07K 16/40 (2013.01); A61K 38/1841 (2013.01); C12N 9/22 (2013.01); C12N 15/1137 (2013.01); C12N 2310/20 (2017.05); C12N 2800/80 (2013.01)

(58) Field of Classification Search
CPC ...... C07K 16/40; C12N 9/22; C12N 15/1137; C12N 2310/20; C12N 2800/80; C12N 9/12; C12N 2310/14; C12Y 207/11001; A01K 2217/075
See application file for complete search history.

(56) References Cited

U.S. PATENT DOCUMENTS

| 9,254,311 B2 | 2/2016 | Bancel et al. |
| 2009/0176304 A1 | 7/2009 | Smith |
| 2014/0031412 A1* | 1/2014 | Vadolas ............... A61K 48/005 514/44 A |
| 2014/0243392 A1* | 8/2014 | Ochiya .................. A61B 6/032 514/44 A |
| 2014/0341887 A1 | 11/2014 | Dennis, Jr. et al. |
| 2016/0220699 A1 | 8/2016 | O'Heeron |

FOREIGN PATENT DOCUMENTS

| CN | 105636614 | 6/2016 |
| KR | 10-2014-0033284 A | 3/2014 |
| WO | WO 2008/026928 A2 | 3/2008 |
| WO | 2016-201370 A1 | 12/2016 |

OTHER PUBLICATIONS

Funari et al., "Cartilage-selective genes identified in genome-scale analysis of non-cartilage and cartilage gene expression", BioMed Central, BMC Genomics 2007, 8:165, 13 pages.
International Search Report and English translation for International Application No. PCT/KR2018/002763, dated Mar. 8, 2017, 8 pages.
Written Opinion and English translation for International Application No. PCT/KR2018/002763, dated Dec. 18, 2019, 19 pages.
GenBank: AOK98352.1 (Sep. 6, 2016).
Pittenger, M. F. et al. Multilineage potential of adult human mesenchymal stem cells. *Science* (New York, N. Y.) 284, 143-147 (1999).
Chen, Q. et al. Fate decision of mesenchymal stem cells: adipocytes or osteoblasts? *Cell Death and Differ*. 23, 1128-1139, doi:10.1038/cdd.2015.168 (2016).
Bell, D. M. et al. Sox9 directly regulates the type-II collagen gene. *Nature Genetics*. 16, 174-178, doi:10.1038/ng 0697-174 (1997).
Lefebvre, V. et al. Sox9 is a potent activator of the chondrocyte-specific enhancer of the proα1(II) collagen gene. *Molecular and Cellular Biology*. 17, 2336-2346, doi:10.1128/mcb.4.2336 (1997).
Bi, W. et al. Sox9 is required for cartilage formation. *Nature Genetics*. 22, 85-89, doi:10.1038/8792 (1999).
Sekiya, I. et al. Sox9 enhances aggrecan gene promoter/enhancer activity and is up-regulated by retinoic acid in a cartilage-derived cell line, TC6. *The Journal of Biological Chemistry*. 275, 10738-10744, doi:10.1074/jbc.275.15.10738 (2000).
Liu, C.-J. et al. Transcriptional activation of cartilage oligomeric matrix protein by Sox9, Sox5, and Sox6 transcription factors and CBP/p300 coactivators. *Frontiers in Bioscience: a journal and virtual library* 12, 3899-3910 (2007).

(Continued)

*Primary Examiner* — Ekaterina Poliakova-Georgantas
(74) *Attorney, Agent, or Firm* — FisherBroyles, LLP

(57) ABSTRACT

The present invention relates to a composition for producing an extracellular matrix from a eukaryotic cell, the composition comprising a polypeptide or compound capable of specifically binding to a microtubule associated serine/threonine kinase family member 4 (MAST4) protein or a fragment thereof or a polynucleotide, polypeptide or compound capable of specifically binding to a nucleic acid coding for the MAST4 protein or a fragment thereof, and a composition for promoting chondrogenesis, comprising the same composition.

21 Claims, 10 Drawing Sheets
Specification includes a Sequence Listing.

(56) References Cited

OTHER PUBLICATIONS

Lefebvre, V. et al. Sox9 and the many facets of its regulation in the chondrocyte lineage. *Connect Tissue Res.* 58, 2-14. doi:10.1080/03008207.2016.1183667 (2017).
Chikuda, H. et al. Cyclic GMP-dependent protein kinase II is a molecular switch from proliferation to hypertrophic differentiation of chondrocytes. *Genes & Development* 18, 2418-2429, doi:10.1101/gad.1224204 (2004).
Huang, W. et al. The chondrogenic transcription factor Sox9 is a target of signaling by the parathyroid hormone-related peptide in the growth plate of endochondral bones. *Proceeding of the National Academy of Sciences of the United States of America* 98, 160-165, doi:10.1073/pnas.011393998 (2001).
Haudenschild, D. R. et al. Rho Kinase-Dependent Sox9 Activation in Chondrocytes. *Arthritis Rheum.* 62, 191-200. doi:10.1002/art.25051 (2010).
Joyce, M, E. et al. Transforming Growth Factor-☐ and the Initiation of Chondrogenesis and Osteogenesis in the Rat Femur. J Cell Biol. 110, 2195-2207 doi:10.1083/jcb.110.6.2195 (1990).
Kawakami, Y. et al. The role of TGF-βs and Sox9 during limb chondrogenesis. *Curr Opin Cell Biol.* 18, 723-729, doi: 10.1016/j.ceb.2006.10.007 (2006).
Coricor, G. et al. TGF-β regulates phosphorylation and stabilization of Sox9 protein in chondrocytes through p38 and Smad dependent mechanisms. *Sci Rep.* 8, 38616. doi: 10.1038/srep38616 (2016).
Chavez, R. D. et al. Sox9 protein is stabilized by TGF-β and regulates PAPSS2 mRNA expression in chondrocytes Osteoarthritis Cartilage. 25, 332-340. doi:10.1016/j.joca.2016.10.007 (2017).
Furumatsu, T. et al. Smad3 induces chondrogenesis through the activation of Sox9 via CREB-binding protein/p300 recruitment. *J Biol Chem.* 280, 8343-8350. doi: 10.1074/jbc.M413913200 (2005).
Denker, A. E. et al. Chondrogenic differentiation of murine C3H10T1/2 multipotential mesenchymal cells: I. Stimulation by bone morphogenetic protein-2 in high-density micromass cultures. *Differentiation.* 64, 67-76. doi: 10.1046/j.1432-0436.1999.6420067.x (1999).
Stickens, D. et al. Altered endochondral bone development in matrix metalloproteinase 13-deficient mice. *Development.* 131, 5883-5895. doi:10.1242/dev.01461 (2004).
Siegel, P. M. et al. Cytostatic and apoptotic actions of TGF-beta in homeostasis and cancer. *Nat Rev Cancer.* 3, 807-821. doi: 10.1038/nrc1208 (2003).
Wu, M. et al. TGF-β and BMP signaling in osteoblast, skeletal development, and bone formation, homeostasis and disease. Bone Research 4, 16009; doi:10.1038/boneres.2016.9 (2016).
Matsunobu, T. et al. Critical roles of the TGF-β type I receptor ALK5 in perichondrial formation and function, cartilage integrity, and osteoblast differentiation during growth plate development. *Dev Biol.* 332, 325-338. doi:10.1016/j.ydbio.2009.06.002 (2009).
Yang, X. et al. TGF-β/Smad3 signals repress chondrocyte hypertrophic differentiation and are required for maintaining articular cartilage. J Cell Biol 153, 35-46. doi:10.1083/jcb.153.1.35 (2001).
Massagué, J. et al. Smad transcription factors. *Genes Dev.* 19, 2783-2810. doi:10.1101/gad.1350705 (2005).
Kang, J. S. et al. Repression of Runx2 function by TGF-beta through recruitment of class II histone deacetylases by Smad3. *EMBO J.* 24, 2543-2555. doi: 10.1038/sj.emboj.7600729 (2005).
Chen, C.-R. et al. E2F4/5 and p107 as Smad cofactors linking the TGF-β receptor to c-myc repression. *Cell* 110, 19-32. doi: 10.1016/s0092-8674(02)00801-2 (2002).
Minoo, P. et al. Smad3 prevents binding of NKX2.1 and FOXA1 to the SpB promoter through its MH1 and MH2 domains. *Nucleic Acids Res.* 36, 179-188. doi: 10.1093/nar/gkm871 (2008).

Deribe, Y. L. et al. Post-translational modifications in signal integration. *Nat Struct Mol Biol.* 17, 666-672. doi: 10.1038/nsmb.1842 (2010).
Hong, X. et al. Sox9 is targeted for proteasomal degradation by the E3 ligase FBW7 in response to DNA damage. *Nucleic Acids Research,* 44, 8855-8869 doi: 10.1093/nar/gkw748 (2016).
Akiyama, H. et al. The transcription factor Sox9 has essential roles in successive steps of the chondrocyte differentiation pathway and is required for expression of Sox5 and Sox6. *Genes Dev.* 16, 2813-2828. doi: 10.1101/gad.1017802 (2002).
Hattori, T. et al. E6-AP/UBE3A Protein Acts as a Ubiquitin Ligase toward Sox9 Protein. *J Biol Chem.* 288, 35138-35148. doi: 10.1074/jbc.M113.486795 (2013).
Pearce, L. R. et al. The nuts and bolts of AGC protein kinases. *Nat Rev Mol Cell Biol.* 11, 9-22. doi: 10.1038/nrm2822 (2010).
Clay, M. R. et al. MAST2 and NOTCH1 translocations in breast carcinoma and associated pre-invasive lesions. *Hum Pathol.* 44, 2837-2844. doi: 10.1016/j.humpath.2013.08.001 (2013).
Valiente, M. et al. Binding of PTEN to Specific PDZ Domains Contributes to PTEN Protein Stability and Phosphorylation by Microtubule-associated Serine/Threonine Kinases. *J Biol Chem.* 280, 28936-28943. doi: 10.1074/jbc.M504761200 (2005).
Hibar, D. P. et al. Novel genetic loci associated with hippocampal volume. *Nat Commun.* 8, 13624. doi: 10.1038/ncomms13624 (2017).
EPICURE Consortium, et al. Genome-wide association analysis of genetic generalized epilepsies implicates susceptibility loci at 1q43, 2p16.1, 2q22.3 and 17q21.32. *Human Molecular Genetics,* 21, 5359-5372. doi:10.1093/hmg/dds373 (2012).
Simone, R. D. et al. Senile myoclonic epilepsy: Delineation of a common condition associated with Alzheimer's disease in Down syndrome. *Seizure.* 19, 383-389. doi: 10.1016/j.seizure. 2010.04.008 (2010).
Nagel, A. K. et al. Identification of O-Linked N-Acetylglucosamine (O-GlcNAc)-modified Osteoblast Proteins by Electron Transfer Dissociation Tandem Mass Spectrometry Reveals Proteins Critical for Bone Formation. *Mol Cell Proteomics.* 12, 945-955. doi: 10.1074/mcp.M112.026633 (2013).
Meka, S. R. K. et al. Role of Microtubules in Osteogenic Differentiation of Mesenchymal Stem Cells on 3D Nanofibrous Scaffolds. *ACS Biomater. Sci. Eng,* 3, 551-559. DOI: 10.1021/acsbiomaterials.6b00725 (2017).
Cong, L. et al. Multiplex Genome Engineering Using CRISPR/Cas Systems. *Science.* 339, 819-823. doi:10.1126/science.1231143 (2013).
Kim, D. et al. TopHat2: accurate alignment of transcriptomes in the presence of insertions, deletions and gene fusions. *Genome Biol.* 14, R36. doi: 10.1186/gb-2013-14-4-r36 (2013).
Trapnell, C. et al. Transcript assembly and abundance estimation from RNA-Seq reveals thousands of new transcripts and switching among isoforms. *Nat Biotechnol.* 28, 511-515. doi:10.1038/nbt.1621 (2010).
Huang, D. W. et al. Systematic and integrative analysis of large gene lists using DAVID bioinformatics resources. *Nat Protoc.* 4, 44-57. doi: 10.1038/nprot.2008.211 (2009).
Jensen, L. J. et al. STRING 8—a global view on proteins and their functional interactions in 630 organisms. *Nucleic Acids Research* 37, D412-D416. doi:10.1093/nar/gkn760 (2009).
Extended European Search Report for corresponding European Application No. 18764604.7, dated Dec. 22, 2020, 8 pages.
Garland et al., "Expression of the MAST family of serine/threonine kinases", Brain Research, Elsevier, Amsterdam, NL., vol. 1195, Dec. 23, 2007, pp. 12-19, XP0224829696, ISSN: 0006-8993, DOI: 10.1016/J.BRAINRES.2007.12.027.

* cited by examiner

FIG. 1
METHOD OF PREPARING CRISPR/Cas9-MAST4 KNOCKOUT MICE
|   | Exon1 | Exon15 |
|---|---|---|
| A | −71bp(FRAMESHIFT) | −3bp |
| B | −90bp | −13bp(FRAMESHIFT) |
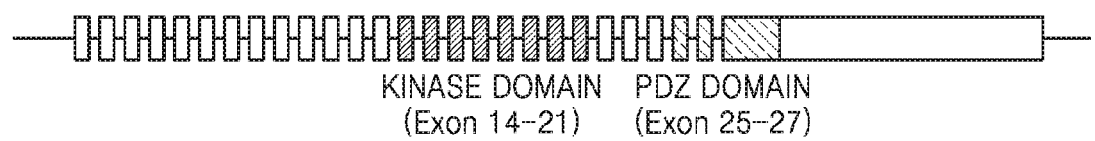
KINASE DOMAIN (Exon 14-21)   PDZ DOMAIN (Exon 25-27)
A TYPE KO
FRAMESHIFT OF EXON 1, TRANSLATION STOPPED IN EXON 1
B TYPE KO
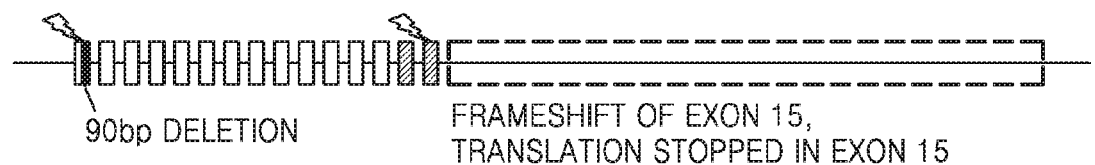
90bp DELETION    FRAMESHIFT OF EXON 15, TRANSLATION STOPPED IN EXON 15

FIG. 7

CR#1 (SEQ ID NO: 79)
Human MAST4 Exon 5

| | |
|---|---|
| ttatcacttgtgtgtatggcatgttacatatttgcactcaagcgctggaagaaggcattt | |
| gattattgctccactggtggtgaggaatattgatggtgttgtgctatatgaatacattat | |
| attttctaatattcaagaggtagccacccctcaaatattagtgaatgcataattgtaata | Intron |
| attttaacaataacatgagcagataggttgctcaacctggtccatgtctaccgggaacat | |
| ggttgaacattattgatgctatattcttttaaactttgttttttctttcttttgatag | |
| TTGCCGAACAAGCAACCGGAAAAGCTTAATAGGCAATGGGCAGTCACCCAGCATTGCCTCG ACCACACTCACCTCTCTCTGCTCATGCAG | Exon 5 |
| gtaattggttaccatttcttgagttttgttttatttctttatttgttggttttttaaaat | |
| aattaatgcattttgatatttggtatgtcttcacatgttatctttgttttcctgctgttt | Intron |
| tatccctaagttgttctttgcgatatgttagcccagatcttatcctctctgtttcagtgt | |
| ttggactctaaaatacagaattccttttatatggggtctcttttaattatttctttct | |

CR#2 (SEQ ID NO: 80)
Human MAST4 Exon 8

| | |
|---|---|
| tccagagagaaaactatcttttgggaaattataaacaaatgaggcaaaatatggaaagca | |
| ttttgaactctgagagagaacatcaagttatacattaggcagtcgttcttataaactta | Intron |
| acatgaaaagaaacaataaaaatggtggtattgtccaagtttaactcatcgatctctcc | |
| tgttcatttgaagagtttctttctgaggtagttatgtgacctcactttggttttttcag | |
| TCATCCTGTTCCTCCCAGGAGAAGTTGCATCAGTTACCATACCAACCAACACCAGACGAG TTACACTTCTTATCAAAACATTTCTGTACCACCGAAAGCATCGCCACTGAGAACAGATGC AGGAACACGCCGATGCGCCCCGTTCCCGAAGTCTGAG | Exon 8 |
| gtgtgtgggcctggctgaaaaccattacttagttggattctctatttcaaacattttga | |
| gtgaacacttcggtcctttaggtcatatgtgtgttaactgacttgcaaactattacaaat | Intron |
| atagtgtgatgtttccatgtacacataatattgttaattaccattgaaaggcatcttata | |
| agtttccttttcagttctcacaatttgctgattgcagcagtagtaatcacgatggtcttg | |

CR#3 (SEQ ID NO: 81)
Human MAST4 Exon 5

| | |
|---|---|
| ttatcacttgtgtgtatggcatgttacatatttgcactcaagcgctggaagaaggcattt | |
| gattattgctccactggtggtgaggaatattgatggtgttgtgctatatgaatacattat | |
| attttctaatattcaagaggtagccacccctcaaatattagtgaatgcataattgtaata | Intron |
| attttaacaataacatgagcagataggttgctcaacctggtccatgtctaccgggaacat | |
| ggttgaacattattgatgctatattcttttaaactttgttttttctttcttttgatag | |
| TTGCCGAACAAGCAACCGGAAAAGCTTAATAGGCAATGGGCAGTCACCAGCATTGCCTCG ACCACACTCACCTCTCTCTGCTCATGCAG | Exon 5 |
| gtaattggttaccatttcttgagttttgttttatttctttatttgttggttttttaaaat | |
| aattaatgcattttgatatttggtatgtcttcacatgttatctttgttttcctgctgttt | Intron |
| tatccctaagttgttctttgcgatatgttagcccagatcttatcctctctgtttcagtgt | |
| ttggactctaaaatacagaattccttttatatggggtctcttttaattatttctttct | | ers or the fragment thereof, or a compound capable of
EXTRACELLULAR MATRIX-PRODUCING COMPOSITION USING MAST4 GENE AND PREPARATION METHOD THEREFOR This application is the U.S. national phase of International Application No. PCT/KR2018/002763 filed 8 Mar. 2018, which designated the U.S. and claims priority to KR Application No. 10-2017-0029607 filed 8 Mar. 2017, and KR Patent Application No. 10-2018-0027111 filed 7 Mar. 2018, the entire contents of each of which are hereby incorporated by reference.

TECHNICAL FIELD

The present disclosure relates to a composition for producing an extracellular matrix from eukaryotic cells using Microtubule Associated Serine/Threonine Kinase Family Member 4 (MAST4) gene, a method of producing the extracellular matrix from the eukaryotic cells, and a composition for promoting chondrogenesis, the composition including the above composition.

BACKGROUND ART

Since most bone formation begins from a cartilaginous template, successful skeletal development requires a perfect cooperation in both structural and molecular aspects. Articular cartilage is a highly organized tissue, and the mechanism of in-vivo chondrogenesis involved therein is still unknown. Interactions between collagen microfibers and other extracellular matrix component proteins are known to maintain the structural integrity of the cartilage, but the signaling mechanisms regulating their complex processes have not yet been clearly revealed. Therefore, identification of the existence and function of a master regulator that leads chondrogenesis is not only academically meaningful, but also contributes to the public health as well as to development of innovative therapeutics.

Microtubule associated serine/threonine kinase (MAST) 4 is known to be expressed in cartilage (*BMC Genomics* 2007, 8: 165), but its role has not been clearly elucidated. CN 105636614 discloses that MAST4 may be used for the treatment of cartilage, but this is based only on the stochastic results of MAST4 expression in the cartilage, and does not elucidate specific roles thereof.

The present inventors have found MAST4 as a novel central regulator that is involved in chondrogenesis, and provide a source technology for the development of substances that modulate the activity of MAST4.

PRIOR ART DOCUMENTS

Non-Patent Document: *BMC Genomics* 2007, 8:165
Patent Document: CN 105636614

DESCRIPTION OF EMBODIMENTS

Technical Problem

An aspect provides a composition for promoting production of an extracellular matrix from eukaryotic cells, the composition including a compound capable of specifically binding to Microtubule Associated Serine/Threonine Kinase Family Member 4 (MAST4) protein or a fragment thereof, or a compound capable of specifically binding to a nucleic acid encoding the MAST4 protein or the fragment thereof.

Another aspect provides a composition for promoting chondrogenesis of chondrocytes, the composition including a compound capable of specifically binding to MAST4 protein or a fragment thereof, or a compound capable of specifically binding to a nucleic acid encoding the MAST4 protein or the fragment thereof.

Still another aspect provides a method of producing an extracellular matrix from eukaryotic cells, the method including contacting the eukaryotic cells with the composition for promoting production of the extracellular matrix from eukaryotic cells.

Solution to Problem

According to an aspect, provided is a composition for promoting production of an extracellular matrix from eukaryotic cells, the composition including a compound capable of specifically binding to Microtubule Associated Serine/Threonine Kinase Family Member 4 (MAST4) protein or a fragment thereof, or a compound capable of specifically binding to a nucleic acid encoding the MAST4 protein or the fragment thereof.

According to another aspect, provided is a composition for promoting chondrogenesis of chondrocytes, the composition including a compound capable of specifically binding to MAST4 protein or a fragment thereof, or a compound capable of specifically binding to a nucleic acid encoding the MAST4 protein or the fragment thereof.

In a specific embodiment, the compound capable of specifically binding to the MAST4 protein or the fragment thereof, or the compound capable of specifically binding to the nucleic acid encoding the MAST4 protein or the fragment thereof includes those capable of at least partially binding to the protein or the fragment thereof, or the nucleic acid. Here, the compound may be a chemically synthesized compound, polypeptide, or polynucleotide, or a combination thereof. These compounds may inhibit activity or expression of MAST4 protein.

In a specific embodiment, the composition for promoting production of extracellular matrix from eukaryotic cells may be a composition for promoting chondrogenesis from eukaryotic cells.

In the composition, the activity inhibitor of MAST4 protein or the expression inhibitor of MAST4 protein includes any one, as long as it is able to inhibit expression of MAST4 gene or activity of MAST4 protein. The activity inhibitor or the expression inhibitor may be a polynucleotide complementary to the entire or a part of the MAST4 gene. The polynucleotide sequence may be RNA, DNA, or a hybrid thereof.

In a specific embodiment, the activity inhibition of the MAST4 protein may be kinase activity inhibition of the MAST4 protein.

MAST4 is a kinase capable of phosphorylating Ser or Thr of a target substrate, and the kinase activity inhibition of the MAST4 protein means blocking of phosphorylation of a target substrate of MAST4, specifically, blocking of phosphorylation of Ser or Thr.

In a specific embodiment, the polypeptide specifically binding to MAST4 protein or the fragment thereof, or the polypeptide specifically binding to the nucleic acid encoding the MAST4 protein or the fragment thereof may be an antibody or an antigen-binding fragment thereof.

The term "antibody" means a specific immunoglobulin directed against an antigenic site. MAST4 gene is cloned into an expression vector to obtain the MAST4 protein encoded by the gene, and the antibody may be prepared from the protein according to a common method in the art. A type of the antibody includes a polyclonal antibody or a monoclonal antibody, and includes all immunoglobulin antibodies. The antibody includes not only complete forms having two full-length light chains and two full-length heavy chains but also functional fragments of antibody molecules which have a specific antigen binding site (binding domain) directed against an antigenic site to retain an antigen-binding function, although they do not have the intact complete antibody structure having two light chains and two heavy chains.

The term "polynucleotide" may be used in the same meaning as a nucleotide or a nucleic acid, unless otherwise mentioned, and refers to a deoxyribonucleotide or a ribonucleotide. The polynucleotide may include an analog of a natural nucleotide and an analog having a modified sugar or base moiety, unless otherwise mentioned. The polynucleotide may be modified by various methods known in the art, as needed. Examples of the modification may include methylation, capping, substitution of a natural nucleotide with one or more homologues, and modification between nucleotides, for example, modification to uncharged linkages (e.g., methylphosphonate, phosphotriester, phosphoroamidate, carbamate, etc.) or charged linkages (e.g., phosphorothioate, phosphorodithioate, etc.).

In a specific embodiment, as the compound capable of specifically binding to the nucleic acid encoding the MAST4 protein or the fragment thereof, the polynucleotide capable of specifically binding to the nucleic acid encoding the MAST4 protein or the fragment thereof may be microRNA (miRNA), small interfering RNA (siRNA), short hairpin RNA (shRNA), Piwi-interacting RNA (piRNA), small nuclear RNA (snRNA), or antisense oligonucleotide, each specific to the nucleic acid encoding the MAST4 protein or the fragment thereof, or a combination thereof.

In another specific embodiment, the compound capable of specifically binding to the nucleic acid encoding the MAST4 protein or the fragment thereof may include the polynucleotide capable of specifically binding to the nucleic acid encoding the MAST4 protein or the fragment thereof, and may be CRISPR-Cas including guide RNA specific to the nucleic acid encoding the MAST4 protein or the fragment thereof.

In a specific embodiment, the Cas may be Cas9.

Clustered Regularly Interspaced Short Palindromic Repeats (CRISPRs) mean loci including many short direct repeats found in the genome of bacteria or archaea, of which genetic sequences are revealed. The CRISPR-Cas system includes Cas9 as an essential protein element which forms a complex with guide RNA (specifically, two RNAs, called CRISPR RNA (crRNA) and trans-activating crRNA (tracrRNA), included in guide RNA), and it serves as an active endonuclease.

In a specific embodiment, for the CRISPR-Cas system to specifically act on the target gene MAST4, the guide RNA may have a form of a dual RNA including CRISPR RNA (crRNA) and transactivating crRNA (tracrRNA) specific to the nucleic acid encoding the MAST4 protein, or a single strand guide RNA including parts of the crRNA and the tracrRNA and hybridizing with the nucleic acid encoding the MAST4 protein. The dual RNA and the single strand guide RNA may at least partially hybridize with the polynucleotide encoding the MAST4 protein, and specifically, may hybridize with a region corresponding to "5'-TACCCTGCCGCTGCCGCACC-3' (SEQ ID NO: 17)" in the polynucleotide sequence encoding the amino acid sequence of MAST4 protein.

Specifically, the guide RNA may be a dual RNA including crRNA and tracrRNA that hybridize with a target sequence selected from the nucleotide sequence encoding the MAST4 protein, or a single strand guide RNA including parts of the crRNA and the tracrRNA and hybridizing with the nucleotide encoding the MAST4 protein. The MAST4 gene which is the target sequence includes a polynucleotide sequence at least partially complementary to the crRNA or sgRNA, and a sequence including a protospacer-adjacent motif (PAM). The PAM may be a sequence well-known in the art, which may have a sequence suitable to be recognized by a nuclease protein. The MAST4 gene targeted by the CRISPR-Cas system may be endogenous DNA or artificial DNA. The nucleotide encoding the MAST4 protein may be specifically endogenous DNA of a eukaryotic cell, and more specifically, endogenous DNA of a chondrocyte.

In a specific embodiment, the crRNA or sgRNA may include twenty consecutive polynucleotides complementary to the target DNA. The target DNA of the complementary twenty consecutive polynucleotides may be 5'-TACCCTGCCGCTGCCGCACC-3' (SEQ ID NO: 17), and may be selected from the sequences marked in bold in SEQ ID NOS: 74, 76, and 77 of Table 6. A nucleic acid encoding the Cas9 protein or the Cas9 protein may be derived from a microorganism of the genus *Streptococcus*. The microorganism of the genus *Streptococcus* may be *Streptococcus pyogenes*. The PAM may mean 5'-NGG-3' trinucledotide, and the Cas9 protein may further include a nuclear localization signal (NLS) at the C-terminus or N-terminus to enhance the efficiency.

In the composition for promoting production of an extracellular matrix from eukaryotic cells of the present disclosure, the eukaryotic cells may be yeast cells, fungal cells, protozoa cells, plant cells, higher plant cells, insect cells, amphibian cells, or mammalian cells. The mammal may vary such as humans, monkeys, cows, horses, pigs, etc. The eukaryotic cells may include cultured cells (in vitro) isolated from an individual, graft cells, in vivo cells, or recombinant cells, but are not limited thereto. The eukaryotic cells isolated from an individual may be eukaryotic cells isolated from an individual the same as an individual into which the product including extracellular matrix produced from the eukaryotic cells is injected. In this case, it is advantageous in that side effects such as unnecessary hyperimmune reactions or rejection reactions including graft-versus-host reaction generated by injecting a product produced from a different individual may be prevented.

In a specific embodiment, the eukaryotic cells may be fibroblasts or chondrocytes.

In a specific embodiment, the composition for promoting the production of extracellular matrix from the eukaryotic cells and/or the composition for promoting chondrogenesis of chondrocytes may further include TGF-β1. The present inventors confirmed that MAST4 expression in human chondrocytes is reduced by TGF-β1, and as a result, production of extracellular matrix is promoted. Therefore, to more effectively and easily promote extracellular matrix in MAST4 knockout cells of eukaryotic cells (or chondrocytes), combination treatment with TGF-β1 may be advantageous.

The MAST4 is a protein derived from a human (*Homo sapiens*) or a mouse (*Musmusculus*), but the same protein may also be expressed in other mammals such as monkeys, cows, horses, etc.

The human-derived MAST4 may include all of seven isoforms present in human cells. The seven isoforms may include amino acid sequences of NP_055998.1 (SEQ ID NO: 1), NP_942123.1 (SEQ ID NO: 2), NP_001158136.1 (SEQ ID NO: 3), NP_001277155.1 (SEQ ID NO: 4), NP_001277156.1 (SEQ ID NO: 5), NP_001277157.1 (SEQ ID NO: 6), or NP_001284580.1 (SEQ ID NO: 7), based on NCBI reference sequence, and a protein or a polypeptide having each of the amino acid sequences may be translated from mRNA including polynucleotide sequences of SEQ ID NOS: 8 to 14 each encoding the amino acid sequences of SEQ ID NOS: 1 to 7 in the sequence of NM_015183.2, NM_198828.2, NM_001164664.1, NM_001290226.1, NM_001290227.1, NM_001290228.1, or NM_001297651.1.

The mouse-derived MAST4 may include an amino acid sequence of NP_780380.2 (SEQ ID NO: 15), based on NCBI reference sequence, and a protein or a polypeptide having the amino acid sequence may be translated from mRNA including a polynucleotide sequence of SEQ ID NO: 16 encoding the amino acid sequence of SEQ ID NO: 15 in the sequence of NM_175171.3.

An amino acid sequence or a polynucleotide sequence having biologically equivalent activity, even though it is not identical to the amino acid sequences of SEQ ID NOS: 1 to 7 and 15 and the polynucleotide sequences of SEQ ID NOs: 8 to 14 and 16, may also be regarded as the MAST4 protein or mRNA thereof.

Therefore, in a specific embodiment, the MAST4 protein may include any one sequence of SEQ ID NOS: 1 to 7 and 15, and the nucleotide sequence encoding the MAST4 protein may include any one sequence of SEQ ID NOS: 8 to 14 and 16.

The MAST4 protein or polypeptide may include an amino acid sequence having 60% or more, for example, 70% or more, 80% or more, 90% or more, 95% or more, 99% or more, or 100% sequence identity to SEQ ID NOS: 1 to 7 and 15. Further, the MAST4 protein may have an amino acid sequence having modification of 1 or more amino acids, 2 or more amino acids, 3 or more amino acids, 4 or more amino acids, 5 or more amino acids, 6 or more amino acids, or 7 or more amino acids in the amino acid sequences of SEQ ID NOS: 1 to 7 and 15.

Each polynucleotide encoding MAST4 may have a sequence having 60% or more, for example, 70% or more, 80% or more, 90% or more, 95% or more, 99% or more, or 100% sequence identity to SEQ ID NOS: 8 to 14 and 16. Further, the polynucleotide encoding MAST4 may be a polynucleotide having a different sequence of 1 or more nucleotides, 2 or more nucleotides, 3 or more nucleotides, 4 or more nucleotides, 5 or more nucleotides, 6 or more nucleotides, or 7 or more nucleotides in the sequences of SEQ ID NOS: 8 to 14 and 16.

The present inventors first demonstrated that production of extracellular matrix is increased and chondrogenesis is promoted by inhibiting MAST4 gene expression in chondrocytes.

Therefore, in a specific embodiment, the composition for promoting production of an extracellular matrix from eukaryotic cells or the composition for promoting chondrogenesis of chondrocytes of the present disclosure may prevent or treat a joint disease, or improve symptoms thereof.

Further, in a specific embodiment, the composition for promoting the production of extracellular matrix from the eukaryotic cells and/or the composition for promoting chondrogenesis of chondrocytes of the present disclosure may be to induce chondrogenesis.

Further, in a specific embodiment, the composition for promoting the production of extracellular matrix from the eukaryotic cells may be used for tissue regeneration or anti-aging.

The tissue regeneration refers to regeneration of the skin damaged or deformed by wounds, burns, injury, aging, chronic inflammation, diseases, genetic factors, etc., and includes all those used for medical or skin cosmetic purposes. The damage or deformation is caused by the loss or reduced production of extracellular matrix in a tissue, or impossibility of recovery of the extracellular matrix in the tissue by the above factors, and the damage or deformation means symptoms improved, alleviated, recovered, or cured by promoting the production of extracellular matrix by the composition of the present disclosure.

As a tissue including the skin ages, the production of extracellular matrix decreases, resulting in reduced elasticity of the tissue, and the tissue is easily deformed or damaged by external stimuli, and its recovery becomes slow. Accordingly, the composition of the present disclosure may promote the production of extracellular matrix, thereby preventing or recovering reduced elasticity, deformation, or damage of tissues caused by aging.

In another specific embodiment, the composition for tissue regeneration or anti-aging may be used as a component of fillers or collagen supplement cosmetics. In still another specific embodiment, the composition for tissue regeneration or anti-aging may be used as a component of functional cosmetics to block the adsorption of fine dust or minerals.

The composition for promoting the production of extracellular matrix from the eukaryotic cells or the composition for promoting chondrogenesis of chondrocytes of the present disclosure may further include a pharmaceutically acceptable salt or carrier.

The term "pharmaceutically acceptable salt" means any organic or inorganic addition salt of the compound in the composition of the present disclosure, whose concentration has effective action because it is relatively non-toxic and harmless to patients and whose side effects do not degrade the beneficial efficacy of the composition of the present disclosure. These salt may be selected from any one known to those skilled in the art.

The composition of the present disclosure may further include a pharmaceutically acceptable carrier. The composition including the pharmaceutically acceptable carrier may have various formulations for oral or parenteral administration. When formulated, the composition may be prepared using commonly used diluents or excipients such as fillers, extenders, binders, wetting agents, disintegrating agents, surfactants, etc. Solid formulations for oral administration may include tablets, pills, powders, granules, capsules, troches, etc., and these solid formulations may be prepared by mixing one or more compounds of the present disclosure with at least one excipient such as starch, calcium carbonate, sucrose, lactose, or gelatin. Moreover, in addition to simple excipients, lubricants such as magnesium stearate, talc, etc. may be used. Liquid formulations for oral administration may include suspensions, liquids for internal use, emulsions, syrups, etc. Various excipients such as wetting agents, sweeteners, flavoring agents, preservatives, etc. may be included, in addition to commonly used simple diluents such as water, liquid paraffin, etc.

Formulations for parenteral administration may include sterilized aqueous solutions, non-aqueous solvents, suspensions, emulsions, freeze-dried preparations, suppositories, etc. The non-aqueous solvents and suspensions may include propylene glycol, polyethylene glycol, vegetable oils such as olive oil, injectable esters such as ethyl oleate, etc. As a base of a suppository, witepsol, macrogol, Tween 61, cocoa butter, laurin butter, glycerol, gelatin, etc. may be used.

An aspect provides a method of preventing, treating, or improving a joint disease, the method including administering the composition to a subject.

Another aspect provides a method of producing an extracellular matrix, the method including contacting eukaryotic cells with the composition for producing the extracellular matrix from eukaryotic cells of the present disclosure.

In a specific embodiment, the eukaryotic cells may be isolated from a subject. In a specific embodiment, the eukaryotic cells may be chondrocytes.

In a specific embodiment, the contacting with the eukaryotic cells may include co-transfecting or serial-transfecting the composition into the eukaryotic cells. To effectively deliver the composition of the present disclosure to the eukaryotic cells, various methods known in the art, such as microinjection, electroporation, DEAE-dextran treatment, lipofection, nanoparticle-mediated transfection, protein transduction domain-mediated transduction, virus-mediated gene delivery, and PEG-mediated transfection in protoplast, etc. may be used, but are not limited thereto.

In a specific embodiment, the contacting with the eukaryotic cells may include culturing the eukaryotic cells in the presence of the composition.

In a specific embodiment, the culturing includes culturing in the presence of a chondrogenic inducer.

In a specific embodiment, the method of producing the extracellular matrix of the present disclosure may further include isolating the extracellular matrix from the contacting product.

In another specific embodiment, the method of producing the extracellular matrix may include contacting chondrocytes with the composition for promoting chondrogenesis of the present disclosure.

Still another aspect provides a method of forming a cartilage, the method including contacting chondrocytes with the composition for promoting chondrogenesis of the present disclosure.

In a specific embodiment, the chondrocytes may be isolated from a subject.

In a specific embodiment, the chondrocytes may be derived from a subject to be transplanted with the produced cartilage.

Still another aspect provides a method of producing ECM, the method including culturing eukaryotic cells having increased extracellular matrix productivity of the present disclosure to produce ECM; and isolating ECM from the culture.

In a specific embodiment, the culturing may be culturing in the presence of a chondrogenic inducer.

In a specific embodiment, the chondrogenic inducer may be BMP.

Advantageous Effects of Disclosure

A composition for promoting production of an extracellular matrix according to an aspect may be injected into a subject who requires supply of the extracellular matrix, thereby preventing or treating diseases including a joint disease, and improving symptoms thereof, and the composition may be applied to a method of efficiently producing the extracellular matrix from eukaryotic cells.

A composition for promoting chondrogenesis of chondrocytes according to another aspect may be injected into a subject, thereby preventing or treating diseases including a joint disease, and improving symptoms thereof. The composition may promote chondrogenesis of chondrocytes isolated from the subject, and thus it may be applied to a method of efficiently producing various components including extracellular matrice which are produced by chondrogenesis.

According to a method of producing an extracellular matrix from eukaryotic cells according to still another aspect, the extracellular matrix may be efficiently produced from eukaryotic cells.

BRIEF DESCRIPTION OF DRAWINGS

FIG. 1 illustrates a method of preparing MAST4 knockout mice using a CRISPR/Cas9 system;

FIG. 7 shows sequence information of target genes used to knockout MAST4 of human cells;

MODE OF DISCLOSURE

Figure 2A:
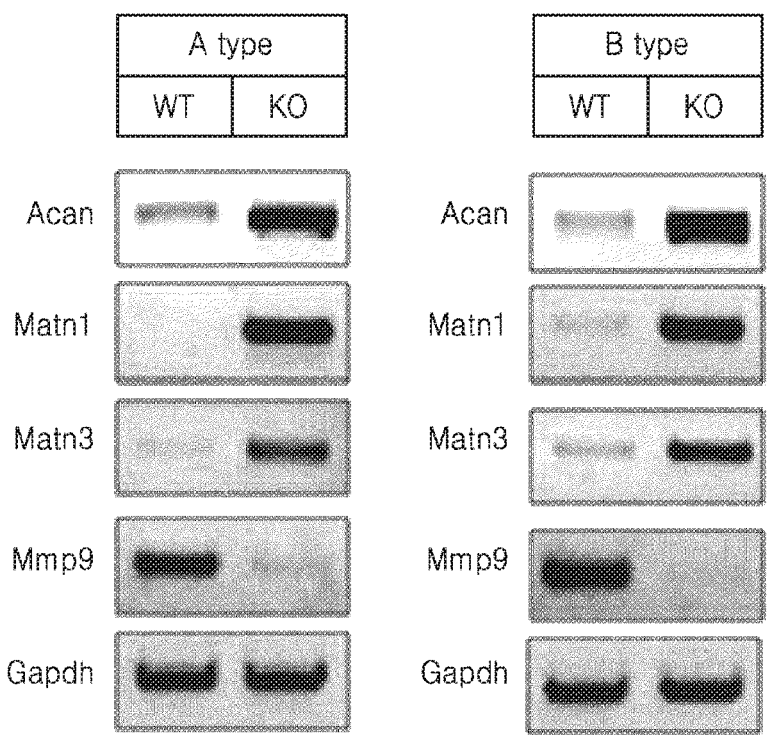
FIG. 2A shows RT-PCR results of examining changes in expression levels of respective genes in MAST4 knockout mouse type A and B.

Hereinafter, the present disclosure will be described in more detail with reference to embodiments. However, these embodiments are for illustrative purposes only, and the scope of the present disclosure is not intended to be limited by these embodiments.

Example 1

Confirmation of Increased Expression of Cartilage Component in MAST4 Knockout Mouse 1-1. Preparation of MAST4 Knockout Mouse Using CRISPR/Cas9 System To examine whether an extracellular matrix as a cartilage component was increased by suppressing MAST4 expression, MAST4 knockout mice were prepared using a CRISPR/Cas9 system.

In detail, to prepare CRISPR knockout mice, pX330-U6-Chimeric_BB-CBh-hSpCas9 (Addgene, #42230), donated by Dr. Feng Zhang (Cong et al., 2013), was used as a plasmid capable of expressing Cas9 mRNA and guide RNA. Since MAST4 is a large protein of 7 kb or more, it was designed such that the gene editing was allowed to target two parts, exon 1 and exon 15. A guide RNA sequence targeting exon 1 of MAST4 is 5'-GGAAACTCTGTCG-GAGGAAGGGG-3' (SEQ ID NO:88) and a sequence targeting exon 15 is 5'-GGCACAAAGAGTCCCGCCAGAGG-3' (SEQ ID NO:89). The guide RNA sequence was used to prepare oligomers as in MAST4 CRISPR oligomers of the following Table in accordance with the manufacturer's protocol (http://crispr.mit.edu/, Zhang Feng Lab), and each oligomer was inserted into a px330 plasmid to clone two plasmids targeting exon 1 and exon 15, respectively.

To obtain embryos, 5 IU of pregnant mare serum gonadotrophin (PMSG; Prospec, cat. No. HOR-272) was administered to a C57BU6J female mouse 2 days before mating, and after 47 hours, 5 IU of humanchorionic gonadotrophin (hCG; Prospec, cat. HOR-250) was administered thereto . . . . Thereafter, the mouse was mated with C57BL/6J male mouse, and embryos were obtained from fallopian tubes. A microinjection mixture including 5 ng/µl of the prepared plasmid and 10 ng of ssDNA donor was injected into the pronuclei of the embryos at a one-cell-stage with reference to an existing standard protocol (Gordon and Ruddle, 1981). The injected one-cell-embryos were transferred to pseudopregnant ICR mice.

Phenotypic analysis of born mice was performed for exon 1 and exon 15. Finally, two types of MAST4 knockout mice were obtained. Information about the two types of MAST4 knockout mice, type A and type B are shown as in FIG. 1 and the following Table 2 (5'→3').

TABLE 2

| | |
|---|---|
| Type A MAST4 KO (71 bp deletion in exon 1) (SEQ ID NO: 22) | ATGGGGGAGAAAGTTTCCGAGGCGCCTGAGCCCGT GCCCCGGGGCTGCAGCGGACACGGCGCCCGGACCC TAGTCTCTTCGGCGGCAGCCGTGTCCTCGGAGGGCG CTTCCTCAGCGGAGTCATCCTCTGGCTCGGAAACTCT GTCGGAGGAAGGGGAGCCCAGCCGCTTCTCCTGCA GGTCGCAGCCGCCGCGGCCGCCGGGCGGCGCCCT GGGAACCCGGCTACCCGCCGCGTGGGCTCCCGCGC GCGTGGCTCTGGAGCGTGGAGTCCCTACCCTGCCG CTGCCGCACCCGGGAGGAGCGGTGCTGCCGGTGCC CCAGGTCAGCAGCGCATCCCAAGAGGAGCAGGATGA AGAG |
| Type B MAST4 KO (90 bp deletion in exon 1) (SEQ ID NO: 23) | ATGGGGGAGAAAGTTTCCGAGGCGCCTGAGCCCGT GCCCCGGGGCTGCAGCGGACACGGCGCCCGGACCC TAGTCTCTTCGGCGGCAGCCGTGTCCTCGGAGGGCG CTTCCTCAGCGGAGTCATCCTCTGGCTCGGAAACTCT GTCGGAGGAAGGGGAGCCCAGCCGCTTCTCCTGCA GGTCGCAGCCGCCGCGGCCGCCGGGCGGCGCCCT GGGAACCCGGCTACCCGCCGCGTGGGCTCCCGCGC GCGTGGCTCTGGAGCGTGGAGTCCCTACCCTGCCG CTGCCGCACCCGGGAGGAGCGGTGCTGCCGGTGCC CCAGGTCAGCAGCGCATCCCAAGAGGAGCAGGATGA AGAG |
| type A MAST4 KO (3 bp deletion in exon 15) (SEQ ID NO: 24) | GGCAGTCTACTTTGTTCGGCACAAAGAGTCCCGCCA GAGGTTTGCCATGAAGAAGATCAA CAAGCAGAACCTCATCCTTCGGAACCAGATCCAGCA GGCCTTCGTGGAGCGAGACATCCT GACTTTCGCAGAGAACCCCTTTGTGGTCAGCATGTAT TGCTCCTTTGAAACGAGGCGTCA CTTATGCATGGTCATGGAGTATGTAGAAG |
| type B MAST4 KO (13 bp deletion in exon 15) (SEQ ID NO: 25) | GGCAGTCTACTTTGTTCGGCACAAAGAGTCCCGCCA GAGGTTTGCCATGAAGAAGATCAA CAAGCAGAACCTCATCCTTCGGAACCAGATCCAGCA GGCCTTCGTGGAGCGAGACATCCT GACTTTCGCAGAGAACCCCTTTGTGGTCAGCATGTAT TGCTCCTTTGAAACGAGGCGTCA CTTATGCATGGTCATGGAGTATGTAGAAG |

Bases to be deleted in Table 2 are shown in bold.

1-2. RNA-Sequencing for Confirmation of Change of Cartilage Component Expression in MAST4 Knockout Mouse To examine changes in the extracellular matrix as a cartilage component in MAST4 knockout mice prepared in Example 1-1, RNA-sequencing was performed for respective genes.

In detail, 1 day-old-MAST4 knockout mice prepared in Example 1-1, hetero-type mice, and wild-type mice were sacrificed, and then their tibia was excised. Each of the excised tibias was placed in a dish containing DEPC-PBS on

TABLE 1

| | |
|---|---|
| MAST4 exon 1 CRISPR F (SEQ ID NO: 18) | 5'-caccGGAAACTCTGTCGGAGGAA G-3' |
| MAST4 exon 1 CRISPR R (SEQ ID NO: 19) | 5'-aaacCTTCCTCCGACAGAGTTTC C-3' |
| MAST4 exon 15 CRISPR F (SEQ ID NO: 20) | 5'-caccGGCACAAAGAGTCCCGCCA G-3' |
| MAST4 exon 15 CRISPR R (SEQ ID NO: 21) | 5'-aaacCTGGCGGGACTCTTTGTGC C-3' | ice, and cartilage and bone in the tibia were separated using a needle under a dissecting microscope. The tissues separated from each group was immersed in 500 μl of TRIzol (purchased from Invitrogen), which were then used as samples. RNA was extracted according to a method well known in the art, and quantified using a nanodrop (Thermo scientific).

RNA-sequencing was performed by Theragen Etex. In detail, mRNA was isolated from 2 μg of total RNA extracted from the mouse of each group using oligo(dT). After fragmentation of the mRNA, single-stranded cDNA was synthesized through random hexamer priming. This single-strand cDNA was used as a template to synthesize a second strand, thereby synthesizing a double-stranded cDNA. To prepare blunt-ends, end repair was performed, and to ligate an adapter, A-tailing and adapter ligation were performed. Thereafter, cDNA library was amplified by polymerase chain reaction (PCR). A concentration and size of the final product were examined using 2100 BioAnalyzer. The produced library was finally quantified using a KAPA library quantification kit, and then sequence interpretation was performed using Hiseq2500. To remove low-quality sequences from the interpreted sequences, filtering was performed such that reads containing 10% or more of bases marked as 'N's in the sequence information or reads containing 40% or more of bases less than Q20 were removed, and reads whose average quality is Q20 or less were also removed. The whole filtering process was performed using the in-house program. The filtered sequences were aligned to a reference genome sequence (hg19) of the corresponding species using STAR v2.4.0b (Dobin et al, 2013).

Expression level was measured using Cufflinks v2.1.1 (Trapnell C. et al, 2010), and the calculated expression values were expressed as fragments read per kilobase of exon per million fragments mapped (FPKM). Ensemble 72 was used as a genetic information database, and a non-coding gene region was removed with expression-mask option. To increase measurement accuracy of the expression levels, multi-read-correction and frag-bias-correct options were additionally used, and all other options were set to default values.

To examine genes which were changed by MAST4 knockout, expression values of the samples of each group, which were obtained through Cufflinks, were used. Genes, of which expression values were twice or more, as compared with those of wild-type MAST4, and which had a significance of P value <0.01, were selected, and the expression values of the selected genes and their differences are listed in Table 3.

As a result, it was confirmed that expression of many genes associated with extracellular matrix as a cartilage component was increased as in the following Table 3. However, in all of the two types of MAST4 knockout mice, reduced expression of mmp8 and mmp9 which are extracellular matrix-degrading enzymes was observed.

TABLE 3

|  |  |  | Fold induction in A KO | Fold induction in B KO |
| --- | --- | --- | --- | --- |
| ENSMUSG00000030607 | Acan | aggrecan [Source:MGI Symbol;Acc:MGI:99602] | 4.65 | 5.79 |
| ENSMUSG00000031375 | Bgn | biglycan [Source:MGI Symbol;Acc:MGI:88158] | 2.38 | 2.26 |
| ENSMUSG00000039084 | Chad | chondroadherin [Source:MGI Symbol;Acc:MGI:1096866] | 5.90 | 7.79 |
| ENSMUSG00000042254 | Cilp | cartilage intermediate layer protein, nucleotide pyrophosphohydrolase [Source:MGI Symbol;Acc:MGI:2444507] | 2.41 | 1.79 |
| ENSMUSG00000022483 | Col2a1 | collagen, type II, alpha 1 [Source:MGI Symbol;Acc:MGI:88452] | 4.13 | 17.41 |
| ENSMUSG00000026043 | Col3a1 | collagen, type III, alpha 1 [Source:MGI Symbol;Acc:MGI:88453] | 1.47 | 1.18 |
| ENSMUSG00000031502 | Col4a1 | collagen, type IV, alpha 1[Source:MGI Symbol;Acc:MGI:88454] | 1.57 | 1.51 |
| ENSMUSG00000031503 | Col4a2 | collagen, type IV, alpha 2 [Source:MGI Symbol;Acc:MGI:88455] | 1.57 | 1.27 |
| ENSMUSG00000067158 | Col4a4 | collagen, type IV, alpha 4 [Source:MGI Symbol;Acc:MGI:104687] | 1.26 | 7.41 |
| ENSMUSG00000031274 | Col4a5 | collagen, type IV, alpha 5 [Source:MGI Symbol;Acc:MGI:88456] | 1.33 | 1.23 |
| ENSMUSG00000031273 | Col4a6 | collagen, type IV, alpha 6 [Source:MGI Symbol;Acc:MGI:2152695] | 2.90 | 3.33 |
| ENSMUSG00000026837 | Col5a1 | collagen, type V, alpha 1 [Source:MGI Symbol;Acc:MGI:88457] | 1.11 | 1.44 |
| ENSMUSG00000026042 | Col5a2 | collagen, type V, alpha 2 [Source:MGI Symbol;Acc:MGI:88458] | 1.17 | 1.37 |
| ENSMUSG00000001119 | Col6a1 | collagen, type VI, alpha 1 [Source:MGI Symbol;Acc:MGI:88459] | 2.04 | 1.96 |
| ENSMUSG00000020241 | Col6a2 | collagen, type VI, alpha 2 [Source:MGI Symbol;Acc:MGI:88460] | 1.75 | 1.89 |
| ENSMUSG00000048126 | Col6a3 | collagen, type VI, alpha 3 [Source:MGI Symbol;Acc:MGI:88461] | 2.28 | 2.20 |
| ENSMUSG00000056174 | Col8a2 | collagen, type VIII, alpha 2 [Source:MGI Symbol;Acc:MGI:88464] | 1.44 | 2.33 |
| ENSMUSG00000026147 | Col9a1 | collagen, type IX, alpha 1 [Source:MGI Symbol;Acc:MGI:88465] | 4.47 | 12.86 |
| ENSMUSG00000028626 | Col9a2 | collagen, type IX, alpha 2 [Source:MGI Symbol;Acc:MGI:88466] | 2.38 | 14.16 |
| ENSMUSG00000027570 | Col9a3 | collagen, type IX, alpha 3 [Source:MGI Symbol;Acc:MGI:894686] | 2.81 | 17.87 |
| ENSMUSG00000027966 | Col11a1 | collagen, type XI, alpha 1 [Source:MGI Symbol;Acc:MGI:88446] | 2.44 | 3.10 |
| ENSMUSG00000024330 | Col11a2 | collagen, type XI, alpha 2 [Source:MGI Symbol;Acc:MGI:88447] | 2.06 | 7.45 |
| ENSMUSG00000032332 | Col12a1 | collagen, type XII, alpha 1 [Source:MGI Symbol;Acc:MGI:88448] | 1.93 | 1.72 |
| ENSMUSG00000022371 | Col14a1 | collagen, type XIV, alpha 1 [Source:MGI Symbol;Acc:MGI:1341272] | 1.83 | 1.60 |
| ENSMUSG00000028339 | Col15a1 | collagen, type XV, alpha 1 [Source:MGI Symbol;Acc:MGI:88449] | 2.16 | 2.54 |
| ENSMUSG00000040690 | Col16a1 | collagen, type XVI, alpha 1 [Source:MGI Symbol;Acc:MGI:1095396] | 1.73 | 1.66 |
| ENSMUSG00000028197 | Col24a1 | collagen, type XXIV, alpha 1 [Source:MGI Symbol;Acc:MGI:1918605] | 1.48 | 1.65 |
| ENSMUSG00000045672 | Col27a1 | collagen, type XXVII, alpha 1 [Source:MGI Symbol;Acc:MGI:2672118] | 1.83 | 2.37 |
| ENSMUSG00000031849 | Comp | cartilage oligomeric matrix protein [Source:MGI Symbol;Acc:MGI:88469] | 3.86 | 6.56 |
| ENSMUSG00000006369 | Fbln1 | fibulin 1 [Source:MGI Symbol;Acc:MGI:95487] | 1.54 | 1.15 |
| ENSMUSG00000027386 | Fbln7 | fibulin 7 [Source:MGI Symbol;Acc:MGI:1917620] | 2.90 | 5.36 |
| ENSMUSG00000041559 | Fmod | fibromodulin [Source:MGI Symbol;Acc:MGI:1328364] | 4.03 | 4.15 |
| ENSMUSG00000026193 | Fn1 | fibronectin 1 [Source:MGI Symbol;Acc:MGI:95566] | 1.62 | 1.34 |
| ENSMUSG00000021613 | Hapln1 | hyaluronan and proteoglycan link protein 1 [Source:MGI Symbol;Acc:MGI:1337006] | 1.71 | 6.49 |
| ENSMUSG00000030606 | Hapln3 | hyaluronan and proteoglycan link protein 3 [Source:MGI Symbol;Acc:MGI:1914916] | 2.87 | 7.01 |
| ENSMUSG00000022025 | Lect1 | leukocyte cell derived chemotaxin 1 [Source:MGI Symbol;Acc:MGI:1341171] | 3.90 | 14.35 |
| ENSMUSG00000040533 | Matn1 | matrilin 1, cartilage matrix protein [Source:MGI Symbol;Acc:MGI:106591] | 11.31 | 19.74 |
| ENSMUSG00000020583 | Matn3 | matrilin 3 [Source:MGI Symbol;Acc:MGI:1328350] | 4.54 | 16.44 |
| ENSMUSG00000016995 | Matn4 | matrilin 4 [Source:MGI Symbol;Acc:MGI:1328314] | 2.61 | 5.29 |

TABLE 3-continued

| | | | Fold induction in A KO | Fold induction in B KO |
|---|---|---|---|---|
| ENSMUSG00000041577 | Prelp | proline arginine-rich end leucine-rich repeat [Source:MGI Symbol;Acc:MGI:2151110] | 2.32 | 2.66 |
| ENSMUSG00000017009 | Sdc4 | syndecan 4 [Source:MGI Symbol;Acc:MGI:1349164] | 1.63 | 2.09 |
| ENSMUSG00000086596 | Susd5 | sushi domain containing 5 [Source:MGI Symbol;Acc:MGI:2685972] | 3.90 | 8.99 |
| ENSMUSG00000026668 | Ucma | upper zone of growth plate and cartilage matrix associated [Source:MGI Symbol;Acc:MGI:1915777] | 6.85 | 21.57 |
| ENSMUSG00000005800 | Mmp8 | matrix metallopeptidase 8 [Source:MGI Symbol;Acc:MGI:1202395] | 0.44 | 0.11 |
| ENSMUSG00000017737 | Mmp9 | matrix metallopeptidase 9 [Source:MGI Symbol;Acc:MGI:97011] | 0.08 | 0.34 |

1-3. RT-PCR for Confirmation of Change of Cartilage Component Expression in MAST4 Knockout Mouse To more specifically examine changes in the extracellular matrix as a cartilage component in MAST4 knockout mice prepared in Example 1-1, a part of genes showing changes in the expression in the RNA sequencing results of Example 1-2 was selected and subjected to RT-PCR.

In detail, RT-PCR was performed using a set of primers of the following Table 4 and AccuPower PCR premix (BIONEER, Korea) according to the manufacturer's instructions.

TABLE 4

| Name | Type | | Sequence (5'→3') | Product size |
|---|---|---|---|---|
| Acan | Forward | (서열번호 26) | GGTCACTGTTACCGCCACTT | 430 |
| | Reverse | (서열번호 27) | CCAGGGAGCTGATCTCGTAG | |
| Chad | Forward | (서열번호 28) | GCCAAGGACCTGCGCTGGCT | 500 |
| | Reverse | (서열번호 29) | GCTTTCTTGGACCTCTTGGT | |
| Col2a1 | Forward | (서열번호 30) | GCCAAGACCTGAAACTCTGC | 494 |
| | Reverse | (서열번호 31) | CTTGCCCCACTTACCAGTGT | |
| Col9a1 | Forward | (서열번호 32) | CGTGGATTTCCAGGCCGTGG | 500 |
| | Reverse | (서열번호 33) | TCGCTGTCCTTGATCACCAG | |
| Col11a1 | Forward | (서열번호 34) | GCTAGGTGTTCCTGGTCTGC | 429 |
| | Reverse | (서열번호 35) | CCACTTTCTCCAGCTGTTCC | |
| Comp | Forward | (서열번호 36) | AACGGCTCGCACTGCACCGA | 400 |
| | Reverse | (서열번호 37) | CCCGTTGCCGGCCCAGCCAA | |
| Fmod | Forward | (서열번호 38) | CCAGCAGTCCACCTACTACG | 350 |
| | Reverse | (서열번호 39) | TGCCTCAGCTTGGAGAAGAC | |
| Lect1 | Forward | (서열번호 40) | GTTTTGCTGGAGGAGAGAAG | 520 |
| | Reverse | (서열번호 41) | CAGTGGGTGTAGCTCCGCCT | |
| Matn1 | Forward | (서열번호 42) | GGCAAGACCTGCAATGTCTG | 400 |
| | Reverse | (서열번호 43) | TAGTCCTGGCTCCGGCCATC | |
| Matn3 | Forward | (서열번호 44) | CAGGACCAGGTGAATGAGGT | 550 |
| | Reverse | (서열번호 45) | ATCTGCATTCAGAGTGTAGC | |
| Matn4 | Forward | (서열번호 46) | AGCTCCCGCAGCGTGCGCCC | 350 |
| | Reverse | (서열번호 47) | ATGCCGCGGGCGCGCGCCTG | |
| Susd5 | Forward | (서열번호 48) | TCTCAGAATGGCTCTCAGGG | 440 |
| | Reverse | (서열번호 49) | TACCACTCCCCACAGCTGTT | |
| Ucma | Forward | (서열번호 50) | GGTCAACAGCTCCAGGAAAG | 151 |
| | Reverse | (서열번호 51) | TTTCTGGTGGCTAAGCAAGG | |
| Mmp8 | Forward | (서열번호 52) | TGATGGACCCAATGGAATCC | 300 |
| | Reverse | (서열번호 53) | GGGGTCACACGCTTTGGGTG | |
| Mmp9 | Forward | (서열번호 54) | GACGGGTATCCCTTCGACGG | 422 |
| | Reverse | (서열번호 55) | GTGGTGGCGCACCAGCGGTA | |
| Gapdh | Forward | (서열번호 56) | TGGCAAAGTGGAGATTGTTGCC | 156 |
| | Reverse | (서열번호 57) | AAGATGGTGATGGGCTTCCCG | |
| Hapln1 | Forward | (서열번호 58) | GGGCTGGACTGGTGCAATGC | 280 |
| | Reverse | (서열번호 59) | GCAAATATCTGGCCCACTTT | |

TABLE 4-continued

| Name | Type | | Sequence (5'→3') | Product size |
|---|---|---|---|---|
| Hapln3 | Forward | (서열번호 60) | TCCTTTGGGGACTACCAAGG | 460 |
| | Reverse | (서열번호 61) | CACCCGCCCCTTGAGGGCAG | |
| Prelp | Forward | (서열번호 62) | GCCCACAACATCCTGAGAAA | 440 |
| | Reverse | (서열번호 63) | AAGCACATCATGAGGTCCAG | |
| Fbln7 | Forward | (서열번호 64) | ACTGGGAACCGCTGTCAGCA | 320 |
| | Reverse | (서열번호 65) | ACATCCTCACAGCTCTTCCC | |
| Sdc4 | Forward | (서열번호 66) | AGGTCATCGACCCCCAGGAC | 520 |
| | Reverse | (서열번호 67) | AACTCATTGGTGGGGCTTT | |
| Bgn | Forward | (서열번호 68) | AAGATCTCCAAGATCCATGA | 270 |
| | Reverse | (서열번호 69) | GCCTCTGAGATGCGCAGGTA | |

Figure 2B:
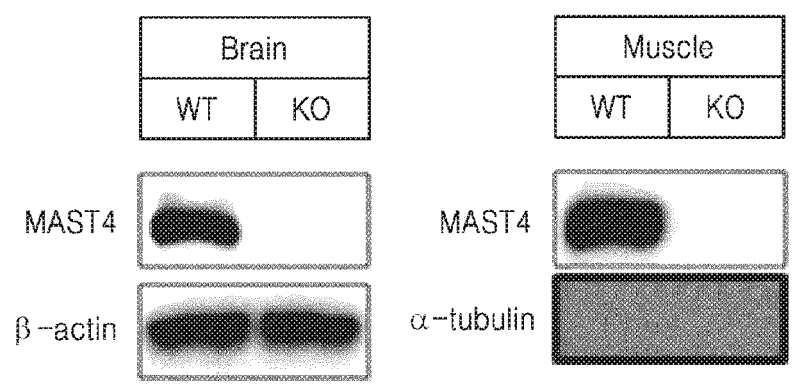
FIG. 2B shows protein expression patterns in MAST4 knockout mice.
Figure 3:
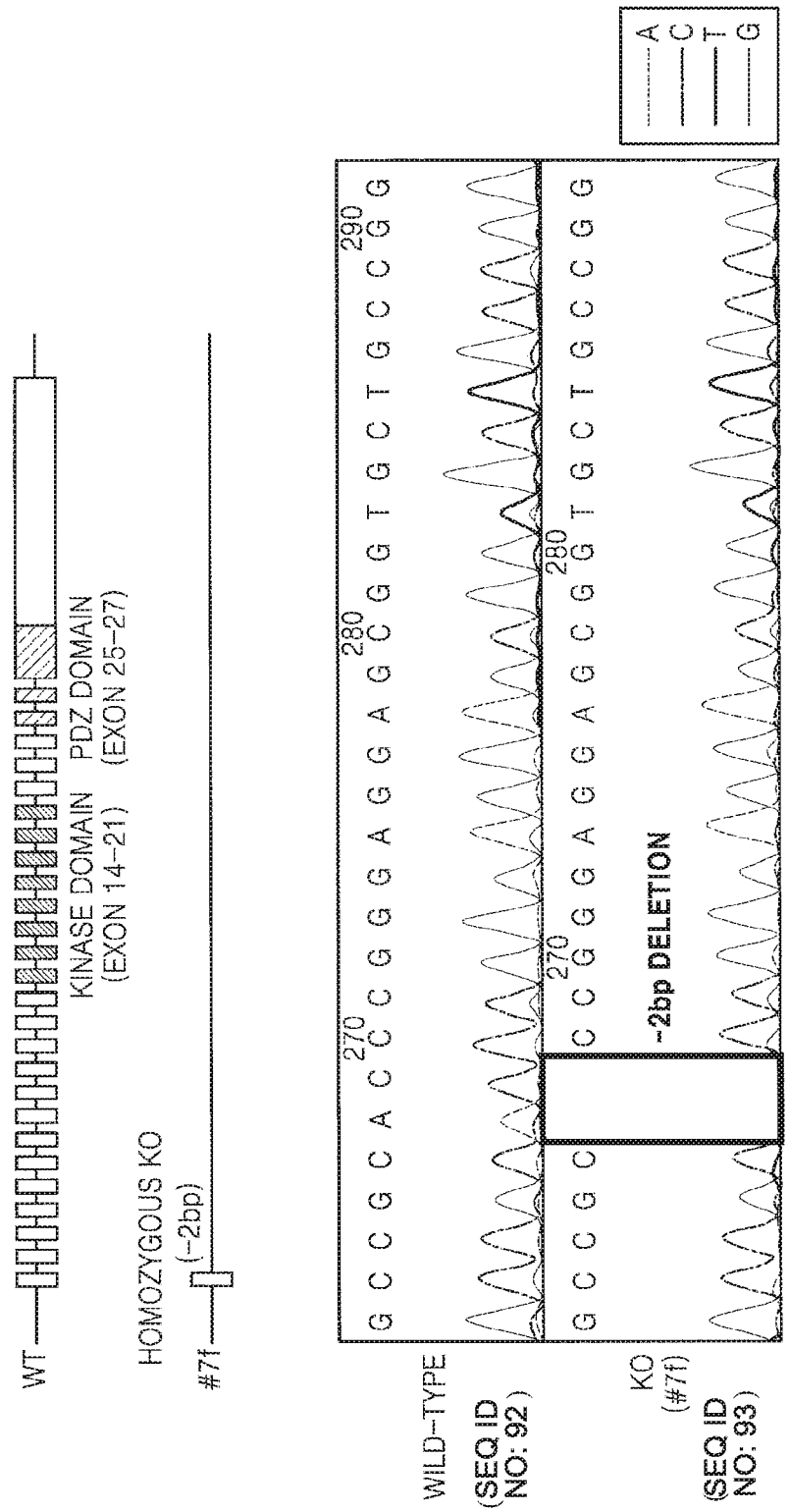
FIG. 3 shows identification of MAST4 knockout in C3H10T1/2 cells in which MAST4 was knocked out using the CRISPR/Cas9 system.

As a result, results were consistent with the RNA sequencing results of Example 1-2, and it was confirmed that expression of genes associated with extracellular matrix as a cartilage component was increased (FIG. 2).

1-4. Confirmation of Expression Level of Chondrocyte Marker in MAST4 Knockout Mouse To examine the effect of MAST4 knockout on chondrocytes, Col2a1 which is known as a chondrocyte marker was stained with fluorescence in the mouse tibia.

In detail, the tibia tissue was obtained from the mouse model of Example 1-1, and fixed with 4% paraformaldehyde (PFA, Wako, Osaka, JAPAN) in 0.01 M phosphate buffer saline (PBS, pH 7.4) at 4° C. overnight. The tissue was decalcified with 10% EDTA, and embedded in paraffin (Leica Biosystems, MO, USA), and sectioned 6 mm in thickness. The sample slide was stained with hematoxylin and eosin, and the tissue section was incubated with a primary antibody at 4° C. overnight. The primary antibody targets Col2a1 (Abcam, Cambridge, UK). After washing with PBS, the tissue section was sequentially incubated with AlexaFluor 488 (Invitrogen, CA, USA) at room temperature for 2 hours. Each image was obtained using a confocal microscope LSM700 (Carl Zeiss, Oberkochen, Germany), and a representative sample section was stained with freshly prepared Russell-Movatmodified pentachrome (American MasterTech, CA, USA).

Figure 10:
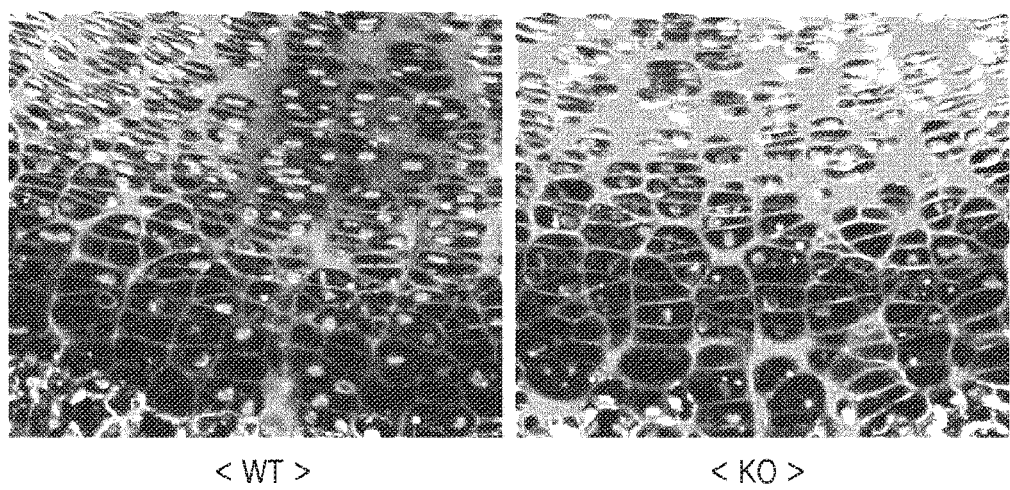
FIG. 10 shows chondrogenesis and regeneration effects in the tibia of the MAST4 knockout mouse.

As a result, FIG. 10 is an enlargement of a specific area of the observed sample, where Col2a1 (fluorescent green zone/grey background zone) was significantly increased in the tibia of the MAST4 knockout mouse model. TOPRO-3 (areas marked by red dots/gray dots) shows staining of the nuclei of chondrocytes. Therefore, it was confirmed that chondrogenesis and cartilage regeneration may be promoted by MAST4 knockout.

Example 2

Confirmation of Increased Expression of Cartilage Component in MAST4 Knockout Cells

2-1. Preparation of MAST4 Knockout Cells Using CRISPR/Cas9 System

To examine whether increased extracellular matrix in the MAST4 knockout mice is also reproduced in vitro, MAST4 knockout cells were prepared using the CRISPR/Cas9 system.

In detail, C3H/10T1/2, Clone 8 (ATCCCCL-226™) which is a mouse-derived fibroblast cell and is able to differentiate into chondrocytes was purchased ((C3H10T1/2 cell) provided by prof. Seon-Yong Jeong's lab, Department of Medical Genetics, School of Medicine, Ajou University). To knockout the cells, lentiCRISPR v2 (Plasmid #52961), pVSVg (AddGene 8454), and psPAX2 (AddGene 12260) were purchased from Addgene, and oligomers of the following Table 5 were used to insert guide RNA targeting exon 1 of mouse MAST4 gene (ENSMUSG00000034751) into LentiCRISPR v2 plasmid according to the manufacturer's instructions (lentiCRISPRv2 and lentiGuide oligo cloning protocol), thereby preparing a plasmid expressing guide RNA and Cas9 enzyme at the same time (as a control group, a plasmid having no guideRNA and expressing only Cas9 was used).

TABLE 5

| Oligomer | Sequence |
|---|---|
| mMAST4 CRISPR exon 1 sgRNA F (SEQ ID NO: 70) | 5'-CACCGTACCCTGCCGCTGCCGCACC-3' |
| mMAST4 CRISPR exon 1 sgRNA R (SEQ ID NO: 71) | 5'-AAACGGTGCGGCAGCGGCAGGGTAC-3' |
| mouse MAST4 exon 1 (SEQ ID NO: 72) | 5'-ATGGGGGAGAAAGTTTCCGAGGCGCCTG AGCCCGTGCCCCGGGGCTGCAGCGGACA CGGCGCCCGGACCCTAGTCTCTTCGGCG GCAGCCGTGTCCTCGGAGGGCGCTTCCT CAGCGGAGTCATCCTCTGGCTCGGAAACT CTGTCGGAGGAAGGGGAGCCCAGCCGCT TCTCCTGCAGGTCGCAGCCGCCGCGGCC |

TABLE 5-continued

| Oligomer | Sequence |
|---|---|
| | GCCGGGCGGCGCCCTGGGAACCCGGCT |
| | ACCCGCCGCGTGGGCTCCCGCGCGCGT |
| | GGCTCTGGAGCGTGGAGTCCCTACCCTG |
| | CCGCTGCCGCACCCGGGAGGAGCGGTG |
| | CTGCCGGTGCCCCAGGTCAGCAGCGCAT |
| | CCCAAGAGGAGCAGGATGAAGAG-3' |

This method is a lentivirus-based CRISPR knockout method. To prepare a virus, the three plasmids prepared above (LentiCRISPR v2 (+guide RNA): guide RNA+Cas9 expressing plasmid, pVSVg: Virus envelop plasmid, psPAX2: Virus packaging plasmid) were transfected into 293T cells using a polyethyenimine (PEI) reagent. 18 hours later, the medium was replaced with a fresh medium, and only the medium was collected, and viruses were obtained using a 0.45 μm filter. The obtained viruses were transfected into a 6-well dish to which C3H10T/12 was seeded. 24 hours after treatment with 1 ml of virus+1 ml of DMEM/FBS+2 μl of polybren, the medium was replaced with fresh DMEM/FBS. 24 hours later, only infected cells were selected by treatment with puromycin, and subcultured to 40% confluency in a 10 cm dish. Since gene editing by CRISPR may randomly occur in cells, single colony selection was performed. Cells were seeded in 10 cm dishes such that 50 cells existed in each dish. When cells formed colonies over time, these colonies were defined as one clone, and genomic DNA was extracted from each clone. PCR was performed using primers specifically amplifying exon 1 (F: 5'→3' CTGTGGTCCAACCTCTGTCA (SEQ ID NO:90), R: 5'→3' ATCGGCTCAGTGACACTTCC (SEQ ID NO:91)). The amplified PCR products were analyzed by the sequencing company. As a result of sequencing analysis, cells in which gene editing by frameshift was identified were used in the experiment, together with control cells. The sequences targeted by the prepared guide RNA were are in bold in Table 5. As a result of sequencing the MAST4 knockout results, deletion of two nucleotides occurred in mouse MAST4 exon 1, indicating frameshift induction.

2-2. RT-PCR for Confirmation of Change of Cartilage Component Expression in MAST4 Knockout Cells To examine changes in the extracellular matrix as a cartilage component in MAST4 knockout mice prepared in Example 1-1, RT-PCR was performed for respective genes.

10 μl of a medium containing total $10^5$ cells was put in the center of 12 wells, and incubated for 2 hours. 1 ml of DMEM containing 10% FBS was added to each well. 24 hours later, cells were harvested, and RNA was extracted using an easy-BLUE™ Total RNA Extraction Kit (Intron, Cat 17061) according to the manufacturer's instructions. Next, cDNA was synthesized using M-MLV reverse transcriptase (Promega, M1705) according to the manufacturer's instructions. Primers used in RT-PCR are as described in Table 4.

Figure 4:
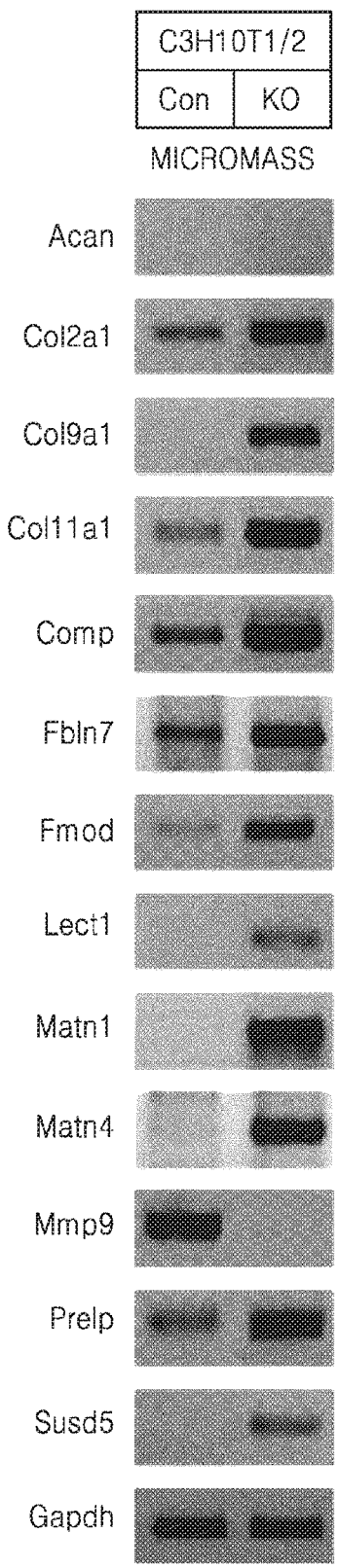
FIG. 4 shows RT-PCR results of examining changes in expression levels of respective genes in C3H10T1/2 cells in which MAST4 was knocked out using the CRISPR/Cas9 system.

As a result, increased expression of extracellular matrix-associated genes was also found in MAST4 knockout cells, as consistent with the results of Example 1-2 and Example 1-3 (FIG. 4), indicating that the same results as in the MAST4 knockout mouse were also obtained in vitro.

Example 3

Micromass Culture of MAST4 Knockout Cells and Confirmation of Increased Cartilage Differentiation Activity

3-1. Micromass Culture of MAST4 Knockout Cells

To evaluate chondrogenic ability of the MAST4 knockout cells of Example 2-2, micromass culture was performed.

In detail, MAST4 knockout cells were prepared as in Example 2-1, and micromass culture was performed with reference to a known method (Differentiation and Mineralization of Murine Mesenchymal C3H10T1/2 Cells in Micromass Culture, 2010, Rani Roy). First, 10 μl of a medium containing total $10^5$ fibroblast cells were put in the center of each well of a 12-well plate, and incubated for 2 hours. 1 ml of DMEM containing 10% FBS was added to each well. Thereafter, 100 ng/ml, 500 ng/ml, or 1000 ng/ml of BMP2 was added to each culture depending on the purpose of cartilage induction, respectively. Thereafter, the medium was replaced with a fresh medium every three days.

3-2. Confirmation of Reproduction of Effects of Micromass-Cultured MAST4 Knockout Cells To examine whether production of extracellular matrix as a cartilage component was also increased in the MAST4 knockout cells cultured according to Example 3-1, as in the MAST4 knockout cells of Example 2-2, and finally, chondrogenic ability was increased therein, RT-PCR was performed.

In detail, cells, which were cultured for 0 day, 3 days, and 6 days from the day when the cells were seeded in a plate for micromass culture, were harvested, respectively, and RNA was extracted therefrom on the same day. RT-PCR was performed for respective genes, as in Example 1-3, and whether or not production of the cartilage component was increased was examined.

Figure 5:
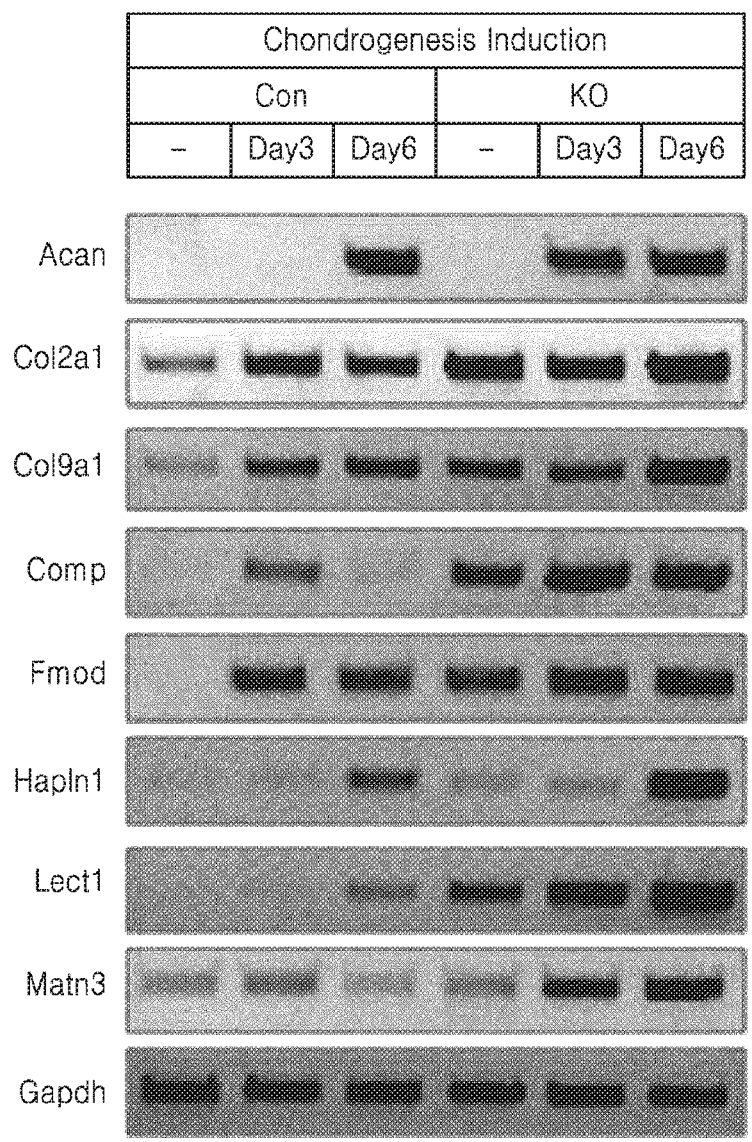
FIG. 5 shows RT-PCR results of examining changes in expression levels of respective genes in a micromass culture to confirm chondrogenesis.

As a result, as consistent with the results observed in the MAST4 knockout cells of Example 2-2, expression of extracellular matrix components was increased, and at the same time, differentiation into chondrocytes began with aggrecan expression on day 3 after induction using BMP2, and as a result, it was confirmed that chondrogenic ability was increased (FIG. 5). In particular, when MAST4 was knock-outed, some genes (hapln1) showed no significant difference in the expression on day 3, but all of the indicated extracellular matrix-associated genes showed overexpression on day 6. In contrast, in the control group, some proteins were less expressed or rather decreased on day 6 (e.g., Matn3, or Comp). The MAST4 knockout cells were found to be useful in the overexpression of all various extracellular matrices.

3-3. Confirmation of Chondrogenesis of Mass-Cultured MAST4 Knockout Cells

With regard to the overexpression of the respective extracellular matrix-associated genes observed in Example 3-2, to examine whether or not the expression was actually increased at the level of isolated proteins, not at the gene expression level, alcian blue staining was performed.

In detail, plates of cells corresponding to each date were washed twice with PBS and fixed for 15 minutes by adding 1 ml of 4% paraformaldehyde. Then, 1 ml of 1% alcian blue 8-GX (Sigma-Aldrich, A5268) dissolved in 0.1 N HCl (pH 1.0) was added and stained overnight. After washing twice with 500 µl of 0.1 N HCl, images were obtained.

Figure 6:
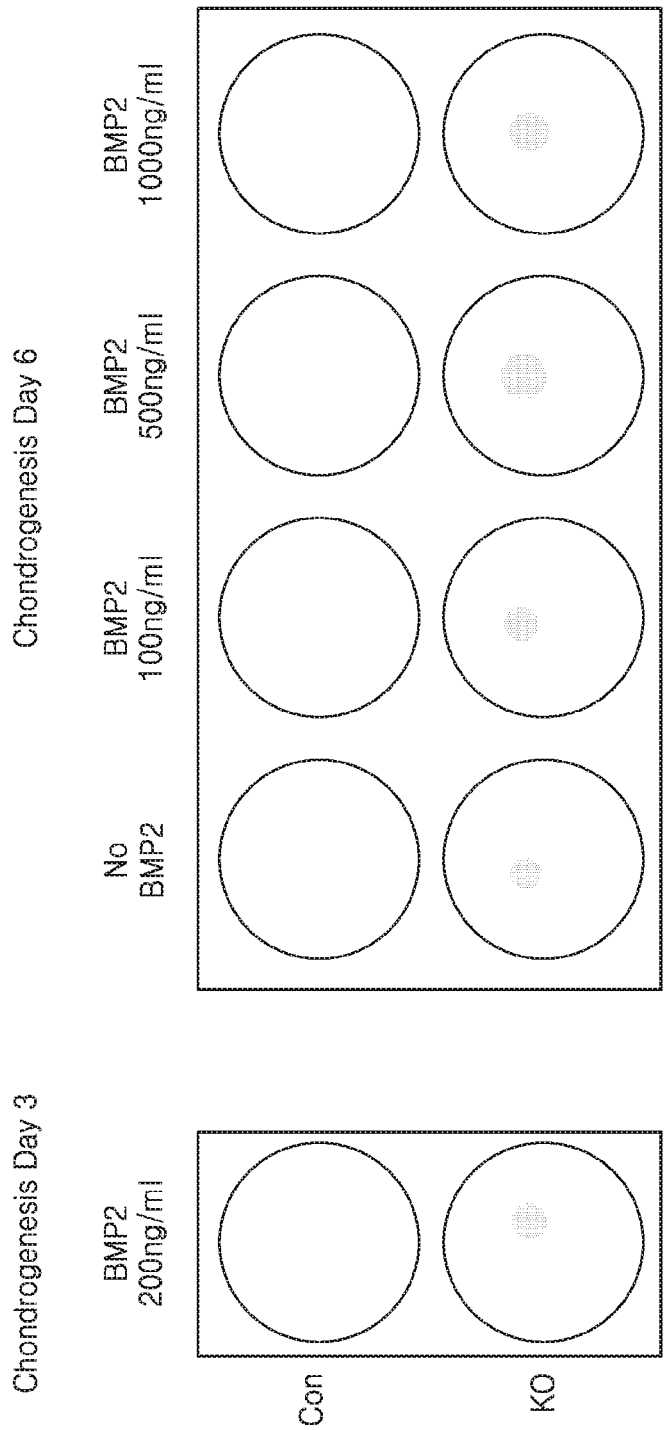
FIG. 6 shows alcian blue staining results of examining a difference in cartilage differentiation in C3H10T1/2 cells in which MAST4 was knocked out using the CRISPR/Cas9 system.

As a result, in the case of MAST4 knockout cells, chondrogenesis was increased from day 3, and extracellular matrix secretion was increased, and the degree was increased with increasing BMP2 concentration (FIG. 6).

Example 4

Confirmation of Effect of Suppression of MAST4 Expression in Human Cells

Example 4-1. Confirmation of Effect of Suppression of MAST4 Expression in Human Cells It was examined whether the results confirmed in the knockout mouse model and mouse cells were also induced in human cells.

In detail, human primary chondrocytes (donated by College of Medicine, Inha University) were knocked-out by transient transfection with MAST4 siRNA(h) (sc-106201; Santa Cruz biotechnology) (FIG. 8A) or MAST4 expression was knocked-out by the CRISPR/Cas9 system. MAST4 siRNA was transfected using a Lipofectamine RNAiMAX transfection reagent of ThermoFisher SCIENCITFIC, and information of primers used herein is as described in the following Table 6. Preparation and treatment of the CRISPR/Cas9 system were performed in the same manner as in Example 1-1 with reference to GeneArt™ Precision gRNA Synthesis Kit (A29377) of ThermoScientific, and information of primers used herein is as described in the following Table 6.

For high transfection efficiency, siRNA transfection was performed by a reverse transfection technique in which cell planting and transfection are performed at the same time, and a transfection reagent was Lipofectamine RNAiMAX transfection reagent of ThermoFisher SCIENCITFIC. In detail, 15 nM of MAST4 siRNA and 4.5 µl of Lipofectamine RNAiMax were mixed in 40 µl of Gibco™ Opti-MEM™, and incubated for 15 minutes. Thereafter, human primary chondrocytes of $1.5 \times 10^5$ cell/well were plated together with 2 ml of a medium (FBS 10%) containing no gentamicin in a 6-well plate (Coll coated plate), and the siRNA mixture was added thereto. 72 hours later, the cells were harvested and RNA was isolated. Human primary chondrocytes were cultured in a collagen I-coated flask (175, Col I Straight Vent 356487, Corning) under conditions of DMEM (17-205-CVR Corning), FBS Qualified (USA origin 500 mL 26140-079, Gibco), L-glutamine (200 mM) (100× 25030-081, Gibco), and gentamicin (5 ug/ml) (10 mL 15700-060, Thermofisher).

Knockout was performed by targeting 20 nt on the genome of MAST4 (target sequences are marked in bold), and specifically, #1 and #3 target Exon5, and #2 targets Exon 8. #1 and #3 were prepared in the reverse direction, and #2 was prepared in the forward direction. The human MAST4 gene used in the preparation of CRISPR/Cas9 system was with reference to MAST4 ENSG00000069020 (http://asia.ensembl.org/). Information of targeted Exon sequences and NGG PAM sequences (grey box) on which CRISPR deletion occurred are shown in detail in FIG. 7.

TABLE 6

| | |
|---|---|
| hMAST4 CR#1 F (SEQ ID NO: 73) | 5'-TAATACGACTCACTATAG GAGTGTGGTCGAGGCAATGC-3' |
| hMAST4 CR#1 R (SEQ ID NO: 74) | 5'-TTCTAGCTCTAAAAC GCATTGCCTCGACCACACTC-3' |
| hMAST4 CR#2 F (SEQ ID NO: 75) | 5'-TAATACGACTCACTATAG GTAACTCGTCTGGTGTTGGT-3' |
| hMAST4 CR#2 R (SEQ ID NO: 76) | 5'-TTCTAGCTCTAAAAC ACCAACACCAGACGAGTTAC-3' |
| hMAST4 CR#3 F (SEQ ID NO: 77) | 5'-TAATACGACTCACTATAG AGCAACCGGAAAAGCTTAAT-3' |
| hMAST4 CR#3 R (SEQ ID NO: 78) | 5'-TTCTAGCTCTAAAAC ATTAAGCTTTTCCGGTTGCT-3' |
| HumanAcanRT Forward (336) (SEQ ID NO: 82) | 5'-gaatcaactgctgcagacca-3' |
| HumanAcan RT Reverse (336) (SEQ ID NO: 83) | 5'-gtgccagatcatcaccacac-3' |
| HumanCol9a1RT Forward (467) (SEQ ID NO: 84) | 5'-CGTGGATTTCCAGGCCGTGG-3' |
| HumanCol9a1RT Reverse (467) (SEQ ID NO: 85) | 5'-TCGCTGTCCTTGATCACCAG-3' |
| HumanGapdhRT Forward (156) (SEQ ID NO: 86) | 5'-TGGCAAAGTGGAGATTGTTGCC-3' |
| HumanGapdhRT Reverse (156) (SEQ ID NO: 87) | 5'-AAGATGGTGATGGGCTTCCCG-3' |

Figure 8A:
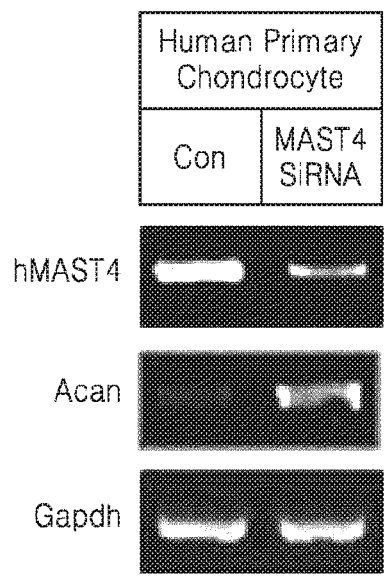
FIG. 8A shows human chondrocytes in which MAST4 was knocked out using siRNA.
Figure 8B:
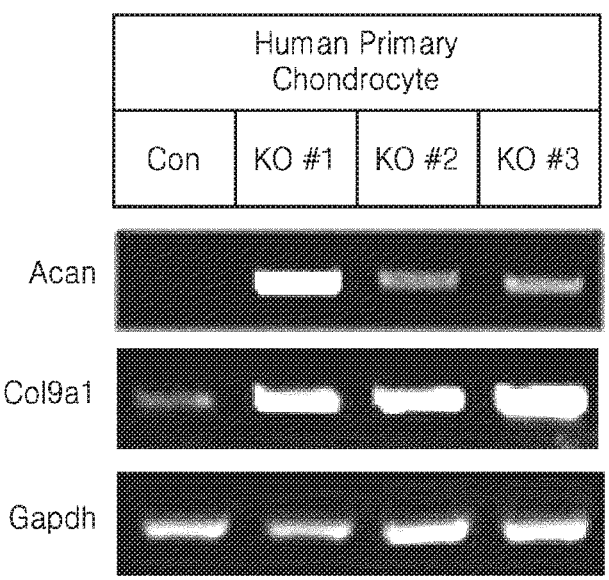
FIG. 8B shows expression levels of extracellular matrix factors in human chondrocytes in which MAST4 was knocked out using the CRISPR/Cas9 system.

As a result, as shown in FIG. 8A, when MAST4 siRNA was transfected, MAST4 expression was decreased, and at this time, expression of extracellular matrix factors such as Acan was increased. Further, as shown in FIG. 8B, when MAST4 was knocked out, expression of extracellular matrix factors such as Acan and Col9a1 was increased. These results are the same as those demonstrated in the previous mouse models and mouse cells. Therefore, with regard to other extracellular matrix factors and chondrogenic effects, the same results as those demonstrated in the mouse may be also obtained by suppressing MAST4 expression in human cells.

Example 4-2. Suppression of MAST4 Expression by TGF-β1 in Human Cells and Confirmation of Effect Thereof It was examined whether suppression of MAST4 expression as confirmed in Example 4-1 was induced by TGF-β1 and expression of extracellular matrix factors was affected thereby.

In detail, the human primary chondrocytes of Example 4-1 were treated with TGF-β1, and an expression level thereof was measured by RT-PCR as in Examples 1-2 and 1-3 and Western blotting.

Figure 9A:
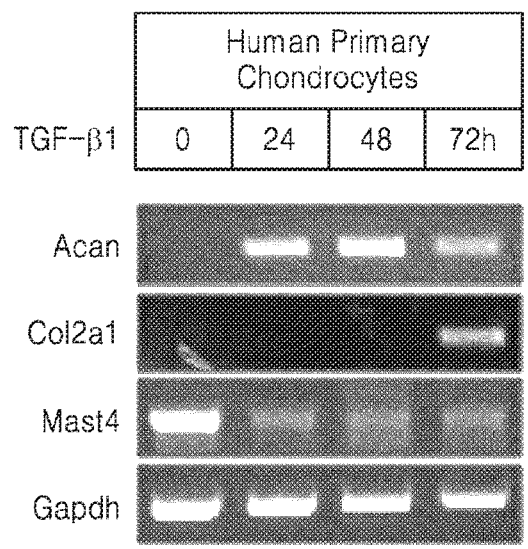
FIG. 9 shows changes in the expression level of MAST4 after treatment of human primary chondrocytes with TGF-β1, and expression levels of extracellular matrix factors thereby.
Figure 9B:
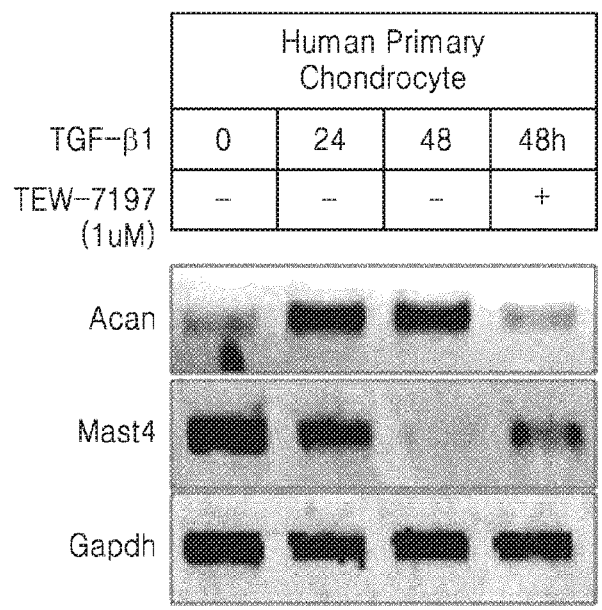

As a result, as shown in FIG. 9, when TGF-β1 (5 ng/ml) was treated for 24 hours, 48 hours, or 72 hours, respectively, MAST4 expression was suppressed, and as a result, expression of extracellular matrix factors was increased. When co-treatment with TGF-β1 (5 ng/ml) and TEW-7197 which is a TGF-β1 inhibitor was performed (FIG. 9B), Acan expression increased by TGF-β1 was suppressed and the inhibitory effect on MAST4 expression was also decreased, as compared with single treatment with TGF-β1.

The invention claimed is:

1. A method of producing extracellular matrix from eukaryotic cells, comprising contacting the eukaryotic cells with a composition comprising a compound capable of specifically binding to a nucleic acid encoding Microtubule Associated Serine/Threonine Kinase Family Member 4 (MAST4) protein or a fragment thereof and inhibits expression or activity of the MAST4 protein, wherein the compound capable of specifically binding to the nucleic acid encoding the MAST4 protein or the fragment thereof is CRISPR-Cas comprising guide RNA specific to the nucleic acid encoding the MAST4 protein or the fragment thereof, wherein the eukaryotic cells are chondrocytes, fibroblasts or mesenchymal stem cells.

2. The method of claim 1, wherein the nucleic acid encodes the MAST4 protein of any one amino acid sequence of SEQ ID NOS: 1 to 7 and 15, or the nucleic acid encoding the MAST4 protein comprises any one polynucleotide sequence of SEQ ID NOS: 8 to 14 and 16.

3. The method of claim 1, wherein the guide RNA is a dual RNA comprising CRISPR RNA (crRNA) and transactivating crRNA (tracrRNA) specific to the nucleic acid encoding the MAST4 protein or the fragment thereof, or a single strand guide RNA comprising parts of the crRNA and the tracrRNA and hybridizing with the nucleic acid encoding the MAST4 protein or the fragment thereof.

4. The method of claim 1, wherein the eukaryotic cells are chondrocytes or mesenchymal stem cells.

5. The method of claim 1, wherein the composition promotes or induces chondrogenesis of the eukaryotic cells.

6. The method of claim 1, further comprising contacting the eukaryotic cells with TGF-β1.

7. The method of claim 1, further comprising contacting the eukaryotic cells with a chondrogenic inducer.

8. A method of preventing, treating, or improving a joint disease, the method comprising administering to a subject in need thereof at or near a joint in need thereof where cartilage is desired to be formed, eukaryotic cells in which expression or activity of Microtubule Associated Serine/Threonine Kinase Family Member 4 (MAST4) protein is inhibited, wherein the eukaryotic cells are chondrocytes, fibroblasts or mesenchymal stem cells.

9. The method of claim 8, wherein the MAST4 protein has an amino acid sequence of SEQ ID NOS: 1 to 7 or 15, or the nucleic acid encoding the MAST4 protein comprises any one polynucleotide sequence of SEQ ID NOS: 8 to 14 and 16.

10. The method of claim 8, wherein the eukaryotic cells are chondrocytes.

11. The method of claim 8, wherein the eukaryotic cells are mesenchymal stem cells.

12. The method of claim 8, further comprising administering TGF-β1.

13. The method of claim 8, further comprising administering a chondrogenic inducer.

14. A method of preventing, treating, or improving a joint disease, the method comprising
(i) gene editing Microtubule Associated Serine/Threonine Kinase Family Member 4 (MAST4) in a eukaryotic cell, such that MAST4 protein expression or activity is inhibited; and
(ii) administering to a subject in need thereof at or near a joint in need thereof where cartilage is desired to be formed, the eukaryotic cells obtained thereby.

15. The method of claim 14, wherein the eukaryotic cells are mesenchymal stem cells, fibroblast cells or chondrocytes.

16. The method of claim 15, wherein the eukaryotic cells are mesenchymal stem cells.

17. The method of claim 14, further comprising administering TGF-β1.

18. The method of claim 14, further comprising administering a chondrogenic inducer.

19. The method of claim 14, wherein the gene editing is carried out by binding a CRISPR-Cas comprising guide RNA specific to the nucleic acid encoding the MAST4 protein or the fragment thereof to the nucleic acid encoding the MAST4 protein or the fragment thereof.

20. The method of claim 19, wherein the guide RNA is a dual RNA comprising CRISPR RNA (crRNA) and transactivating crRNA (tracrRNA) specific to the nucleic acid encoding the MAST4 protein or the fragment thereof, or a single strand guide RNA comprising parts of the crRNA and the tracrRNA and hybridizing with the nucleic acid encoding the MAST4 protein or the fragment thereof.

21. The method of claim 1, which is carried out in vitro.

* * * * *

SEQUENCE LISTING

<160> NUMBER OF SEQ ID NOS: 93

<210> SEQ ID NO 1
<211> LENGTH: 2434
<212> TYPE: PRT
<213> ORGANISM: Homo sapiens

<400> SEQUENCE: 1

```
Met Asp Glu Ser Ser Ile Leu Arg Arg Gly Leu Gln Lys Glu Leu
1               5                   10                  15

Ser Leu Pro Arg Arg Gly Ser Leu Ile Asp Ser Gln Lys Trp Asn Cys
            20                  25                  30

Leu Val Lys Arg Cys Arg Thr Ser Asn Arg Lys Ser Leu Ile Gly Asn
            35                  40                  45

Gly Gln Ser Pro Ala Leu Pro Arg Pro His Ser Pro Leu Ser Ala His
        50                  55                  60

Ala Gly Asn Ser Pro Gln Asp Ser Pro Arg Asn Phe Ser Pro Ser Ala
65                  70                  75                  80

Ser Ala His Phe Ser Phe Ala Arg Arg Thr Asp Gly Arg Arg Trp Ser
                85                  90                  95

Leu Ala Ser Leu Pro Ser Ser Gly Tyr Gly Thr Asn Thr Pro Ser Ser
            100                 105                 110

Thr Val Ser Ser Cys Ser Ser Gln Glu Lys Leu His Gln Leu Pro
            115                 120                 125

Tyr Gln Pro Thr Pro Asp Glu Leu His Phe Leu Ser Lys His Phe Cys
        130                 135                 140

Thr Thr Glu Ser Ile Ala Thr Glu Asn Arg Cys Arg Asn Thr Pro Met
145                 150                 155                 160

Arg Pro Arg Ser Arg Ser Leu Ser Pro Gly Arg Ser Pro Ala Cys Cys
                165                 170                 175

Asp His Glu Ile Ile Met Met Asn His Val Tyr Lys Glu Arg Phe Pro
            180                 185                 190

Lys Ala Thr Ala Gln Met Glu Glu Arg Leu Lys Glu Ile Ile Thr Ser
        195                 200                 205

Tyr Ser Pro Asp Asn Val Leu Pro Leu Ala Asp Gly Val Leu Ser Phe
    210                 215                 220

Thr His His Gln Ile Ile Glu Leu Ala Arg Asp Cys Leu Asp Lys Ser
225                 230                 235                 240

His Gln Gly Leu Ile Thr Ser Arg Tyr Phe Leu Glu Leu Gln His Lys
                245                 250                 255

Leu Asp Lys Leu Leu Gln Glu Ala His Asp Arg Ser Glu Ser Gly Glu
            260                 265                 270

Leu Ala Phe Ile Lys Gln Leu Val Arg Lys Ile Leu Ile Val Ile Ala
        275                 280                 285

Arg Pro Ala Arg Leu Leu Glu Cys Leu Glu Phe Asp Pro Glu Glu Phe
    290                 295                 300

Tyr Tyr Leu Leu Glu Ala Ala Glu Gly His Ala Lys Glu Gly Gln Gly
305                 310                 315                 320

Ile Lys Thr Asp Ile Pro Arg Tyr Ile Ile Ser Gln Leu Gly Leu Asn
                325                 330                 335
```

-continued

```
Lys Asp Pro Leu Glu Glu Met Ala His Leu Gly Asn Tyr Asp Ser Gly
                340                 345                 350

Thr Ala Glu Thr Pro Glu Thr Asp Glu Ser Val Ser Ser Ser Asn Ala
            355                 360                 365

Ser Leu Lys Leu Arg Arg Lys Pro Arg Glu Ser Asp Phe Glu Thr Ile
        370                 375                 380

Lys Leu Ile Ser Asn Gly Ala Tyr Gly Ala Val Tyr Phe Val Arg His
385                 390                 395                 400

Lys Glu Ser Arg Gln Arg Phe Ala Met Lys Lys Ile Asn Lys Gln Asn
                405                 410                 415

Leu Ile Leu Arg Asn Gln Ile Gln Gln Ala Phe Val Glu Arg Asp Ile
            420                 425                 430

Leu Thr Phe Ala Glu Asn Pro Phe Val Val Ser Met Tyr Cys Ser Phe
        435                 440                 445

Glu Thr Arg Arg His Leu Cys Met Val Met Glu Tyr Val Glu Gly Gly
    450                 455                 460

Asp Cys Ala Thr Leu Met Lys Asn Met Gly Pro Leu Pro Val Asp Met
465                 470                 475                 480

Ala Arg Met Tyr Phe Ala Glu Thr Val Leu Ala Leu Glu Tyr Leu His
                485                 490                 495

Asn Tyr Gly Ile Val His Arg Asp Leu Lys Pro Asp Asn Leu Leu Val
            500                 505                 510

Thr Ser Met Gly His Ile Lys Leu Thr Asp Phe Gly Leu Ser Lys Val
        515                 520                 525

Gly Leu Met Ser Met Thr Thr Asn Leu Tyr Glu Gly His Ile Glu Lys
    530                 535                 540

Asp Ala Arg Glu Phe Leu Asp Lys Gln Val Cys Gly Thr Pro Glu Tyr
545                 550                 555                 560

Ile Ala Pro Glu Val Ile Leu Arg Gln Gly Tyr Gly Lys Pro Val Asp
                565                 570                 575

Trp Trp Ala Met Gly Ile Ile Leu Tyr Glu Phe Leu Val Gly Cys Val
            580                 585                 590

Pro Phe Phe Gly Asp Thr Pro Glu Glu Leu Phe Gly Gln Val Ile Ser
        595                 600                 605

Asp Glu Ile Asn Trp Pro Glu Lys Asp Glu Ala Pro Pro Asp Ala
    610                 615                 620

Gln Asp Leu Ile Thr Leu Leu Leu Arg Gln Asn Pro Leu Glu Arg Leu
625                 630                 635                 640

Gly Thr Gly Gly Ala Tyr Glu Val Lys Gln His Arg Phe Phe Arg Ser
                645                 650                 655

Leu Asp Trp Asn Ser Leu Leu Arg Gln Lys Ala Glu Phe Ile Pro Gln
            660                 665                 670

Leu Glu Ser Glu Asp Asp Thr Ser Tyr Phe Asp Thr Arg Ser Glu Lys
        675                 680                 685

Tyr His His Met Glu Thr Glu Glu Asp Asp Thr Asn Asp Glu Asp
    690                 695                 700

Phe Asn Val Glu Ile Arg Gln Phe Ser Ser Cys Ser His Arg Phe Ser
705                 710                 715                 720

Lys Val Phe Ser Ser Ile Asp Arg Ile Thr Gln Asn Ser Ala Glu Glu
                725                 730                 735

Lys Glu Asp Ser Val Asp Lys Thr Lys Ser Thr Thr Leu Pro Ser Thr
            740                 745                 750
```

-continued

```
Glu Thr Leu Ser Trp Ser Ser Glu Tyr Ser Glu Met Gln Gln Leu Ser
            755                 760                 765

Thr Ser Asn Ser Ser Asp Thr Glu Ser Asn Arg His Lys Leu Ser Ser
    770                 775                 780

Gly Leu Leu Pro Lys Leu Ala Ile Ser Thr Glu Gly Glu Gln Asp Glu
785                 790                 795                 800

Ala Ala Ser Cys Pro Gly Asp Pro His Glu Glu Pro Gly Lys Pro Ala
                805                 810                 815

Leu Pro Pro Glu Glu Cys Ala Gln Glu Pro Glu Val Thr Thr Pro
            820                 825                 830

Ala Ser Thr Ile Ser Ser Ser Thr Leu Ser Val Gly Ser Phe Ser Glu
            835                 840                 845

His Leu Asp Gln Ile Asn Gly Arg Ser Glu Cys Val Asp Ser Thr Asp
        850                 855                 860

Asn Ser Ser Lys Pro Ser Ser Glu Pro Ala Ser His Met Ala Arg Gln
865                 870                 875                 880

Arg Leu Glu Ser Thr Glu Lys Lys Lys Ile Ser Gly Lys Val Thr Lys
                885                 890                 895

Ser Leu Ser Ala Ser Ala Leu Ser Leu Met Ile Pro Gly Asp Met Phe
            900                 905                 910

Ala Val Ser Pro Leu Gly Ser Pro Met Ser Pro His Ser Leu Ser Ser
            915                 920                 925

Asp Pro Ser Ser Ser Arg Asp Ser Ser Pro Ser Arg Asp Ser Ser Ala
            930                 935                 940

Ala Ser Ala Ser Pro His Gln Pro Ile Val Ile His Ser Ser Gly Lys
945                 950                 955                 960

Asn Tyr Gly Phe Thr Ile Arg Ala Ile Arg Val Tyr Val Gly Asp Ser
                965                 970                 975

Asp Ile Tyr Thr Val His His Ile Val Trp Asn Val Glu Glu Gly Ser
            980                 985                 990

Pro Ala Cys Gln Ala Gly Leu Lys Ala Gly Asp Leu Ile Thr His Ile
        995                 1000                1005

Asn Gly Glu Pro Val His Gly Leu Val His Thr Glu Val Ile Glu Leu
    1010                1015                1020

Leu Leu Lys Ser Gly Asn Lys Val Ser Ile Thr Thr Thr Pro Phe Glu
1025                1030                1035                1040

Asn Thr Ser Ile Lys Thr Gly Pro Ala Arg Arg Asn Ser Tyr Lys Ser
                1045                1050                1055

Arg Met Val Arg Arg Ser Lys Lys Ser Lys Lys Lys Glu Ser Leu Glu
        1060                1065                1070

Arg Arg Arg Ser Leu Phe Lys Lys Leu Ala Lys Gln Pro Ser Pro Leu
    1075                1080                1085

Leu His Thr Ser Arg Ser Phe Ser Cys Leu Asn Arg Ser Leu Ser Ser
    1090                1095                1100

Gly Glu Ser Leu Pro Gly Ser Pro Thr His Ser Leu Ser Pro Arg Ser
1105                1110                1115                1120

Pro Thr Pro Ser Tyr Arg Ser Thr Pro Asp Phe Pro Ser Gly Thr Asn
                1125                1130                1135

Ser Ser Gln Ser Ser Ser Pro Ser Ser Ala Pro Asn Ser Pro Ala
            1140                1145                1150

Gly Ser Gly His Ile Arg Pro Ser Thr Leu His Gly Leu Ala Pro Lys
            1155                1160                1165
```

-continued

Leu Gly Gly Gln Arg Tyr Arg Ser Gly Arg Arg Lys Ser Ala Gly Asn
1170                1175                1180

Ile Pro Leu Ser Pro Leu Ala Arg Thr Pro Ser Pro Thr Pro Gln Pro
1185                1190                1195                1200

Thr Ser Pro Gln Arg Ser Pro Ser Pro Leu Leu Gly His Ser Leu Gly
            1205                1210                1215

Asn Ser Lys Ile Ala Gln Ala Phe Pro Ser Lys Met His Ser Pro Pro
            1220                1225                1230

Thr Ile Val Arg His Ile Val Arg Pro Lys Ser Ala Glu Pro Pro Arg
            1235                1240                1245

Ser Pro Leu Leu Lys Arg Val Gln Ser Glu Glu Lys Leu Ser Pro Ser
            1250                1255                1260

Tyr Gly Ser Asp Lys Lys His Leu Cys Ser Arg Lys His Ser Leu Glu
1265                1270                1275                1280

Val Thr Gln Glu Glu Val Gln Arg Glu Gln Ser Gln Arg Glu Ala Pro
                1285                1290                1295

Leu Gln Ser Leu Asp Glu Asn Val Cys Asp Val Pro Pro Leu Ser Arg
            1300                1305                1310

Ala Arg Pro Val Glu Gln Gly Cys Leu Lys Arg Pro Val Ser Arg Lys
            1315                1320                1325

Val Gly Arg Gln Glu Ser Val Asp Asp Leu Asp Arg Asp Lys Leu Lys
            1330                1335                1340

Ala Lys Val Val Val Lys Lys Ala Asp Gly Phe Pro Glu Lys Gln Glu
1345                1350                1355                1360

Ser His Gln Lys Ser His Gly Pro Gly Ser Asp Leu Glu Asn Phe Ala
            1365                1370                1375

Leu Phe Lys Leu Glu Glu Arg Glu Lys Lys Val Tyr Pro Lys Ala Val
            1380                1385                1390

Glu Arg Ser Ser Thr Phe Glu Asn Lys Ala Ser Met Gln Glu Ala Pro
            1395                1400                1405

Pro Leu Gly Ser Leu Leu Lys Asp Ala Leu His Lys Gln Ala Ser Val
            1410                1415                1420

Arg Ala Ser Glu Gly Ala Met Ser Asp Gly Arg Val Pro Ala Glu His
1425                1430                1435                1440

Arg Gln Gly Gly Gly Asp Phe Arg Arg Ala Pro Ala Pro Gly Thr Leu
            1445                1450                1455

Gln Asp Gly Leu Cys His Ser Leu Asp Arg Gly Ile Ser Gly Lys Gly
            1460                1465                1470

Glu Gly Thr Glu Lys Ser Ser Gln Ala Lys Glu Leu Leu Arg Cys Glu
            1475                1480                1485

Lys Leu Asp Ser Lys Leu Ala Asn Ile Asp Tyr Leu Arg Lys Lys Met
            1490                1495                1500

Ser Leu Glu Asp Lys Glu Asp Asn Leu Cys Pro Val Leu Lys Pro Lys
            1505                1510                1515                1520

Met Thr Ala Gly Ser His Glu Cys Leu Pro Gly Asn Pro Val Arg Pro
            1525                1530                1535

Thr Gly Gly Gln Gln Glu Pro Pro Pro Ala Ser Glu Ser Arg Ala Phe
            1540                1545                1550

Val Ser Ser Thr His Ala Ala Gln Met Ser Ala Val Ser Phe Val Pro
            1555                1560                1565

Leu Lys Ala Leu Thr Gly Arg Val Asp Ser Gly Thr Glu Lys Pro Gly
            1570                1575                1580

-continued

Leu Val Ala Pro Glu Ser Pro Val Arg Lys Ser Pro Ser Glu Tyr Lys
1585                1590                1595                1600

Leu Glu Gly Arg Ser Val Ser Cys Leu Lys Pro Ile Glu Gly Thr Leu
            1605                1610                1615

Asp Ile Ala Leu Leu Ser Gly Pro Gln Ala Ser Lys Thr Glu Leu Pro
        1620                1625                1630

Ser Pro Glu Ser Ala Gln Ser Pro Ser Pro Ser Gly Asp Val Arg Ala
    1635                1640                1645

Ser Val Pro Pro Val Leu Pro Ser Ser Ser Gly Lys Lys Asn Asp Thr
1650                1655                1660

Thr Ser Ala Arg Glu Leu Ser Pro Ser Ser Leu Lys Met Asn Lys Ser
1665                1670                1675                1680

Tyr Leu Leu Glu Pro Trp Phe Leu Pro Pro Ser Arg Gly Leu Gln Asn
            1685                1690                1695

Ser Pro Ala Val Ser Leu Pro Asp Pro Glu Phe Lys Arg Asp Arg Lys
        1700                1705                1710

Gly Pro His Pro Thr Ala Arg Ser Pro Gly Thr Val Met Glu Ser Asn
    1715                1720                1725

Pro Gln Gln Arg Glu Gly Ser Ser Pro Lys His Gln Asp His Thr Thr
1730                1735                1740

Asp Pro Lys Leu Leu Thr Cys Leu Gly Gln Asn Leu His Ser Pro Asp
1745                1750                1755                1760

Leu Ala Arg Pro Arg Cys Pro Leu Pro Pro Glu Ala Ser Pro Ser Arg
            1765                1770                1775

Glu Lys Pro Gly Leu Arg Glu Ser Ser Glu Arg Gly Pro Pro Thr Ala
        1780                1785                1790

Arg Ser Glu Arg Ser Ala Ala Arg Ala Asp Thr Cys Arg Glu Pro Ser
    1795                1800                1805

Met Glu Leu Cys Phe Pro Glu Thr Ala Lys Thr Ser Asp Asn Ser Lys
1810                1815                1820

Asn Leu Leu Ser Val Gly Arg Thr His Pro Asp Phe Tyr Thr Gln Thr
1825                1830                1835                1840

Gln Ala Met Glu Lys Ala Trp Ala Pro Gly Gly Lys Thr Asn His Lys
            1845                1850                1855

Asp Gly Pro Gly Glu Ala Arg Pro Pro Arg Asp Asn Ser Ser Leu
        1860                1865                1870

His Ser Ala Gly Ile Pro Cys Glu Lys Glu Leu Gly Lys Val Arg Arg
    1875                1880                1885

Gly Val Glu Pro Lys Pro Glu Ala Leu Leu Ala Arg Arg Ser Leu Gln
1890                1895                1900

Pro Pro Gly Ile Glu Ser Glu Lys Ser Glu Lys Leu Ser Ser Phe Pro
1905                1910                1915                1920

Ser Leu Gln Lys Asp Gly Ala Lys Glu Pro Glu Arg Lys Glu Gln Pro
            1925                1930                1935

Leu Gln Arg His Pro Ser Ser Ile Pro Pro Pro Leu Thr Ala Lys
        1940                1945                1950

Asp Leu Ser Ser Pro Ala Ala Arg Gln His Cys Ser Ser Pro Ser His
    1955                1960                1965

Ala Ser Gly Arg Glu Pro Gly Ala Lys Pro Ser Thr Ala Glu Pro Ser
1970                1975                1980

Ser Ser Pro Gln Asp Pro Pro Lys Pro Val Ala Ala His Ser Glu Ser
1985                1990                1995                2000

```
Ser Ser His Lys Pro Arg Pro Gly Pro Asp Pro Gly Pro Pro Lys Thr
            2005                2010                2015

Lys His Pro Asp Arg Ser Leu Ser Ser Gln Lys Pro Ser Val Gly Ala
        2020                2025                2030

Thr Lys Gly Lys Glu Pro Ala Thr Gln Ser Leu Gly Gly Ser Ser Arg
        2035                2040                2045

Glu Gly Lys Gly His Ser Lys Ser Gly Pro Asp Val Phe Pro Ala Thr
    2050                2055                2060

Pro Gly Ser Gln Asn Lys Ala Ser Asp Gly Ile Gly Gln Gly Glu Gly
2065                2070                2075                2080

Gly Pro Ser Val Pro Leu His Thr Asp Arg Ala Pro Leu Asp Ala Lys
            2085                2090                2095

Pro Gln Pro Thr Ser Gly Gly Arg Pro Leu Glu Val Leu Glu Lys Pro
            2100                2105                2110

Val His Leu Pro Arg Pro Gly His Pro Gly Pro Ser Glu Pro Ala Asp
            2115                2120                2125

Gln Lys Leu Ser Ala Val Gly Glu Lys Gln Thr Leu Ser Pro Lys His
        2130                2135                2140

Pro Lys Pro Ser Thr Val Lys Asp Cys Pro Thr Leu Cys Lys Gln Thr
2145                2150                2155                2160

Asp Asn Arg Gln Thr Asp Lys Ser Pro Ser Gln Pro Ala Ala Asn Thr
            2165                2170                2175

Asp Arg Arg Ala Glu Gly Lys Lys Cys Thr Glu Ala Leu Tyr Ala Pro
            2180                2185                2190

Ala Glu Gly Asp Lys Leu Glu Ala Gly Leu Ser Phe Val His Ser Glu
        2195                2200                2205

Asn Arg Leu Lys Gly Ala Glu Arg Pro Ala Ala Gly Val Gly Lys Gly
        2210                2215                2220

Phe Pro Glu Ala Arg Gly Lys Gly Pro Gly Pro Gln Lys Pro Pro Thr
2225                2230                2235                2240

Glu Ala Asp Lys Pro Asn Gly Met Lys Arg Ser Pro Ser Ala Thr Gly
            2245                2250                2255

Gln Ser Ser Phe Arg Ser Thr Ala Leu Pro Glu Lys Ser Leu Ser Cys
        2260                2265                2270

Ser Ser Ser Phe Pro Glu Thr Arg Ala Gly Val Arg Glu Ala Ser Ala
        2275                2280                2285

Ala Ser Ser Asp Thr Ser Ser Ala Lys Ala Ala Gly Gly Met Leu Glu
        2290                2295                2300

Leu Pro Ala Pro Ser Asn Arg Asp His Arg Lys Ala Gln Pro Ala Gly
2305                2310                2315                2320

Glu Gly Arg Thr His Met Thr Lys Ser Asp Ser Leu Pro Ser Phe Arg
        2325                2330                2335

Val Ser Thr Leu Pro Leu Glu Ser His His Pro Asp Pro Asn Thr Met
            2340                2345                2350

Gly Gly Ala Ser His Arg Asp Arg Ala Leu Ser Val Thr Ala Thr Val
        2355                2360                2365

Gly Glu Thr Lys Gly Lys Asp Pro Ala Pro Ala Gln Pro Pro Pro Ala
    2370                2375                2380

Arg Lys Gln Asn Val Gly Arg Asp Val Thr Lys Pro Ser Pro Ala Pro
2385                2390                2395                2400

Asn Thr Asp Arg Pro Ile Ser Leu Ser Asn Glu Lys Asp Phe Val Val
            2405                2410                2415
```

Arg Gln Arg Arg Gly Lys Glu Ser Leu Arg Ser Ser Pro His Lys Lys
            2420                2425                2430

Ala Leu

<210> SEQ ID NO 2
<211> LENGTH: 250
<212> TYPE: PRT
<213> ORGANISM: Homo sapiens

<400> SEQUENCE: 2

Met Gly Glu Lys Val Ser Glu Ala Pro Glu Pro Val Pro Arg Gly Cys
1               5                   10                  15

Ser Gly His Gly Ser Arg Thr Pro Ala Ser Ala Leu Val Ala Ala Ser
            20                  25                  30

Ser Pro Gly Ala Ser Ser Ala Glu Ser Ser Ser Gly Ser Glu Thr Leu
        35                  40                  45

Ser Glu Glu Gly Glu Pro Gly Gly Phe Ser Arg Glu His Gln Pro Pro
    50                  55                  60

Pro Pro Pro Pro Leu Gly Gly Thr Leu Gly Ala Arg Ala Pro Ala Ala
65                  70                  75                  80

Trp Ala Pro Ala Ser Val Leu Leu Glu Arg Gly Val Leu Ala Leu Pro
                85                  90                  95

Pro Pro Leu Pro Gly Gly Ala Val Pro Pro Ala Pro Arg Gly Ser Ser
            100                 105                 110

Ala Ser Gln Glu Glu Gln Asp Glu Leu Asp His Ile Leu Ser Pro
        115                 120                 125

Pro Pro Met Pro Phe Arg Lys Cys Ser Asn Pro Asp Val Ala Ser Gly
    130                 135                 140

Pro Gly Lys Ser Leu Lys Tyr Lys Arg Gln Leu Ser Glu Asp Gly Arg
145                 150                 155                 160

Gln Leu Arg Arg Gly Ser Leu Gly Gly Ala Leu Thr Gly Arg Tyr Leu
                165                 170                 175

Leu Pro Asn Pro Val Ala Gly Gln Ala Trp Pro Ala Ser Ala Glu Thr
            180                 185                 190

Ser Asn Leu Val Arg Met Arg Ser Gln Ala Leu Gly Gln Ser Ala Pro
        195                 200                 205

Ser Leu Thr Ala Ser Leu Lys Glu Leu Ser Leu Pro Arg Arg Gly Ser
    210                 215                 220

Leu Ile Asp Ser Gln Lys Trp Asn Cys Leu Val Lys Arg Pro Val Cys
225                 230                 235                 240

Pro Asn Ala Gly Arg Thr Ser Pro Leu Gly
                245                 250

<210> SEQ ID NO 3
<211> LENGTH: 2623
<212> TYPE: PRT
<213> ORGANISM: Homo sapiens

<400> SEQUENCE: 3

Met Gly Glu Lys Val Ser Glu Ala Pro Glu Pro Val Pro Arg Gly Cys
1               5                   10                  15

Ser Gly His Gly Ser Arg Thr Pro Ala Ser Ala Leu Val Ala Ala Ser
            20                  25                  30

Ser Pro Gly Ala Ser Ser Ala Glu Ser Ser Ser Gly Ser Glu Thr Leu
        35                  40                  45

```
Ser Glu Gly Glu Pro Gly Gly Phe Ser Arg Glu His Gln Pro Pro
 50              55                  60

Pro Pro Pro Pro Leu Gly Gly Thr Leu Gly Ala Arg Ala Pro Ala Ala
 65              70                  75                  80

Trp Ala Pro Ala Ser Val Leu Leu Glu Arg Gly Val Leu Ala Leu Pro
                 85                  90                  95

Pro Pro Leu Pro Gly Gly Ala Val Pro Pro Ala Pro Arg Gly Ser Ser
                100                 105                 110

Ala Ser Gln Glu Glu Gln Asp Glu Glu Leu Asp His Ile Leu Ser Pro
            115                 120                 125

Pro Pro Met Pro Phe Arg Lys Cys Ser Asn Pro Asp Val Ala Ser Gly
130                 135                 140

Pro Gly Lys Ser Leu Lys Tyr Lys Arg Gln Leu Ser Glu Asp Gly Arg
145                 150                 155                 160

Gln Leu Arg Arg Gly Ser Leu Gly Gly Ala Leu Thr Gly Arg Tyr Leu
                165                 170                 175

Leu Pro Asn Pro Val Ala Gly Gln Ala Trp Pro Ala Ser Ala Glu Thr
            180                 185                 190

Ser Asn Leu Val Arg Met Arg Ser Gln Ala Leu Gly Gln Ser Ala Pro
            195                 200                 205

Ser Leu Thr Ala Ser Leu Lys Glu Leu Ser Leu Pro Arg Arg Gly Ser
210                 215                 220

Phe Cys Arg Thr Ser Asn Arg Lys Ser Leu Ile Gly Asn Gly Gln Ser
225                 230                 235                 240

Pro Ala Leu Pro Arg Pro His Ser Pro Leu Ser Ala His Ala Gly Asn
                245                 250                 255

Ser Pro Gln Asp Ser Pro Arg Asn Phe Ser Pro Ser Ala Ser Ala His
            260                 265                 270

Phe Ser Phe Ala Arg Arg Thr Asp Gly Arg Arg Trp Ser Leu Ala Ser
            275                 280                 285

Leu Pro Ser Ser Gly Tyr Gly Thr Asn Thr Pro Ser Ser Thr Val Ser
290                 295                 300

Ser Ser Cys Ser Ser Gln Glu Lys Leu His Gln Leu Pro Tyr Gln Pro
305                 310                 315                 320

Thr Pro Asp Glu Leu His Phe Leu Ser Lys His Phe Cys Thr Thr Glu
                325                 330                 335

Ser Ile Ala Thr Glu Asn Arg Cys Arg Asn Thr Pro Met Arg Pro Arg
            340                 345                 350

Ser Arg Ser Leu Ser Pro Gly Arg Ser Pro Ala Cys Cys Asp His Glu
            355                 360                 365

Ile Ile Met Met Asn His Val Tyr Lys Glu Arg Phe Pro Lys Ala Thr
370                 375                 380

Ala Gln Met Glu Glu Arg Leu Lys Glu Ile Ile Thr Ser Tyr Ser Pro
385                 390                 395                 400

Asp Asn Val Leu Pro Leu Ala Asp Gly Val Leu Ser Phe Thr His His
                405                 410                 415

Gln Ile Ile Glu Leu Ala Arg Asp Cys Leu Asp Lys Ser His Gln Gly
            420                 425                 430

Leu Ile Thr Ser Arg Tyr Phe Leu Glu Leu Gln His Lys Leu Asp Lys
            435                 440                 445

Leu Leu Gln Glu Ala His Asp Arg Ser Glu Ser Gly Glu Leu Ala Phe
450                 455                 460
```

```
Ile Lys Gln Leu Val Arg Lys Ile Leu Ile Val Ala Arg Pro Ala
465                 470                 475                 480

Arg Leu Leu Glu Cys Leu Glu Phe Asp Pro Glu Glu Phe Tyr Tyr Leu
                485                 490                 495

Leu Glu Ala Ala Glu Gly His Ala Lys Glu Gly Gln Gly Ile Lys Thr
            500                 505                 510

Asp Ile Pro Arg Tyr Ile Ile Ser Gln Leu Gly Leu Asn Lys Asp Pro
            515                 520                 525

Leu Glu Glu Met Ala His Leu Gly Asn Tyr Asp Ser Gly Thr Ala Glu
            530                 535                 540

Thr Pro Glu Thr Asp Glu Ser Val Ser Ser Asn Ala Ser Leu Lys
545                 550                 555                 560

Leu Arg Arg Lys Pro Arg Glu Ser Asp Phe Glu Thr Ile Lys Leu Ile
                565                 570                 575

Ser Asn Gly Ala Tyr Gly Ala Val Tyr Phe Val Arg His Lys Glu Ser
                580                 585                 590

Arg Gln Arg Phe Ala Met Lys Lys Ile Asn Lys Gln Asn Leu Ile Leu
            595                 600                 605

Arg Asn Gln Ile Gln Gln Ala Phe Val Glu Arg Asp Ile Leu Thr Phe
            610                 615                 620

Ala Glu Asn Pro Phe Val Val Ser Met Tyr Cys Ser Phe Glu Thr Arg
625                 630                 635                 640

Arg His Leu Cys Met Val Met Glu Tyr Val Glu Gly Gly Asp Cys Ala
                645                 650                 655

Thr Leu Met Lys Asn Met Gly Pro Leu Pro Val Asp Met Ala Arg Met
                660                 665                 670

Tyr Phe Ala Glu Thr Val Leu Ala Leu Glu Tyr Leu His Asn Tyr Gly
            675                 680                 685

Ile Val His Arg Asp Leu Lys Pro Asp Asn Leu Leu Val Thr Ser Met
            690                 695                 700

Gly His Ile Lys Leu Thr Asp Phe Gly Leu Ser Lys Val Gly Leu Met
705                 710                 715                 720

Ser Met Thr Thr Asn Leu Tyr Glu Gly His Ile Glu Lys Asp Ala Arg
                725                 730                 735

Glu Phe Leu Asp Lys Gln Val Cys Gly Thr Pro Glu Tyr Ile Ala Pro
            740                 745                 750

Glu Val Ile Leu Arg Gln Gly Tyr Gly Lys Pro Val Asp Trp Trp Ala
            755                 760                 765

Met Gly Ile Ile Leu Tyr Glu Phe Leu Val Gly Cys Val Pro Phe Phe
770                 775                 780

Gly Asp Thr Pro Glu Glu Leu Phe Gly Gln Val Ile Ser Asp Glu Ile
785                 790                 795                 800

Asn Trp Pro Glu Lys Asp Glu Ala Pro Pro Asp Ala Gln Asp Leu
                805                 810                 815

Ile Thr Leu Leu Leu Arg Gln Asn Pro Leu Glu Arg Leu Gly Thr Gly
            820                 825                 830

Gly Ala Tyr Glu Val Lys Gln His Arg Phe Phe Arg Ser Leu Asp Trp
            835                 840                 845

Asn Ser Leu Leu Arg Gln Lys Ala Glu Phe Ile Pro Gln Leu Glu Ser
            850                 855                 860

Glu Asp Asp Thr Ser Tyr Phe Asp Thr Arg Ser Glu Lys Tyr His His
865                 870                 875                 880
```

```
Met Glu Thr Glu Glu Glu Asp Asp Thr Asn Asp Glu Asp Phe Asn Val
                885                 890                 895

Glu Ile Arg Gln Phe Ser Ser Cys Ser His Arg Phe Ser Lys Val Phe
        900                 905                 910

Ser Ser Ile Asp Arg Ile Thr Gln Asn Ser Ala Glu Glu Lys Glu Asp
            915                 920                 925

Ser Val Asp Lys Thr Lys Ser Thr Thr Leu Pro Ser Thr Glu Thr Leu
930                 935                 940

Ser Trp Ser Ser Glu Tyr Ser Glu Met Gln Gln Leu Ser Thr Ser Asn
945                 950                 955                 960

Ser Ser Asp Thr Glu Ser Asn Arg His Lys Leu Ser Ser Gly Leu Leu
                965                 970                 975

Pro Lys Leu Ala Ile Ser Thr Glu Gly Glu Gln Asp Glu Ala Ala Ser
            980                 985                 990

Cys Pro Gly Asp Pro His Glu Glu Pro Gly Lys Pro Ala Leu Pro Pro
        995                 1000                1005

Glu Glu Cys Ala Gln Glu Glu Pro Glu Val Thr Thr Pro Ala Ser Thr
    1010                1015                1020

Ile Ser Ser Ser Thr Leu Ser Val Gly Ser Phe Ser Glu His Leu Asp
1025                1030                1035                1040

Gln Ile Asn Gly Arg Ser Glu Cys Val Asp Ser Thr Asp Asn Ser Ser
                1045                1050                1055

Lys Pro Ser Ser Glu Pro Ala Ser His Met Ala Arg Gln Arg Leu Glu
            1060                1065                1070

Ser Thr Glu Lys Lys Lys Ile Ser Gly Lys Val Thr Lys Ser Leu Ser
        1075                1080                1085

Ala Ser Ala Leu Ser Leu Met Ile Pro Gly Asp Met Phe Ala Val Ser
    1090                1095                1100

Pro Leu Gly Ser Pro Met Ser Pro His Ser Leu Ser Ser Asp Pro Ser
1105                1110                1115                1120

Ser Ser Arg Asp Ser Ser Pro Ser Arg Asp Ser Ser Ala Ala Ser Ala
                1125                1130                1135

Ser Pro His Gln Pro Ile Val Ile His Ser Ser Gly Lys Asn Tyr Gly
            1140                1145                1150

Phe Thr Ile Arg Ala Ile Arg Val Tyr Val Gly Asp Ser Asp Ile Tyr
        1155                1160                1165

Thr Val His His Ile Val Trp Asn Val Glu Glu Gly Ser Pro Ala Cys
    1170                1175                1180

Gln Ala Gly Leu Lys Ala Gly Asp Leu Ile Thr His Ile Asn Gly Glu
1185                1190                1195                1200

Pro Val His Gly Leu Val His Thr Glu Val Ile Glu Leu Leu Leu Lys
                1205                1210                1215

Ser Gly Asn Lys Val Ser Ile Thr Thr Thr Pro Phe Glu Asn Thr Ser
            1220                1225                1230

Ile Lys Thr Gly Pro Ala Arg Arg Asn Ser Tyr Lys Ser Arg Met Val
        1235                1240                1245

Arg Arg Ser Lys Lys Ser Lys Lys Lys Glu Ser Leu Glu Arg Arg
    1250                1255                1260

Ser Leu Phe Lys Lys Leu Ala Lys Gln Pro Ser Pro Leu Leu His Thr
1265                1270                1275                1280

Ser Arg Ser Phe Ser Cys Leu Asn Arg Ser Leu Ser Ser Gly Glu Ser
                1285                1290                1295
```

```
Leu Pro Gly Ser Pro Thr His Ser Leu Ser Pro Arg Ser Pro Thr Pro
        1300                1305                1310

Ser Tyr Arg Ser Thr Pro Asp Phe Pro Ser Gly Thr Asn Ser Ser Gln
    1315                1320                1325

Ser Ser Ser Pro Ser Ser Ser Ala Pro Asn Ser Pro Ala Gly Ser Gly
    1330                1335                1340

His Ile Arg Pro Ser Thr Leu His Gly Leu Ala Pro Lys Leu Gly Gly
1345                1350                1355                1360

Gln Arg Tyr Arg Ser Gly Arg Arg Lys Ser Ala Gly Asn Ile Pro Leu
        1365                1370                1375

Ser Pro Leu Ala Arg Thr Pro Ser Pro Thr Pro Gln Pro Thr Ser Pro
    1380                1385                1390

Gln Arg Ser Pro Ser Pro Leu Leu Gly His Ser Leu Gly Asn Ser Lys
    1395                1400                1405

Ile Ala Gln Ala Phe Pro Ser Lys Met His Ser Pro Pro Thr Ile Val
    1410                1415                1420

Arg His Ile Val Arg Pro Lys Ser Ala Glu Pro Pro Arg Ser Pro Leu
1425                1430                1435                1440

Leu Lys Arg Val Gln Ser Glu Glu Lys Leu Ser Pro Ser Tyr Gly Ser
        1445                1450                1455

Asp Lys Lys His Leu Cys Ser Arg Lys His Ser Leu Glu Val Thr Gln
        1460                1465                1470

Glu Glu Val Gln Arg Glu Gln Ser Gln Arg Glu Ala Pro Leu Gln Ser
        1475                1480                1485

Leu Asp Glu Asn Val Cys Asp Val Pro Pro Leu Ser Arg Ala Arg Pro
    1490                1495                1500

Val Glu Gln Gly Cys Leu Lys Arg Pro Val Ser Arg Lys Val Gly Arg
1505                1510                1515                1520

Gln Glu Ser Val Asp Asp Leu Asp Arg Asp Lys Leu Lys Ala Lys Val
        1525                1530                1535

Val Val Lys Lys Ala Asp Gly Phe Pro Glu Lys Gln Glu Ser His Gln
    1540                1545                1550

Lys Ser His Gly Pro Gly Ser Asp Leu Glu Asn Phe Ala Leu Phe Lys
    1555                1560                1565

Leu Glu Glu Arg Glu Lys Lys Val Tyr Pro Lys Ala Val Glu Arg Ser
    1570                1575                1580

Ser Thr Phe Glu Asn Lys Ala Ser Met Gln Glu Ala Pro Pro Leu Gly
1585                1590                1595                1600

Ser Leu Leu Lys Asp Ala Leu His Lys Gln Ala Ser Val Arg Ala Ser
        1605                1610                1615

Glu Gly Ala Met Ser Asp Gly Arg Val Pro Ala Glu His Arg Gln Gly
        1620                1625                1630

Gly Gly Asp Phe Arg Arg Ala Pro Ala Pro Gly Thr Leu Gln Asp Gly
    1635                1640                1645

Leu Cys His Ser Leu Asp Arg Gly Ile Ser Gly Lys Gly Glu Gly Thr
    1650                1655                1660

Glu Lys Ser Ser Gln Ala Lys Glu Leu Leu Arg Cys Glu Lys Leu Asp
1665                1670                1675                1680

Ser Lys Leu Ala Asn Ile Asp Tyr Leu Arg Lys Lys Met Ser Leu Glu
        1685                1690                1695

Asp Lys Glu Asp Asn Leu Cys Pro Val Leu Lys Pro Lys Met Thr Ala
    1700                1705                1710
```

```
Gly Ser His Glu Cys Leu Pro Gly Asn Pro Val Arg Pro Thr Gly Gly
        1715                1720                1725

Gln Gln Glu Pro Pro Pro Ala Ser Glu Ser Arg Ala Phe Val Ser Ser
    1730                1735                1740

Thr His Ala Ala Gln Met Ser Ala Val Ser Phe Val Pro Leu Lys Ala
1745                1750                1755                1760

Leu Thr Gly Arg Val Asp Ser Gly Thr Glu Lys Pro Gly Leu Val Ala
            1765                1770                1775

Pro Glu Ser Pro Val Arg Lys Ser Pro Ser Glu Tyr Lys Leu Glu Gly
        1780                1785                1790

Arg Ser Val Ser Cys Leu Lys Pro Ile Glu Gly Thr Leu Asp Ile Ala
    1795                1800                1805

Leu Leu Ser Gly Pro Gln Ala Ser Lys Thr Glu Leu Pro Ser Pro Glu
1810                1815                1820

Ser Ala Gln Ser Pro Ser Pro Ser Gly Asp Val Arg Ala Ser Val Pro
1825                1830                1835                1840

Pro Val Leu Pro Ser Ser Ser Gly Lys Lys Asn Asp Thr Thr Ser Ala
            1845                1850                1855

Arg Glu Leu Ser Pro Ser Ser Leu Lys Met Asn Lys Ser Tyr Leu Leu
        1860                1865                1870

Glu Pro Trp Phe Leu Pro Pro Ser Arg Gly Leu Gln Asn Ser Pro Ala
    1875                1880                1885

Val Ser Leu Pro Asp Pro Glu Phe Lys Arg Asp Arg Lys Gly Pro His
    1890                1895                1900

Pro Thr Ala Arg Ser Pro Gly Thr Val Met Glu Ser Asn Pro Gln Gln
1905                1910                1915                1920

Arg Glu Gly Ser Ser Pro Lys His Gln Asp His Thr Thr Asp Pro Lys
            1925                1930                1935

Leu Leu Thr Cys Leu Gly Gln Asn Leu His Ser Pro Asp Leu Ala Arg
        1940                1945                1950

Pro Arg Cys Pro Leu Pro Pro Glu Ala Ser Pro Ser Arg Glu Lys Pro
    1955                1960                1965

Gly Leu Arg Glu Ser Ser Glu Arg Gly Pro Pro Thr Ala Arg Ser Glu
    1970                1975                1980

Arg Ser Ala Ala Arg Ala Asp Thr Cys Arg Glu Pro Ser Met Glu Leu
1985                1990                1995                2000

Cys Phe Pro Glu Thr Ala Lys Thr Ser Asp Asn Ser Lys Asn Leu Leu
            2005                2010                2015

Ser Val Gly Arg Thr His Pro Asp Phe Tyr Thr Gln Thr Gln Ala Met
        2020                2025                2030

Glu Lys Ala Trp Ala Pro Gly Gly Lys Thr Asn His Lys Asp Gly Pro
    2035                2040                2045

Gly Glu Ala Arg Pro Pro Arg Asp Asn Ser Ser Leu His Ser Ala
    2050                2055                2060

Gly Ile Pro Cys Glu Lys Glu Leu Gly Lys Val Arg Arg Gly Val Glu
2065                2070                2075                2080

Pro Lys Pro Glu Ala Leu Leu Ala Arg Arg Ser Leu Gln Pro Pro Gly
            2085                2090                2095

Ile Glu Ser Glu Lys Ser Glu Lys Leu Ser Ser Phe Pro Ser Leu Gln
        2100                2105                2110

Lys Asp Gly Ala Lys Glu Pro Glu Arg Lys Glu Gln Pro Leu Gln Arg
    2115                2120                2125
```

```
His Pro Ser Ser Ile Pro Pro Pro Leu Thr Ala Lys Asp Leu Ser
    2130            2135            2140

Ser Pro Ala Ala Arg Gln His Cys Ser Ser Pro Ser His Ala Ser Gly
2145            2150            2155            2160

Arg Glu Pro Gly Ala Lys Pro Ser Thr Ala Glu Pro Ser Ser Ser Pro
            2165            2170            2175

Gln Asp Pro Pro Lys Pro Val Ala Ala His Ser Glu Ser Ser Ser His
        2180            2185            2190

Lys Pro Arg Pro Gly Pro Asp Pro Gly Pro Lys Thr Lys His Pro
    2195            2200            2205

Asp Arg Ser Leu Ser Ser Gln Lys Pro Ser Val Gly Ala Thr Lys Gly
    2210            2215            2220

Lys Glu Pro Ala Thr Gln Ser Leu Gly Gly Ser Ser Arg Glu Gly Lys
2225            2230            2235            2240

Gly His Ser Lys Ser Gly Pro Asp Val Phe Pro Ala Thr Pro Gly Ser
            2245            2250            2255

Gln Asn Lys Ala Ser Asp Gly Ile Gly Gln Gly Glu Gly Gly Pro Ser
            2260            2265            2270

Val Pro Leu His Thr Asp Arg Ala Pro Leu Asp Ala Lys Pro Gln Pro
    2275            2280            2285

Thr Ser Gly Gly Arg Pro Leu Glu Val Leu Glu Lys Pro Val His Leu
    2290            2295            2300

Pro Arg Pro Gly His Pro Gly Pro Ser Glu Pro Ala Asp Gln Lys Leu
2305            2310            2315            2320

Ser Ala Val Gly Glu Lys Gln Thr Leu Ser Pro Lys His Pro Lys Pro
            2325            2330            2335

Ser Thr Val Lys Asp Cys Pro Thr Leu Cys Lys Gln Thr Asp Asn Arg
            2340            2345            2350

Gln Thr Asp Lys Ser Pro Ser Gln Pro Ala Ala Asn Thr Asp Arg Arg
        2355            2360            2365

Ala Glu Gly Lys Lys Cys Thr Glu Ala Leu Tyr Ala Pro Ala Glu Gly
    2370            2375            2380

Asp Lys Leu Glu Ala Gly Leu Ser Phe Val His Ser Glu Asn Arg Leu
2385            2390            2395            2400

Lys Gly Ala Glu Arg Pro Ala Ala Gly Val Gly Lys Gly Phe Pro Glu
            2405            2410            2415

Ala Arg Gly Lys Gly Pro Gly Pro Gln Lys Pro Pro Thr Glu Ala Asp
            2420            2425            2430

Lys Pro Asn Gly Met Lys Arg Ser Pro Ser Ala Thr Gly Gln Ser Ser
        2435            2440            2445

Phe Arg Ser Thr Ala Leu Pro Glu Lys Ser Leu Ser Cys Ser Ser Ser
    2450            2455            2460

Phe Pro Glu Thr Arg Ala Gly Val Arg Glu Ala Ser Ala Ala Ser Ser
2465            2470            2475            2480

Asp Thr Ser Ser Ala Lys Ala Ala Gly Gly Met Leu Glu Leu Pro Ala
            2485            2490            2495

Pro Ser Asn Arg Asp His Arg Lys Ala Gln Pro Ala Gly Glu Gly Arg
            2500            2505            2510

Thr His Met Thr Lys Ser Asp Ser Leu Pro Ser Phe Arg Val Ser Thr
        2515            2520            2525

Leu Pro Leu Glu Ser His His Pro Asp Pro Asn Thr Met Gly Gly Ala
    2530            2535            2540
```

Ser His Arg Asp Arg Ala Leu Ser Val Thr Ala Thr Val Gly Glu Thr
2545                2550                2555                2560

Lys Gly Lys Asp Pro Ala Pro Ala Gln Pro Pro Ala Arg Lys Gln
        2565                2570                2575

Asn Val Gly Arg Asp Val Thr Lys Pro Ser Pro Ala Pro Asn Thr Asp
            2580                2585                2590

Arg Pro Ile Ser Leu Ser Asn Glu Lys Asp Phe Val Val Arg Gln Arg
        2595                2600                2605

Arg Gly Lys Glu Ser Leu Arg Ser Ser Pro His Lys Lys Ala Leu
    2610                2615                2620

<210> SEQ ID NO 4
<211> LENGTH: 2417
<212> TYPE: PRT
<213> ORGANISM: Homo sapiens

<400> SEQUENCE: 4

Met Lys Ala Gln Arg Glu Arg Leu Gln Ile Pro Gly Leu Thr Leu Asp
1               5                   10                  15

Cys Arg Thr Ser Asn Arg Lys Ser Leu Ile Gly Asn Gly Gln Ser Pro
            20                  25                  30

Ala Leu Pro Arg Pro His Ser Pro Leu Ser Ala His Ala Gly Asn Ser
        35                  40                  45

Pro Gln Asp Ser Pro Arg Asn Phe Ser Pro Ser Ala Ser Ala His Phe
    50                  55                  60

Ser Phe Ala Arg Arg Asn Asp Arg Thr Asp Gly Arg Arg Trp Ser Leu
65                  70                  75                  80

Ala Ser Leu Pro Ser Ser Gly Tyr Gly Thr Asn Thr Pro Ser Ser Thr
                85                  90                  95

Val Ser Ser Cys Ser Ser Gln Glu Lys Leu His Gln Leu Pro Tyr
            100                 105                 110

Gln Pro Thr Pro Asp Glu Leu His Phe Leu Ser Lys His Phe Cys Thr
        115                 120                 125

Thr Glu Ser Ile Ala Thr Glu Asn Arg Cys Arg Asn Thr Pro Met Arg
130                 135                 140

Pro Arg Ser Arg Ser Leu Ser Pro Gly Arg Ser Pro Ala Cys Cys Asp
145                 150                 155                 160

His Glu Ile Ile Met Met Asn His Val Tyr Lys Glu Arg Phe Pro Lys
                165                 170                 175

Ala Thr Ala Gln Met Glu Glu Arg Leu Lys Glu Ile Ile Thr Ser Tyr
            180                 185                 190

Ser Pro Asp Asn Val Leu Pro Leu Ala Asp Gly Val Leu Ser Phe Thr
        195                 200                 205

His His Gln Ile Ile Glu Leu Ala Arg Asp Cys Leu Asp Lys Ser His
    210                 215                 220

Gln Gly Leu Ile Thr Ser Arg Tyr Phe Leu Glu Leu Gln His Lys Leu
225                 230                 235                 240

Asp Lys Leu Leu Gln Glu Ala His Asp Arg Ser Glu Ser Gly Glu Leu
                245                 250                 255

Ala Phe Ile Lys Gln Leu Val Arg Lys Ile Leu Ile Val Ile Ala Arg
            260                 265                 270

Pro Ala Arg Leu Leu Glu Cys Leu Glu Phe Asp Pro Glu Glu Phe Tyr
        275                 280                 285

Tyr Leu Leu Glu Ala Ala Glu Gly His Ala Lys Glu Gly Gln Gly Ile
    290                 295                 300

```
Lys Thr Asp Ile Pro Arg Tyr Ile Ile Ser Gln Leu Gly Leu Asn Lys
305                 310                 315                 320

Asp Pro Leu Glu Glu Met Ala His Leu Gly Asn Tyr Asp Ser Gly Thr
            325                 330                 335

Ala Glu Thr Pro Glu Thr Asp Glu Ser Val Ser Ser Asn Ala Ser
            340                 345                 350

Leu Lys Leu Arg Arg Lys Pro Arg Glu Ser Asp Phe Glu Thr Ile Lys
            355                 360                 365

Leu Ile Ser Asn Gly Ala Tyr Gly Ala Val Tyr Phe Val Arg His Lys
            370                 375                 380

Glu Ser Arg Gln Arg Phe Ala Met Lys Lys Ile Asn Lys Gln Asn Leu
385                 390                 395                 400

Ile Leu Arg Asn Gln Ile Gln Gln Ala Phe Val Glu Arg Asp Ile Leu
            405                 410                 415

Thr Phe Ala Glu Asn Pro Phe Val Val Ser Met Tyr Cys Ser Phe Glu
            420                 425                 430

Thr Arg Arg His Leu Cys Met Val Met Glu Tyr Val Glu Gly Gly Asp
            435                 440                 445

Cys Ala Thr Leu Met Lys Asn Met Gly Pro Leu Pro Val Asp Met Ala
450                 455                 460

Arg Met Tyr Phe Ala Glu Thr Val Leu Ala Leu Glu Tyr Leu His Asn
465                 470                 475                 480

Tyr Gly Ile Val His Arg Asp Leu Lys Pro Asp Asn Leu Leu Val Thr
            485                 490                 495

Ser Met Gly His Ile Lys Leu Thr Asp Phe Gly Leu Ser Lys Val Gly
            500                 505                 510

Leu Met Ser Met Thr Thr Asn Leu Tyr Glu Gly His Ile Glu Lys Asp
            515                 520                 525

Ala Arg Glu Phe Leu Asp Lys Gln Val Cys Gly Thr Pro Glu Tyr Ile
            530                 535                 540

Ala Pro Glu Val Ile Leu Arg Gln Gly Tyr Gly Lys Pro Val Asp Trp
545                 550                 555                 560

Trp Ala Met Gly Ile Ile Leu Tyr Glu Phe Leu Val Gly Cys Val Pro
            565                 570                 575

Phe Phe Gly Asp Thr Pro Glu Glu Leu Phe Gly Gln Val Ile Ser Asp
            580                 585                 590

Glu Ile Asn Trp Pro Glu Lys Asp Glu Ala Pro Pro Asp Ala Gln
            595                 600                 605

Asp Leu Ile Thr Leu Leu Leu Arg Gln Asn Pro Leu Glu Arg Leu Gly
610                 615                 620

Thr Gly Gly Ala Tyr Glu Val Lys Gln His Arg Phe Phe Arg Ser Leu
625                 630                 635                 640

Asp Trp Asn Ser Leu Leu Arg Gln Lys Ala Glu Phe Ile Pro Gln Leu
            645                 650                 655

Glu Ser Glu Asp Asp Thr Ser Tyr Phe Asp Thr Arg Ser Glu Lys Tyr
            660                 665                 670

His His Met Glu Thr Glu Glu Asp Thr Asn Asp Glu Asp Phe
            675                 680                 685

Asn Val Glu Ile Arg Gln Phe Ser Ser Cys Ser His Arg Phe Ser Lys
            690                 695                 700

Val Phe Ser Ser Ile Asp Arg Ile Thr Gln Asn Ser Ala Glu Glu Lys
705                 710                 715                 720
```

```
Glu Asp Ser Val Asp Lys Thr Lys Ser Thr Thr Leu Pro Ser Thr Glu
                725                 730                 735

Thr Leu Ser Trp Ser Ser Glu Tyr Ser Glu Met Gln Gln Leu Ser Thr
        740                 745                 750

Ser Asn Ser Ser Asp Thr Glu Ser Asn Arg His Lys Leu Ser Ser Gly
            755                 760                 765

Leu Leu Pro Lys Leu Ala Ile Ser Thr Glu Gly Gln Asp Glu Ala
        770                 775                 780

Ala Ser Cys Pro Gly Asp Pro His Glu Glu Pro Gly Lys Pro Ala Leu
785                 790                 795                 800

Pro Pro Glu Glu Cys Ala Gln Glu Glu Pro Glu Val Thr Thr Pro Ala
                805                 810                 815

Ser Thr Ile Ser Ser Ser Thr Leu Ser Val Gly Ser Phe Ser Glu His
                820                 825                 830

Leu Asp Gln Ile Asn Gly Arg Ser Glu Cys Val Asp Ser Thr Asp Asn
                835                 840                 845

Ser Ser Lys Pro Ser Ser Glu Pro Ala Ser His Met Ala Arg Gln Arg
        850                 855                 860

Leu Glu Ser Thr Glu Lys Lys Lys Ile Ser Gly Lys Val Thr Lys Ser
865                 870                 875                 880

Leu Ser Ala Ser Ala Leu Ser Leu Met Ile Pro Gly Asp Met Phe Ala
                885                 890                 895

Val Ser Pro Leu Gly Ser Pro Met Ser Pro His Ser Leu Ser Ser Asp
            900                 905                 910

Pro Ser Ser Ser Arg Asp Ser Pro Ser Arg Asp Ser Ser Ala Ala
        915                 920                 925

Ser Ala Ser Pro His Gln Pro Ile Val Ile His Ser Ser Gly Lys Asn
    930                 935                 940

Tyr Gly Phe Thr Ile Arg Ala Ile Arg Val Tyr Val Gly Asp Ser Asp
945                 950                 955                 960

Ile Tyr Thr Val His His Ile Val Trp Asn Val Glu Glu Gly Ser Pro
                965                 970                 975

Ala Cys Gln Ala Gly Leu Lys Ala Gly Asp Leu Ile Thr His Ile Asn
                980                 985                 990

Gly Glu Pro Val His Gly Leu Val His Thr Glu Val Ile Glu Leu Leu
            995                 1000                1005

Leu Lys Ser Gly Asn Lys Val Ser Ile Thr Thr Thr Pro Phe Glu Asn
        1010                1015                1020

Thr Ser Ile Lys Thr Gly Pro Ala Arg Arg Asn Ser Tyr Lys Ser Arg
1025                1030                1035                1040

Met Val Arg Arg Ser Lys Lys Ser Lys Lys Lys Glu Ser Leu Glu Arg
                1045                1050                1055

Arg Arg Ser Leu Phe Lys Lys Leu Ala Lys Gln Pro Ser Pro Leu Leu
            1060                1065                1070

His Thr Ser Arg Ser Phe Ser Cys Leu Asn Arg Ser Leu Ser Ser Gly
        1075                1080                1085

Glu Ser Leu Pro Gly Ser Pro Thr His Ser Leu Ser Pro Arg Ser Pro
    1090                1095                1100

Thr Pro Ser Tyr Arg Ser Thr Pro Asp Phe Pro Ser Gly Thr Asn Ser
1105                1110                1115                1120

Ser Gln Ser Ser Ser Pro Ser Ser Ala Pro Asn Ser Pro Ala Gly
        1125                1130                1135
```

```
Ser Gly His Ile Arg Pro Ser Thr Leu His Gly Leu Ala Pro Lys Leu
        1140                1145                1150

Gly Gly Gln Arg Tyr Arg Ser Gly Arg Lys Ser Ala Gly Asn Ile
    1155                1160                1165

Pro Leu Ser Pro Leu Ala Arg Thr Pro Ser Pro Thr Pro Gln Pro Thr
    1170                1175                1180

Ser Pro Gln Arg Ser Pro Ser Pro Leu Leu Gly His Ser Leu Gly Asn
1185                1190                1195                1200

Ser Lys Ile Ala Gln Ala Phe Pro Ser Lys Met His Ser Pro Pro Thr
                1205                1210                1215

Ile Val Arg His Ile Val Arg Pro Lys Ser Ala Glu Pro Pro Arg Ser
        1220                1225                1230

Pro Leu Leu Lys Arg Val Gln Ser Glu Glu Lys Leu Ser Pro Ser Tyr
        1235                1240                1245

Gly Ser Asp Lys Lys His Leu Cys Ser Arg Lys His Ser Leu Glu Val
    1250                1255                1260

Thr Gln Glu Glu Val Gln Arg Glu Gln Ser Gln Arg Glu Ala Pro Leu
1265                1270                1275                1280

Gln Ser Leu Asp Glu Asn Val Cys Asp Val Pro Pro Leu Ser Arg Ala
        1285                1290                1295

Arg Pro Val Glu Gln Gly Cys Leu Lys Arg Pro Val Ser Arg Lys Val
        1300                1305                1310

Gly Arg Gln Glu Ser Val Asp Asp Leu Asp Arg Asp Lys Leu Lys Ala
        1315                1320                1325

Lys Val Val Val Lys Lys Ala Asp Gly Phe Pro Glu Lys Gln Glu Ser
    1330                1335                1340

His Gln Lys Ser His Gly Pro Gly Ser Asp Leu Glu Asn Phe Ala Leu
1345                1350                1355                1360

Phe Lys Leu Glu Glu Arg Glu Lys Lys Val Tyr Pro Lys Ala Val Glu
            1365                1370                1375

Arg Ser Ser Thr Phe Glu Asn Lys Ala Ser Met Gln Glu Ala Pro Pro
        1380                1385                1390

Leu Gly Ser Leu Leu Lys Asp Ala Leu His Lys Gln Ala Ser Val Arg
        1395                1400                1405

Ala Ser Glu Gly Ala Met Ser Asp Gly Arg Val Pro Ala Glu His Arg
    1410                1415                1420

Gln Gly Gly Gly Asp Phe Arg Arg Ala Pro Ala Pro Gly Thr Leu Gln
1425                1430                1435                1440

Asp Gly Leu Cys His Ser Leu Asp Arg Gly Ile Ser Gly Lys Gly Glu
        1445                1450                1455

Gly Thr Glu Lys Ser Ser Gln Ala Lys Glu Leu Leu Arg Cys Glu Lys
        1460                1465                1470

Leu Asp Ser Lys Leu Ala Asn Ile Asp Tyr Leu Arg Lys Lys Met Ser
    1475                1480                1485

Leu Glu Asp Lys Glu Asp Asn Leu Cys Pro Val Leu Lys Pro Lys Met
    1490                1495                1500

Thr Ala Gly Ser His Glu Cys Leu Pro Gly Asn Pro Val Arg Pro Thr
1505                1510                1515                1520

Gly Gly Gln Gln Glu Pro Pro Ala Ser Glu Ser Arg Ala Phe Val
            1525                1530                1535

Ser Ser Thr His Ala Ala Gln Met Ser Ala Val Ser Phe Val Pro Leu
        1540                1545                1550
```

```
Lys Ala Leu Thr Gly Arg Val Asp Ser Gly Thr Glu Lys Pro Gly Leu
            1555                1560                1565

Val Ala Pro Glu Ser Pro Val Arg Lys Ser Pro Ser Glu Tyr Lys Leu
        1570                1575                1580

Glu Gly Arg Ser Val Ser Cys Leu Lys Pro Ile Glu Gly Thr Leu Asp
1585                1590                1595                1600

Ile Ala Leu Leu Ser Gly Pro Gln Ala Ser Lys Thr Glu Leu Pro Ser
                1605                1610                1615

Pro Glu Ser Ala Gln Ser Pro Ser Pro Ser Gly Asp Val Arg Ala Ser
            1620                1625                1630

Val Pro Pro Val Leu Pro Ser Ser Ser Gly Lys Lys Asn Asp Thr Thr
        1635                1640                1645

Ser Ala Arg Glu Leu Ser Pro Ser Ser Leu Lys Met Asn Lys Ser Tyr
    1650                1655                1660

Leu Leu Glu Pro Trp Phe Leu Pro Pro Ser Arg Gly Leu Gln Asn Ser
1665                1670                1675                1680

Pro Ala Val Ser Leu Pro Asp Pro Glu Phe Lys Arg Asp Arg Lys Gly
                1685                1690                1695

Pro His Pro Thr Ala Arg Ser Pro Gly Thr Val Met Glu Ser Asn Pro
            1700                1705                1710

Gln Gln Arg Glu Gly Ser Ser Pro Lys His Gln Asp His Thr Thr Asp
        1715                1720                1725

Pro Lys Leu Leu Thr Cys Leu Gly Gln Asn Leu His Ser Pro Asp Leu
    1730                1735                1740

Ala Arg Pro Arg Cys Pro Leu Pro Pro Glu Ala Ser Pro Ser Arg Glu
1745                1750                1755                1760

Lys Pro Gly Leu Arg Glu Ser Ser Glu Arg Gly Pro Pro Thr Ala Arg
                1765                1770                1775

Ser Glu Arg Ser Ala Ala Arg Ala Asp Thr Cys Arg Glu Pro Ser Met
            1780                1785                1790

Glu Leu Cys Phe Pro Glu Thr Ala Lys Thr Ser Asp Asn Ser Lys Asn
        1795                1800                1805

Leu Leu Ser Val Gly Arg Thr His Pro Asp Phe Tyr Thr Gln Thr Gln
    1810                1815                1820

Ala Met Glu Lys Ala Trp Ala Pro Gly Gly Lys Thr Asn His Lys Asp
1825                1830                1835                1840

Gly Pro Gly Glu Ala Arg Pro Pro Arg Asp Asn Ser Ser Leu His
                1845                1850                1855

Ser Ala Gly Ile Pro Cys Glu Lys Glu Leu Gly Lys Val Arg Arg Gly
            1860                1865                1870

Val Glu Pro Lys Pro Glu Ala Leu Leu Ala Arg Arg Ser Leu Gln Pro
        1875                1880                1885

Pro Gly Ile Glu Ser Glu Lys Ser Glu Lys Leu Ser Ser Phe Pro Ser
    1890                1895                1900

Leu Gln Lys Asp Gly Ala Lys Glu Pro Glu Arg Lys Glu Gln Pro Leu
1905                1910                1915                1920

Gln Arg His Pro Ser Ser Ile Pro Pro Pro Leu Thr Ala Lys Asp
                1925                1930                1935

Leu Ser Ser Pro Ala Ala Arg Gln His Cys Ser Ser Pro Ser His Ala
            1940                1945                1950

Ser Gly Arg Glu Pro Gly Ala Lys Pro Ser Thr Ala Glu Pro Ser Ser
        1955                1960                1965
```

```
Ser Pro Gln Asp Pro Pro Lys Pro Val Ala Ala His Ser Glu Ser Ser
    1970                1975                1980

Ser His Lys Pro Arg Pro Gly Pro Asp Pro Gly Pro Pro Lys Thr Lys
1985                1990                1995                2000

His Pro Asp Arg Ser Leu Ser Ser Gln Lys Pro Ser Val Gly Ala Thr
            2005                2010                2015

Lys Gly Lys Glu Pro Ala Thr Gln Ser Leu Gly Gly Ser Ser Arg Glu
        2020                2025                2030

Gly Lys Gly His Ser Lys Ser Gly Pro Asp Val Phe Pro Ala Thr Pro
    2035                2040                2045

Gly Ser Gln Asn Lys Ala Ser Asp Gly Ile Gly Gln Gly Glu Gly Gly
2050                2055                2060

Pro Ser Val Pro Leu His Thr Asp Arg Ala Pro Leu Asp Ala Lys Pro
2065                2070                2075                2080

Gln Pro Thr Ser Gly Gly Arg Pro Leu Glu Val Leu Glu Lys Pro Val
            2085                2090                2095

His Leu Pro Arg Pro Gly His Pro Gly Pro Ser Glu Pro Ala Asp Gln
            2100                2105                2110

Lys Leu Ser Ala Val Gly Glu Lys Gln Thr Leu Ser Pro Lys His Pro
        2115                2120                2125

Lys Pro Ser Thr Val Lys Asp Cys Pro Thr Leu Cys Lys Gln Thr Asp
    2130                2135                2140

Asn Arg Gln Thr Asp Lys Ser Pro Ser Gln Pro Ala Ala Asn Thr Asp
2145                2150                2155                2160

Arg Arg Ala Glu Gly Lys Lys Cys Thr Glu Ala Leu Tyr Ala Pro Ala
            2165                2170                2175

Glu Gly Asp Lys Leu Glu Ala Gly Leu Ser Phe Val His Ser Glu Asn
            2180                2185                2190

Arg Leu Lys Gly Ala Glu Arg Pro Ala Ala Gly Val Gly Lys Gly Phe
        2195                2200                2205

Pro Glu Ala Arg Gly Lys Gly Pro Gly Pro Gln Lys Pro Pro Thr Glu
    2210                2215                2220

Ala Asp Lys Pro Asn Gly Met Lys Arg Ser Pro Ser Ala Thr Gly Gln
2225                2230                2235                2240

Ser Ser Phe Arg Ser Thr Ala Leu Pro Glu Lys Ser Leu Ser Cys Ser
            2245                2250                2255

Ser Ser Phe Pro Glu Thr Arg Ala Gly Val Arg Glu Ala Ser Ala Ala
            2260                2265                2270

Ser Ser Asp Thr Ser Ser Ala Lys Ala Ala Gly Gly Met Leu Glu Leu
        2275                2280                2285

Pro Ala Pro Ser Asn Arg Asp His Arg Lys Ala Gln Pro Ala Gly Glu
    2290                2295                2300

Gly Arg Thr His Met Thr Lys Ser Asp Ser Leu Pro Ser Phe Arg Val
2305                2310                2315                2320

Ser Thr Leu Pro Leu Glu Ser His His Pro Asp Pro Asn Thr Met Gly
            2325                2330                2335

Gly Ala Ser His Arg Asp Arg Ala Leu Ser Val Thr Ala Thr Val Gly
            2340                2345                2350

Glu Thr Lys Gly Lys Asp Pro Ala Pro Ala Gln Pro Pro Ala Arg
        2355                2360                2365

Lys Gln Asn Val Gly Arg Asp Val Thr Lys Pro Ser Pro Ala Pro Asn
    2370                2375                2380
```

```
Thr Asp Arg Pro Ile Ser Leu Ser Asn Glu Lys Asp Phe Val Val Arg
2385                2390                2395                2400

Gln Arg Arg Gly Lys Glu Ser Leu Arg Ser Ser Pro His Lys Lys Ala
            2405                2410                2415

Leu

<210> SEQ ID NO 5
<211> LENGTH: 2362
<212> TYPE: PRT
<213> ORGANISM: Homo sapiens

<400> SEQUENCE: 5

Met Asp Met Ser Asp Pro Asn Phe Trp Thr Val Leu Ser Asn Phe Thr
1               5                   10                  15

Leu Pro His Leu Arg Ser Gly Asn Arg Leu Arg Arg Thr Gln Ser Cys
                20                  25                  30

Arg Thr Ser Asn Arg Lys Ser Leu Ile Gly Asn Gly Gln Ser Pro Ala
            35                  40                  45

Leu Pro Arg Pro His Ser Pro Leu Ser Ala His Ala Gly Asn Ser Pro
        50                  55                  60

Gln Asp Ser Pro Arg Asn Phe Ser Pro Ser Ala Ser His Phe Ser
65                  70                  75                  80

Phe Ala Arg Arg Thr Asp Gly Arg Arg Trp Ser Leu Ala Ser Leu Pro
                85                  90                  95

Ser Ser Gly Tyr Gly Thr Asn Thr Pro Ser Ser Thr Val Ser Ser Ser
                100                 105                 110

Cys Ser Ser Gln Glu Lys Leu His Gln Leu Pro Tyr Gln Pro Thr Pro
            115                 120                 125

Asp Glu Leu His Phe Leu Ser Lys His Phe Cys Thr Thr Glu Ser Ile
        130                 135                 140

Ala Thr Glu Asn Arg Cys Arg Asn Thr Pro Met Arg Pro Arg Ser Arg
145                 150                 155                 160

Ser Leu Ser Pro Gly Arg Ser Pro Ala Cys Cys Asp His Glu Ile Ile
                165                 170                 175

Met Met Asn His Val Tyr Lys Glu Arg Phe Pro Lys Ala Thr Ala Gln
                180                 185                 190

Met Glu Glu Arg Leu Lys Glu Ile Ile Thr Ser Tyr Ser Pro Asp Asn
            195                 200                 205

Val Leu Pro Leu Ala Asp Gly Val Leu Ser Phe Thr His His Gln Ile
        210                 215                 220

Ile Glu Leu Ala Arg Asp Cys Leu Asp Lys Ser His Gln Gly Leu Ile
225                 230                 235                 240

Thr Ser Arg Tyr Phe Leu Glu Leu Gln His Lys Leu Asp Lys Leu Leu
                245                 250                 255

Gln Glu Ala His Asp Arg Ser Glu Ser Gly Glu Leu Ala Phe Ile Lys
                260                 265                 270

Gln Leu Val Arg Lys Ile Leu Ile Val Ile Ala Arg Pro Ala Arg Leu
            275                 280                 285

Leu Glu Cys Leu Glu Phe Asp Pro Glu Glu Phe Tyr Tyr Leu Leu Glu
        290                 295                 300

Ala Ala Glu Gly His Ala Lys Glu Gly Gln Gly Ile Lys Thr Asp Ile
305                 310                 315                 320

Pro Arg Tyr Ile Ile Ser Gln Leu Gly Leu Asn Lys Asp Pro Leu Glu
                325                 330                 335
```

-continued

Glu Met Ala His Leu Gly Asn Tyr Asp Ser Gly Thr Ala Glu Thr Pro
            340                 345                 350

Glu Thr Asp Glu Ser Val Ser Ser Asn Ala Ser Leu Lys Leu Arg
        355                 360                 365

Arg Lys Pro Arg Glu Ser Asp Phe Glu Thr Ile Lys Leu Ile Ser Asn
    370                 375                 380

Gly Ala Tyr Gly Ala Val Tyr Phe Val Arg His Lys Glu Ser Arg Gln
385                 390                 395                 400

Arg Phe Ala Met Lys Lys Ile Asn Lys Gln Asn Leu Ile Leu Arg Asn
                405                 410                 415

Gln Ile Gln Gln Ala Phe Val Glu Arg Asp Ile Leu Thr Phe Ala Glu
            420                 425                 430

Asn Pro Phe Val Val Ser Met Tyr Cys Ser Phe Glu Thr Arg Arg His
            435                 440                 445

Leu Cys Met Val Met Glu Tyr Val Glu Gly Gly Asp Cys Ala Thr Leu
        450                 455                 460

Met Lys Asn Met Gly Pro Leu Pro Val Asp Met Ala Arg Met Tyr Phe
465                 470                 475                 480

Ala Glu Thr Val Leu Ala Leu Glu Tyr Leu His Asn Tyr Gly Ile Val
                485                 490                 495

His Arg Asp Leu Lys Pro Asp Asn Leu Leu Val Thr Ser Met Gly His
            500                 505                 510

Ile Lys Leu Thr Asp Phe Gly Leu Ser Lys Val Gly Leu Met Ser Met
        515                 520                 525

Thr Thr Asn Leu Tyr Glu Gly His Ile Glu Lys Asp Ala Arg Glu Phe
530                 535                 540

Leu Asp Lys Gln Val Cys Gly Thr Pro Glu Tyr Ile Ala Pro Glu Val
545                 550                 555                 560

Ile Leu Arg Gln Gly Tyr Gly Lys Pro Val Asp Trp Trp Ala Met Gly
                565                 570                 575

Ile Ile Leu Tyr Glu Phe Leu Val Gly Cys Val Pro Phe Phe Gly Asp
            580                 585                 590

Thr Pro Glu Glu Leu Phe Gly Gln Val Ile Ser Asp Glu Ile Asn Trp
        595                 600                 605

Pro Glu Lys Asp Glu Ala Pro Pro Asp Ala Gln Asp Leu Ile Thr
    610                 615                 620

Leu Leu Leu Arg Gln Asn Pro Leu Glu Arg Leu Gly Thr Gly Gly Ala
625                 630                 635                 640

Tyr Glu Val Lys Gln His Arg Phe Phe Arg Ser Leu Asp Trp Asn Ser
                645                 650                 655

Leu Leu Arg Gln Lys Ala Glu Phe Ile Pro Gln Leu Glu Ser Glu Asp
            660                 665                 670

Asp Thr Ser Tyr Phe Asp Thr Arg Ser Glu Lys Tyr His His Met Glu
        675                 680                 685

Thr Glu Glu Glu Asp Asp Thr Asn Asp Glu Asp Phe Asn Val Glu Ile
    690                 695                 700

Arg Gln Phe Ser Ser Cys Ser His Arg Phe Ser Lys Val Phe Ser Ser
705                 710                 715                 720

Ile Asp Arg Ile Thr Gln Asn Ser Ala Glu Glu Lys Glu Asp Ser Val
                725                 730                 735

Asp Lys Thr Lys Ser Thr Thr Leu Pro Ser Thr Glu Thr Leu Ser Trp
            740                 745                 750

-continued

```
Ser Ser Glu Tyr Ser Glu Met Gln Gln Leu Ser Thr Ser Asn Ser Ser
        755                 760                 765

Asp Thr Glu Ser Asn Arg His Lys Leu Ser Ser Gly Leu Leu Pro Lys
770                 775                 780

Leu Ala Ile Ser Thr Glu Gly Glu Gln Asp Glu Ala Ala Ser Cys Pro
785                 790                 795                 800

Gly Asp Pro His Glu Pro Gly Lys Pro Ala Leu Pro Pro Glu Glu
                805                 810                 815

Cys Ala Gln Glu Pro Glu Val Thr Thr Pro Ala Ser Thr Ile Ser
                820                 825                 830

Ser Ser Thr Leu Ser Asp Met Phe Ala Val Ser Pro Leu Gly Ser Pro
        835                 840                 845

Met Ser Pro His Ser Leu Ser Ser Asp Pro Ser Ser Ser Arg Asp Ser
850                 855                 860

Ser Pro Ser Arg Asp Ser Ser Ala Ala Ser Ala Ser Pro His Gln Pro
865                 870                 875                 880

Ile Val Ile His Ser Ser Gly Lys Asn Tyr Gly Phe Thr Ile Arg Ala
                885                 890                 895

Ile Arg Val Tyr Val Gly Asp Ser Asp Ile Tyr Thr Val His His Ile
                900                 905                 910

Val Trp Asn Val Glu Glu Gly Ser Pro Ala Cys Gln Ala Gly Leu Lys
        915                 920                 925

Ala Gly Asp Leu Ile Thr His Ile Asn Gly Glu Pro Val His Gly Leu
        930                 935                 940

Val His Thr Glu Val Ile Glu Leu Leu Leu Lys Ser Gly Asn Lys Val
945                 950                 955                 960

Ser Ile Thr Thr Thr Pro Phe Glu Asn Thr Ser Ile Lys Thr Gly Pro
                965                 970                 975

Ala Arg Arg Asn Ser Tyr Lys Ser Arg Met Val Arg Arg Ser Lys Lys
                980                 985                 990

Ser Lys Lys Lys Glu Ser Leu Glu Arg Arg Ser Leu Phe Lys Lys
        995                 1000                1005

Leu Ala Lys Gln Pro Ser Pro Leu Leu His Thr Ser Arg Ser Phe Ser
    1010                1015                1020

Cys Leu Asn Arg Ser Leu Ser Ser Gly Glu Ser Leu Pro Gly Ser Pro
1025                1030                1035                1040

Thr His Ser Leu Ser Pro Arg Ser Pro Thr Pro Ser Tyr Arg Ser Thr
                1045                1050                1055

Pro Asp Phe Pro Ser Gly Thr Asn Ser Ser Gln Ser Ser Ser Pro Ser
    1060                1065                1070

Ser Ser Ala Pro Asn Ser Pro Ala Gly Ser Gly His Ile Arg Pro Ser
    1075                1080                1085

Thr Leu His Gly Leu Ala Pro Lys Leu Gly Gly Gln Arg Tyr Arg Ser
    1090                1095                1100

Gly Arg Arg Lys Ser Ala Gly Asn Ile Pro Leu Ser Pro Leu Ala Arg
1105                1110                1115                1120

Thr Pro Ser Pro Thr Pro Gln Pro Thr Ser Pro Gln Arg Ser Pro Ser
                1125                1130                1135

Pro Leu Leu Gly His Ser Leu Gly Asn Ser Lys Ile Ala Gln Ala Phe
            1140                1145                1150

Pro Ser Lys Met His Ser Pro Pro Thr Ile Val Arg His Ile Val Arg
        1155                1160                1165
```

-continued

Pro Lys Ser Ala Glu Pro Pro Arg Ser Pro Leu Leu Lys Arg Val Gln
    1170                1175                1180

Ser Glu Glu Lys Leu Ser Pro Ser Tyr Gly Ser Asp Lys Lys His Leu
1185                1190                1195                1200

Cys Ser Arg Lys His Ser Leu Glu Val Thr Gln Glu Glu Val Gln Arg
            1205                1210                1215

Glu Gln Ser Gln Arg Glu Ala Pro Leu Gln Ser Leu Asp Glu Asn Val
        1220                1225                1230

Cys Asp Val Pro Pro Leu Ser Arg Ala Arg Pro Val Glu Gln Gly Cys
    1235                1240                1245

Leu Lys Arg Pro Val Ser Arg Lys Val Gly Arg Gln Glu Ser Val Asp
1250                1255                1260

Asp Leu Asp Arg Asp Lys Leu Lys Ala Lys Val Val Lys Lys Ala
1265                1270                1275                1280

Asp Gly Phe Pro Glu Lys Gln Glu Ser His Gln Lys Ser His Gly Pro
            1285                1290                1295

Gly Ser Asp Leu Glu Asn Phe Ala Leu Phe Lys Leu Glu Glu Arg Glu
        1300                1305                1310

Lys Lys Val Tyr Pro Lys Ala Val Glu Arg Ser Ser Thr Phe Glu Asn
    1315                1320                1325

Lys Ala Ser Met Gln Glu Ala Pro Pro Leu Gly Ser Leu Leu Lys Asp
1330                1335                1340

Ala Leu His Lys Gln Ala Ser Val Arg Ala Ser Glu Gly Ala Met Ser
1345                1350                1355                1360

Asp Gly Arg Val Pro Ala Glu His Arg Gln Gly Gly Asp Phe Arg
            1365                1370                1375

Arg Ala Pro Ala Pro Gly Thr Leu Gln Asp Gly Leu Cys His Ser Leu
        1380                1385                1390

Asp Arg Gly Ile Ser Gly Lys Gly Glu Gly Thr Glu Lys Ser Ser Gln
    1395                1400                1405

Ala Lys Glu Leu Leu Arg Cys Glu Lys Leu Asp Ser Lys Leu Ala Asn
1410                1415                1420

Ile Asp Tyr Leu Arg Lys Lys Met Ser Leu Glu Asp Lys Glu Asp Asn
1425                1430                1435                1440

Leu Cys Pro Val Leu Lys Pro Lys Met Thr Ala Gly Ser His Glu Cys
            1445                1450                1455

Leu Pro Gly Asn Pro Val Arg Pro Thr Gly Gly Gln Gln Glu Pro Pro
        1460                1465                1470

Pro Ala Ser Glu Ser Arg Ala Phe Val Ser Ser Thr His Ala Ala Gln
    1475                1480                1485

Met Ser Ala Val Ser Phe Val Pro Leu Lys Ala Leu Thr Gly Arg Val
1490                1495                1500

Asp Ser Gly Thr Glu Lys Pro Gly Leu Val Ala Pro Glu Ser Pro Val
1505                1510                1515                1520

Arg Lys Ser Pro Ser Glu Tyr Lys Leu Glu Gly Arg Ser Val Ser Cys
            1525                1530                1535

Leu Lys Pro Ile Glu Gly Thr Leu Asp Ile Ala Leu Leu Ser Gly Pro
        1540                1545                1550

Gln Ala Ser Lys Thr Glu Leu Pro Ser Pro Glu Ser Ala Gln Ser Pro
    1555                1560                1565

Ser Pro Ser Gly Asp Val Arg Ala Ser Val Pro Pro Val Leu Pro Ser
1570                1575                1580

```
Ser Ser Gly Lys Lys Asn Asp Thr Thr Ser Ala Arg Glu Leu Ser Pro
1585                1590                1595                1600

Ser Ser Leu Lys Met Asn Lys Ser Tyr Leu Leu Glu Pro Trp Phe Leu
            1605                1610                1615

Pro Pro Ser Arg Gly Leu Gln Asn Ser Pro Ala Val Ser Leu Pro Asp
        1620                1625                1630

Pro Glu Phe Lys Arg Asp Arg Lys Gly Pro His Pro Thr Ala Arg Ser
    1635                1640                1645

Pro Gly Thr Val Met Glu Ser Asn Pro Gln Gln Arg Glu Gly Ser Ser
1650                1655                1660

Pro Lys His Gln Asp His Thr Thr Asp Pro Lys Leu Leu Thr Cys Leu
1665                1670                1675                1680

Gly Gln Asn Leu His Ser Pro Asp Leu Ala Arg Pro Arg Cys Pro Leu
            1685                1690                1695

Pro Pro Glu Ala Ser Pro Ser Arg Glu Lys Pro Gly Leu Arg Glu Ser
        1700                1705                1710

Ser Glu Arg Gly Pro Pro Thr Ala Arg Ser Glu Arg Ser Ala Ala Arg
    1715                1720                1725

Ala Asp Thr Cys Arg Glu Pro Ser Met Glu Leu Cys Phe Pro Glu Thr
1730                1735                1740

Ala Lys Thr Ser Asp Asn Ser Lys Asn Leu Leu Ser Val Gly Arg Thr
1745                1750                1755                1760

His Pro Asp Phe Tyr Thr Gln Thr Gln Ala Met Glu Lys Ala Trp Ala
            1765                1770                1775

Pro Gly Gly Lys Thr Asn His Lys Asp Gly Pro Gly Glu Ala Arg Pro
        1780                1785                1790

Pro Pro Arg Asp Asn Ser Ser Leu His Ser Ala Gly Ile Pro Cys Glu
    1795                1800                1805

Lys Glu Leu Gly Lys Val Arg Arg Gly Val Glu Pro Lys Pro Glu Ala
1810                1815                1820

Leu Leu Ala Arg Arg Ser Leu Gln Pro Pro Gly Ile Glu Ser Glu Lys
1825                1830                1835                1840

Ser Glu Lys Leu Ser Ser Phe Pro Ser Leu Gln Lys Asp Gly Ala Lys
            1845                1850                1855

Glu Pro Glu Arg Lys Glu Gln Pro Leu Gln Arg His Pro Ser Ser Ile
        1860                1865                1870

Pro Pro Pro Pro Leu Thr Ala Lys Asp Leu Ser Ser Pro Ala Ala Arg
    1875                1880                1885

Gln His Cys Ser Ser Pro Ser His Ala Ser Gly Arg Glu Pro Gly Ala
1890                1895                1900

Lys Pro Ser Thr Ala Glu Pro Ser Ser Ser Pro Gln Asp Pro Pro Lys
1905                1910                1915                1920

Pro Val Ala Ala His Ser Glu Ser Ser Ser His Lys Pro Arg Pro Gly
            1925                1930                1935

Pro Asp Pro Gly Pro Pro Lys Thr Lys His Pro Asp Arg Ser Leu Ser
        1940                1945                1950

Ser Gln Lys Pro Ser Val Gly Ala Thr Lys Gly Lys Glu Pro Ala Thr
    1955                1960                1965

Gln Ser Leu Gly Gly Ser Ser Arg Glu Gly Lys Gly His Ser Lys Ser
1970                1975                1980

Gly Pro Asp Val Phe Pro Ala Thr Pro Gly Ser Gln Asn Lys Ala Ser
1985                1990                1995                2000
```

Asp Gly Ile Gly Gln Gly Glu Gly Gly Pro Ser Val Pro Leu His Thr
        2005                2010                2015

Asp Arg Ala Pro Leu Asp Ala Lys Pro Gln Pro Thr Ser Gly Gly Arg
        2020                2025                2030

Pro Leu Glu Val Leu Glu Lys Pro Val His Leu Pro Arg Pro Gly His
        2035                2040                2045

Pro Gly Pro Ser Glu Pro Ala Asp Gln Lys Leu Ser Ala Val Gly Glu
        2050                2055                2060

Lys Gln Thr Leu Ser Pro Lys His Pro Lys Pro Ser Thr Val Lys Asp
2065                2070                2075                2080

Cys Pro Thr Leu Cys Lys Gln Thr Asp Asn Arg Gln Thr Asp Lys Ser
            2085                2090                2095

Pro Ser Gln Pro Ala Asn Thr Asp Arg Arg Ala Glu Gly Lys Lys
        2100                2105                2110

Cys Thr Glu Ala Leu Tyr Ala Pro Ala Glu Gly Asp Lys Leu Glu Ala
            2115                2120                2125

Gly Leu Ser Phe Val His Ser Glu Asn Arg Leu Lys Gly Ala Glu Arg
        2130                2135                2140

Pro Ala Ala Gly Val Gly Lys Gly Phe Pro Glu Ala Arg Gly Lys Gly
2145                2150                2155                2160

Pro Gly Pro Gln Lys Pro Pro Thr Glu Ala Asp Lys Pro Asn Gly Met
            2165                2170                2175

Lys Arg Ser Pro Ser Ala Thr Gly Gln Ser Ser Phe Arg Ser Thr Ala
        2180                2185                2190

Leu Pro Glu Lys Ser Leu Ser Cys Ser Ser Ser Phe Pro Glu Thr Arg
        2195                2200                2205

Ala Gly Val Arg Glu Ala Ser Ala Ala Ser Ser Asp Thr Ser Ser Ala
        2210                2215                2220

Lys Ala Ala Gly Gly Met Leu Glu Leu Pro Ala Pro Ser Asn Arg Asp
2225                2230                2235                2240

His Arg Lys Ala Gln Pro Ala Gly Glu Gly Arg Thr His Met Thr Lys
            2245                2250                2255

Ser Asp Ser Leu Pro Ser Phe Arg Val Ser Thr Leu Pro Leu Glu Ser
        2260                2265                2270

His His Pro Asp Pro Asn Thr Met Gly Gly Ala Ser His Arg Asp Arg
        2275                2280                2285

Ala Leu Ser Val Thr Ala Thr Val Gly Glu Thr Lys Gly Lys Asp Pro
        2290                2295                2300

Ala Pro Ala Gln Pro Pro Pro Ala Arg Lys Gln Asn Val Gly Arg Asp
2305                2310                2315                2320

Val Thr Lys Pro Ser Pro Ala Pro Asn Thr Asp Arg Pro Ile Ser Leu
            2325                2330                2335

Ser Asn Glu Lys Asp Phe Val Val Arg Gln Arg Gly Lys Glu Ser
        2340                2345                2350

Leu Arg Ser Ser Pro His Lys Lys Ala Leu
        2355                2360

<210> SEQ ID NO 6
<211> LENGTH: 238
<212> TYPE: PRT
<213> ORGANISM: Homo sapiens

```
<400> SEQUENCE: 6

Met Gly Glu Lys Val Ser Glu Ala Pro Glu Val Pro Arg Gly Cys
1               5                  10                  15

Ser Gly His Gly Ser Arg Thr Pro Ala Ser Ala Leu Val Ala Ala Ser
            20                  25                  30

Ser Pro Gly Ala Ser Ser Ala Glu Ser Ser Ser Gly Ser Glu Thr Leu
        35                  40                  45

Ser Glu Glu Gly Glu Pro Gly Gly Phe Ser Arg Glu His Gln Pro Pro
    50                  55                  60

Pro Pro Pro Pro Leu Gly Gly Thr Leu Gly Ala Arg Ala Pro Ala Ala
65                  70                  75                  80

Trp Ala Pro Ala Ser Val Leu Leu Glu Arg Gly Val Leu Ala Leu Pro
                85                  90                  95

Pro Pro Leu Pro Gly Gly Ala Val Pro Ala Pro Arg Gly Ser Ser
            100                 105                 110

Ala Ser Gln Glu Glu Gln Asp Glu Glu Leu Asp His Ile Leu Ser Pro
        115                 120                 125

Pro Pro Met Pro Phe Arg Lys Cys Ser Asn Pro Asp Val Ala Ser Gly
    130                 135                 140

Pro Gly Lys Ser Leu Lys Tyr Lys Arg Gln Leu Ser Glu Asp Gly Arg
145                 150                 155                 160

Gln Leu Arg Arg Gly Ser Leu Gly Gly Ala Leu Thr Gly Arg Tyr Leu
                165                 170                 175

Leu Pro Asn Pro Val Ala Gly Gln Ala Trp Pro Ala Ser Ala Glu Thr
            180                 185                 190

Ser Asn Leu Val Arg Met Arg Ser Gln Ala Leu Gly Gln Ser Ala Pro
        195                 200                 205

Ser Leu Thr Ala Ser Leu Lys Glu Leu Ser Leu Pro Arg Arg Gly Ser
    210                 215                 220

Phe Pro Val Cys Pro Asn Ala Gly Arg Thr Ser Pro Leu Gly
225                 230                 235

<210> SEQ ID NO 7
<211> LENGTH: 2429
<212> TYPE: PRT
<213> ORGANISM: Homo sapiens

<400> SEQUENCE: 7

Met Asp Met Ser Asp Pro Asn Phe Trp Thr Val Leu Ser Asn Phe Thr
1               5                  10                  15

Leu Pro His Leu Arg Ser Gly Asn Arg Leu Arg Arg Thr Gln Ser Cys
            20                  25                  30

Arg Thr Ser Asn Arg Lys Ser Leu Ile Gly Asn Gly Gln Ser Pro Ala
        35                  40                  45

Leu Pro Arg Pro His Ser Pro Leu Ser Ala His Ala Gly Asn Ser Pro
    50                  55                  60

Gln Asp Ser Pro Arg Asn Phe Ser Pro Ser Ala Ser Ala His Phe Ser
65                  70                  75                  80

Phe Ala Arg Arg Thr Asp Gly Arg Arg Trp Ser Leu Ala Ser Leu Pro
                85                  90                  95

Ser Ser Gly Tyr Gly Thr Asn Thr Pro Ser Ser Thr Val Ser Ser Ser
            100                 105                 110

Cys Ser Ser Gln Glu Lys Leu His Gln Leu Pro Tyr Gln Pro Thr Pro
        115                 120                 125
```

-continued

```
Asp Glu Leu His Phe Leu Ser Lys His Phe Cys Thr Thr Glu Ser Ile
130                 135                 140
Ala Thr Glu Asn Arg Cys Arg Asn Thr Pro Met Arg Pro Arg Ser Arg
145                 150                 155                 160
Ser Leu Ser Pro Gly Arg Ser Pro Ala Cys Cys Asp His Glu Ile Ile
            165                 170                 175
Met Met Asn His Val Tyr Lys Glu Arg Phe Pro Lys Ala Thr Ala Gln
            180                 185                 190
Met Glu Glu Arg Leu Lys Glu Ile Ile Thr Ser Tyr Ser Pro Asp Asn
        195                 200                 205
Val Leu Pro Leu Ala Asp Gly Val Leu Ser Phe Thr His His Gln Ile
210                 215                 220
Ile Glu Leu Ala Arg Asp Cys Leu Asp Lys Ser His Gln Gly Leu Ile
225                 230                 235                 240
Thr Ser Arg Tyr Phe Leu Glu Leu Gln His Lys Leu Asp Lys Leu Leu
            245                 250                 255
Gln Glu Ala His Asp Arg Ser Glu Ser Gly Glu Leu Ala Phe Ile Lys
            260                 265                 270
Gln Leu Val Arg Lys Ile Leu Ile Val Ile Ala Arg Pro Ala Arg Leu
        275                 280                 285
Leu Glu Cys Leu Glu Phe Asp Pro Glu Glu Phe Tyr Tyr Leu Leu Glu
290                 295                 300
Ala Ala Glu Gly His Ala Lys Glu Gly Gln Gly Ile Lys Thr Asp Ile
305                 310                 315                 320
Pro Arg Tyr Ile Ile Ser Gln Leu Gly Leu Asn Lys Asp Pro Leu Glu
            325                 330                 335
Glu Met Ala His Leu Gly Asn Tyr Asp Ser Gly Thr Ala Glu Thr Pro
            340                 345                 350
Glu Thr Asp Glu Ser Val Ser Ser Asn Ala Ser Leu Lys Leu Arg
        355                 360                 365
Arg Lys Pro Arg Glu Ser Asp Phe Glu Thr Ile Lys Leu Ile Ser Asn
370                 375                 380
Gly Ala Tyr Gly Ala Val Tyr Phe Val Arg His Lys Glu Ser Arg Gln
385                 390                 395                 400
Arg Phe Ala Met Lys Lys Ile Asn Lys Gln Asn Leu Ile Leu Arg Asn
            405                 410                 415
Gln Ile Gln Gln Ala Phe Val Glu Arg Asp Ile Leu Thr Phe Ala Glu
            420                 425                 430
Asn Pro Phe Val Val Ser Met Tyr Cys Ser Phe Glu Thr Arg Arg His
            435                 440                 445
Leu Cys Met Val Met Glu Tyr Val Glu Gly Gly Asp Cys Ala Thr Leu
        450                 455                 460
Met Lys Asn Met Gly Pro Leu Pro Val Asp Met Ala Arg Met Tyr Phe
465                 470                 475                 480
Ala Glu Thr Val Leu Ala Leu Glu Tyr Leu His Asn Tyr Gly Ile Val
            485                 490                 495
His Arg Asp Leu Lys Pro Asp Asn Leu Leu Val Thr Ser Met Gly His
            500                 505                 510
Ile Lys Leu Thr Asp Phe Gly Leu Ser Lys Val Gly Leu Met Ser Met
        515                 520                 525
Thr Thr Asn Leu Tyr Glu Gly His Ile Glu Lys Asp Ala Arg Glu Phe
530                 535                 540
```

```
Leu Asp Lys Gln Val Cys Gly Thr Pro Glu Tyr Ile Ala Pro Glu Val
545                 550                 555                 560
Ile Leu Arg Gln Gly Tyr Gly Lys Pro Val Asp Trp Trp Ala Met Gly
            565                 570                 575
Ile Ile Leu Tyr Glu Phe Leu Val Gly Cys Val Pro Phe Phe Gly Asp
                580                 585                 590
Thr Pro Glu Glu Leu Phe Gly Gln Val Ile Ser Asp Glu Ile Asn Trp
            595                 600                 605
Pro Glu Lys Asp Glu Ala Pro Pro Asp Ala Gln Asp Leu Ile Thr
        610                 615                 620
Leu Leu Leu Arg Gln Asn Pro Leu Glu Arg Leu Gly Thr Gly Gly Ala
625                 630                 635                 640
Tyr Glu Val Lys Gln His Arg Phe Phe Arg Ser Leu Asp Trp Asn Ser
                645                 650                 655
Leu Leu Arg Gln Lys Ala Glu Phe Ile Pro Gln Leu Glu Ser Glu Asp
            660                 665                 670
Asp Thr Ser Tyr Phe Asp Thr Arg Ser Glu Lys Tyr His His Met Glu
        675                 680                 685
Thr Glu Glu Glu Asp Asp Thr Asn Asp Glu Asp Phe Asn Val Glu Ile
        690                 695                 700
Arg Gln Phe Ser Ser Cys Ser His Arg Phe Ser Lys Val Phe Ser Ser
705                 710                 715                 720
Ile Asp Arg Ile Thr Gln Asn Ser Ala Glu Gly Lys Glu Asp Ser Val
                725                 730                 735
Asp Lys Thr Lys Ser Thr Thr Leu Pro Ser Thr Glu Thr Leu Ser Trp
            740                 745                 750
Ser Ser Glu Tyr Ser Glu Met Gln Gln Leu Ser Thr Ser Asn Ser Ser
        755                 760                 765
Asp Thr Glu Ser Asn Arg His Lys Leu Ser Ser Gly Leu Leu Pro Lys
        770                 775                 780
Leu Ala Ile Ser Thr Glu Gly Glu Gln Asp Glu Ala Ala Ser Cys Pro
785                 790                 795                 800
Gly Asp Pro His Glu Glu Pro Gly Lys Pro Ala Leu Pro Pro Glu Glu
                805                 810                 815
Cys Ala Gln Glu Glu Pro Glu Val Thr Thr Pro Ala Ser Thr Ile Ser
            820                 825                 830
Ser Ser Thr Leu Ser Val Gly Ser Phe Ser Glu His Leu Asp Gln Ile
        835                 840                 845
Asn Gly Arg Ser Glu Cys Val Asp Ser Thr Asp Asn Ser Ser Lys Pro
        850                 855                 860
Ser Ser Glu Pro Ala Ser His Met Ala Arg Gln Arg Leu Glu Ser Thr
865                 870                 875                 880
Glu Lys Lys Lys Ile Ser Gly Lys Val Thr Lys Ser Leu Ser Ala Ser
                885                 890                 895
Ala Leu Ser Leu Met Ile Pro Gly Asp Met Phe Ala Val Ser Pro Leu
            900                 905                 910
Gly Ser Pro Met Ser Pro His Ser Leu Ser Ser Asp Pro Ser Ser Ser
        915                 920                 925
Arg Asp Ser Ser Pro Ser Arg Asp Ser Ala Ala Ser Ala Ser Pro
        930                 935                 940
His Gln Pro Ile Val Ile His Ser Ser Gly Lys Asn Tyr Gly Phe Thr
945                 950                 955                 960
```

-continued

Ile Arg Ala Ile Arg Val Tyr Val Gly Asp Ser Asp Ile Tyr Thr Val
            965                 970                 975

His His Ile Val Trp Asn Val Glu Glu Gly Ser Pro Ala Cys Gln Ala
        980                 985                 990

Gly Leu Lys Ala Gly Asp Leu Ile Thr His Ile Asn Gly Glu Pro Val
        995                 1000                1005

His Gly Leu Val His Thr Glu Val Ile Glu Leu Leu Leu Lys Ser Gly
    1010                1015                1020

Asn Lys Val Ser Ile Thr Thr Thr Pro Phe Glu Asn Thr Ser Ile Lys
1025                1030                1035                1040

Thr Gly Pro Ala Arg Arg Asn Ser Tyr Lys Ser Arg Met Val Arg Arg
        1045                1050                1055

Ser Lys Lys Ser Lys Lys Lys Glu Ser Leu Glu Arg Arg Arg Ser Leu
            1060                1065                1070

Phe Lys Lys Leu Ala Lys Gln Pro Ser Pro Leu Leu His Thr Ser Arg
        1075                1080                1085

Ser Phe Ser Cys Leu Asn Arg Ser Leu Ser Ser Gly Glu Ser Leu Pro
    1090                1095                1100

Gly Ser Pro Thr His Ser Leu Ser Pro Arg Ser Pro Thr Pro Ser Tyr
1105                1110                1115                1120

Arg Ser Thr Pro Asp Phe Pro Ser Gly Thr Asn Ser Ser Gln Ser Ser
            1125                1130                1135

Ser Pro Ser Ser Ser Ala Pro Asn Ser Pro Ala Gly Ser Gly His Ile
            1140                1145                1150

Arg Pro Ser Thr Leu His Gly Leu Ala Pro Lys Leu Gly Gly Gln Arg
        1155                1160                1165

Tyr Arg Ser Gly Arg Arg Lys Ser Ala Gly Asn Ile Pro Leu Ser Pro
    1170                1175                1180

Leu Ala Arg Thr Pro Ser Pro Thr Pro Gln Pro Thr Ser Pro Gln Arg
1185                1190                1195                1200

Ser Pro Ser Pro Leu Leu Gly His Ser Leu Gly Asn Ser Lys Ile Ala
            1205                1210                1215

Gln Ala Phe Pro Ser Lys Met His Ser Pro Pro Thr Ile Val Arg His
        1220                1225                1230

Ile Val Arg Pro Lys Ser Ala Glu Pro Pro Arg Ser Pro Leu Leu Lys
    1235                1240                1245

Arg Val Gln Ser Glu Glu Lys Leu Ser Pro Ser Tyr Gly Ser Asp Lys
1250                1255                1260

Lys His Leu Cys Ser Arg Lys His Ser Leu Glu Val Thr Gln Glu Glu
1265                1270                1275                1280

Val Gln Arg Glu Gln Ser Gln Arg Glu Ala Pro Leu Gln Ser Leu Asp
        1285                1290                1295

Glu Asn Val Cys Asp Val Pro Pro Leu Ser Arg Ala Arg Pro Val Glu
    1300                1305                1310

Gln Gly Cys Leu Lys Arg Pro Val Ser Arg Lys Val Gly Arg Gln Glu
        1315                1320                1325

Ser Val Asp Asp Leu Asp Arg Asp Lys Leu Lys Ala Lys Val Val Val
    1330                1335                1340

Lys Lys Ala Asp Gly Phe Pro Glu Lys Gln Glu Ser His Gln Lys Ser
1345                1350                1355                1360

His Gly Pro Gly Ser Asp Leu Glu Asn Phe Ala Leu Phe Lys Leu Glu
        1365                1370                1375

-continued

Glu Arg Glu Lys Lys Val Tyr Pro Lys Ala Val Glu Arg Ser Ser Thr
      1380                1385                1390

Phe Glu Asn Lys Ala Ser Met Gln Glu Ala Pro Pro Leu Gly Ser Leu
1395                1400                1405

Leu Lys Asp Ala Leu His Lys Gln Ala Ser Val Arg Ala Ser Glu Gly
      1410                1415                1420

Ala Met Ser Asp Gly Arg Val Pro Ala Glu His Arg Gln Gly Gly Gly
1425                1430                1435                1440

Asp Phe Arg Arg Ala Pro Ala Pro Gly Thr Leu Gln Asp Gly Leu Cys
            1445                1450                1455

His Ser Leu Asp Arg Gly Ile Ser Gly Lys Gly Glu Gly Thr Glu Lys
      1460                1465                1470

Ser Ser Gln Ala Lys Glu Leu Leu Arg Cys Glu Lys Leu Asp Ser Lys
      1475                1480                1485

Leu Ala Asn Ile Asp Tyr Leu Arg Lys Lys Met Ser Leu Glu Asp Lys
      1490                1495                1500

Glu Asp Asn Leu Cys Pro Val Leu Lys Pro Lys Met Thr Ala Gly Ser
1505                1510                1515                1520

His Glu Cys Leu Pro Gly Asn Pro Val Arg Pro Thr Gly Gly Gln Gln
            1525                1530                1535

Glu Pro Pro Pro Ala Ser Glu Ser Arg Ala Phe Val Ser Ser Thr His
            1540                1545                1550

Ala Ala Gln Met Ser Ala Val Ser Phe Val Pro Leu Lys Ala Leu Thr
      1555                1560                1565

Gly Arg Val Asp Ser Gly Thr Glu Lys Pro Gly Leu Val Ala Pro Glu
      1570                1575                1580

Ser Pro Val Arg Lys Ser Pro Ser Glu Tyr Lys Leu Glu Gly Arg Ser
1585                1590                1595                1600

Val Ser Cys Leu Lys Pro Ile Glu Gly Thr Leu Asp Ile Ala Leu Leu
            1605                1610                1615

Ser Gly Pro Gln Ala Ser Lys Thr Glu Leu Pro Ser Pro Glu Ser Ala
      1620                1625                1630

Gln Ser Pro Ser Pro Ser Gly Asp Val Arg Ala Ser Val Pro Pro Val
      1635                1640                1645

Leu Pro Ser Ser Ser Gly Lys Lys Asn Asp Thr Thr Ser Ala Arg Glu
      1650                1655                1660

Leu Ser Pro Ser Ser Leu Lys Met Asn Lys Ser Tyr Leu Leu Glu Pro
1665                1670                1675                1680

Trp Phe Leu Pro Pro Ser Arg Gly Leu Gln Asn Ser Pro Ala Val Ser
            1685                1690                1695

Leu Pro Asp Pro Glu Phe Lys Arg Asp Arg Lys Gly Pro His Pro Thr
            1700                1705                1710

Ala Arg Ser Pro Gly Thr Val Met Glu Ser Asn Pro Gln Gln Arg Glu
      1715                1720                1725

Gly Ser Ser Pro Lys His Gln Asp His Thr Thr Asp Pro Lys Leu Leu
      1730                1735                1740

Thr Cys Leu Gly Gln Asn Leu His Ser Pro Asp Leu Ala Arg Pro Arg
1745                1750                1755                1760

Cys Pro Leu Pro Pro Glu Ala Ser Pro Ser Arg Glu Lys Pro Gly Leu
            1765                1770                1775

Arg Glu Ser Ser Glu Arg Gly Pro Pro Thr Ala Arg Ser Glu Arg Ser
      1780                1785                1790

```
Ala Ala Arg Ala Asp Thr Cys Arg Glu Pro Ser Met Glu Leu Cys Phe
            1795                1800                1805

Pro Glu Thr Ala Lys Thr Ser Asp Asn Ser Lys Asn Leu Leu Ser Val
    1810                1815                1820

Gly Arg Thr His Pro Asp Phe Tyr Thr Gln Thr Gln Ala Met Glu Lys
1825                1830                1835                1840

Ala Trp Ala Pro Gly Gly Lys Thr Asn His Lys Asp Gly Pro Gly Glu
                1845                1850                1855

Ala Arg Pro Pro Pro Arg Asp Asn Ser Ser Leu His Ser Ala Gly Ile
            1860                1865                1870

Pro Cys Glu Lys Glu Leu Gly Lys Val Arg Arg Gly Val Glu Pro Lys
        1875                1880                1885

Pro Glu Ala Leu Leu Ala Arg Arg Ser Leu Gln Pro Pro Gly Ile Glu
    1890                1895                1900

Ser Glu Lys Ser Glu Lys Leu Ser Ser Phe Pro Ser Leu Gln Lys Asp
1905                1910                1915                1920

Gly Ala Lys Glu Pro Glu Arg Lys Glu Gln Pro Leu Gln Arg His Pro
                1925                1930                1935

Ser Ser Ile Pro Pro Pro Pro Leu Thr Ala Lys Asp Leu Ser Ser Pro
            1940                1945                1950

Ala Ala Arg Gln His Cys Ser Ser Pro Ser His Ala Ser Gly Arg Glu
        1955                1960                1965

Pro Gly Ala Lys Pro Ser Thr Ala Glu Pro Ser Ser Ser Pro Gln Asp
    1970                1975                1980

Pro Pro Lys Pro Val Ala Ala His Ser Glu Ser Ser Ser His Lys Pro
1985                1990                1995                2000

Arg Pro Gly Pro Asp Pro Gly Pro Pro Lys Thr Lys His Pro Asp Arg
                2005                2010                2015

Ser Leu Ser Ser Gln Lys Pro Ser Val Gly Ala Thr Lys Gly Lys Glu
            2020                2025                2030

Pro Ala Thr Gln Ser Leu Gly Gly Ser Ser Arg Glu Gly Lys Gly His
        2035                2040                2045

Ser Lys Ser Gly Pro Asp Val Phe Pro Ala Thr Pro Gly Ser Gln Asn
    2050                2055                2060

Lys Ala Ser Asp Gly Ile Gly Gln Gly Glu Gly Gly Pro Ser Val Pro
2065                2070                2075                2080

Leu His Thr Asp Arg Ala Pro Leu Asp Ala Lys Pro Gln Pro Thr Ser
                2085                2090                2095

Gly Gly Arg Pro Leu Glu Val Leu Glu Lys Pro Val His Leu Pro Arg
            2100                2105                2110

Pro Gly His Pro Gly Pro Ser Glu Pro Ala Asp Gln Lys Leu Ser Ala
        2115                2120                2125

Val Gly Glu Lys Gln Thr Leu Ser Pro Lys His Pro Lys Pro Ser Thr
    2130                2135                2140

Val Lys Asp Cys Pro Thr Leu Cys Lys Gln Thr Asp Asn Arg Gln Thr
2145                2150                2155                2160

Asp Lys Ser Pro Ser Gln Pro Ala Ala Asn Thr Asp Arg Arg Ala Glu
                2165                2170                2175

Gly Lys Lys Cys Thr Glu Ala Leu Tyr Ala Pro Ala Glu Gly Asp Lys
            2180                2185                2190

Leu Glu Ala Gly Leu Ser Phe Val His Ser Glu Asn Arg Leu Lys Gly
        2195                2200                2205
```

```
Ala Glu Arg Pro Ala Ala Gly Val Gly Lys Gly Phe Pro Glu Ala Arg
    2210                2215                2220

Gly Lys Gly Pro Gly Pro Gln Lys Pro Pro Thr Glu Ala Asp Lys Pro
2225                2230                2235                2240

Asn Gly Met Lys Arg Ser Pro Ser Ala Thr Gly Gln Ser Ser Phe Arg
            2245                2250                2255

Ser Thr Ala Leu Pro Glu Lys Ser Leu Ser Cys Ser Ser Ser Phe Pro
        2260                2265                2270

Glu Thr Arg Ala Gly Val Arg Glu Ala Ser Ala Ser Ser Asp Thr
        2275                2280                2285

Ser Ser Ala Lys Ala Ala Gly Gly Met Leu Glu Leu Pro Ala Pro Ser
    2290                2295                2300

Asn Arg Asp His Arg Lys Ala Gln Pro Ala Gly Glu Gly Arg Thr His
2305                2310                2315                2320

Met Thr Lys Ser Asp Ser Leu Pro Ser Phe Arg Val Ser Thr Leu Pro
            2325                2330                2335

Leu Glu Ser His His Pro Asp Pro Asn Thr Met Gly Gly Ala Ser His
        2340                2345                2350

Arg Asp Arg Ala Leu Ser Val Thr Ala Thr Val Gly Glu Thr Lys Gly
        2355                2360                2365

Lys Asp Pro Ala Pro Ala Gln Pro Pro Pro Ala Arg Lys Gln Asn Val
    2370                2375                2380

Gly Arg Asp Val Thr Lys Pro Ser Pro Ala Pro Asn Thr Asp Arg Pro
2385                2390                2395                2400

Ile Ser Leu Ser Asn Glu Lys Asp Phe Val Val Arg Gln Arg Gly
            2405                2410                2415

Lys Glu Ser Leu Arg Ser Ser Pro His Lys Lys Ala Leu
        2420                2425

<210> SEQ ID NO 8
<211> LENGTH: 7305
<212> TYPE: DNA
<213> ORGANISM: Homo sapiens

<400> SEQUENCE: 8
atggatgagt ccagcattct aagacgaaga gggctccaga aggagctgag tctccccaga    60
agaggaagtt tgatagattc ccagaagtgg aattgcttgg tcaaacgttg ccgaacaagc   120
aaccggaaaa gcttaatagg caatgggcag tcaccagcat tgcctcgacc acactcacct   180
ctctctgctc atgcaggaaa tagccctcaa gatagtccaa gaaatttctc ccccagtgcc   240
tcagcccatt tttcatttgc acggaggact gatggacgcc gctggtcgtt ggcttctctc   300
ccttcctctg ctatgggac aaacacaccc agctctacgg tctcttcatc ctgttcctcc   360
caggagaagt tgcatcagtt accataccaa ccaacaccag acgagttaca cttcttatca   420
aaacatttct gtaccaccga aagcatcgcc actgagaaca gatgcaggaa cacgccgatg   480 cgccccccgtt cccgaagtct gagccctgga cgttctcccg cctgctgtga ccatgaaata   540
attatgatga accatgtcta caaagaaagg ttcccaaagg ctacagctca gatggaagaa   600
cgtctaaagg aaattatcac cagctactct cctgacaacg ttctacccct agcagatgga   660
gtgcttagtt tcactcacca ccagattatt gaactggctc gagattgctt ggataaatcc   720
caccagggcc tcatcacctc acgatacttc cttgaattac agcacaaatt agataagttg   780
ctacaggagg ctcatgatcg ttcagaaagt ggagaattgg catttattaa caactagtt    840 cgaaagatcc taattgttat tgcccgccct gctcggttat tagagtgcct ggaatttgat   900
```

```
ccggaagaat tttactacct attggaagca gcagaaggcc atgccaaaga aggacagggt    960
attaaaaccg acattcccag gtacatcatt agccaactgg gactcaataa ggatcccttg   1020
gaagaaatgg ctcatttggg aaactacgat agtgggacag cagaaacacc agaaacagat   1080
gaatcagtga gtagctctaa tgcctccctg aaacttcgaa ggaaacctcg ggaaagtgat   1140
tttgaaacga ttaaattgat tagcaatgga gcctatgggg cagtctactt tgttcggcat   1200
aaagaatccc ggcagaggtt tgccatgaag aagattaata acagaacct catccttcga    1260
aaccagatcc agcaggcctt tgtggagcgg gatatcctga cttttgcaga aaaccccttt   1320
gttgtcagca tgtattgctc ctttgaaaca aggcgccact gtgcatggt catgaaatat    1380
gtggaagggg gagactgtgc tactttaatg aaaaacatgg gtcctctccc tgttgatatg   1440
gccagaatgt actttgctga gacggtcttg gccttggaat atttacataa ttatggaatt   1500
gtacacaggg atttgaaacc agacaacttg ttggttacct ccatggggca cataaagctg   1560
acagattttg gattatctaa ggtgggacta atgagcatga ctaccaacct ttacgagggt   1620
catattgaga aggatgctag agagttcctg gataaacagg tctgtggcac acctgaatac   1680
attgcaccag aagtgattct gaggcagggt tatggaaagc cggtggactg gtgggccatg   1740
gggattatcc tctatgaatt tctggttgga tgcgtgccat tctttgggga tactccagag   1800
gagctatttg acaagtcat cagtgatgag atcaactggc ctgagaagga tgaggcaccc    1860
ccacctgatg cccaggatct gattaccttta ctcctcaggc agaatcccct ggagaggctg   1920
ggaacaggtg gtgcatatga agtcaaacag catcgattct tccgttcttt agactggaac   1980
agtttgctga acagaaggc agaatttatt ccccaactgg aatctgagga tgacacaagt    2040
tattttgata ctcggtctga gaagtatcat catatggaaa cggaggaaga agatgacaca   2100
aatgatgaag actttaatgt ggaaataagg cagttttctt catgttcaca caggttttca   2160
aaagttttca gcagtataga tcgaatcact cagaattcag cagaagagaa ggaagactct   2220
gtggacaaaa ccaaaagcac caccttgcca tccacagaaa cactgagctg gagttcagaa   2280
tattctgaaa tgcaacagct atcaacatcc aactcttcag atactgaaag caacagacat   2340
aaactcagtt ctggcctact tcccaaactg gctatttcaa cagagggaga gcaagatgaa   2400
gctgcctcct gccctggaga ccccatgag gagccaggaa agccagccct tcctcctgaa    2460
gagtgtgccc aggaggagcc tgaggtcacc accccagcca gcaccatcag cagctccacc   2520
ctgtcagttg gcagttttc agagcacttg gatcagataa atggacgaag cgagtgtgtg   2580
gacagtacag ataattcctc aaagccatcc agtgaacccg cttctcacat ggctcggcag   2640
cgattagaaa gcacagaaaa aagaaaatc tcggggaaag tcacaaagtc cctctctgcc    2700
agtgctcttt ccctcatgat cccaggagat atgtttgctg tttcccctct gggaagtcca   2760
atgtctcccc attccctgtc ctcggaccct tcttcttcac gagattcctc tcccagccga   2820
gattcctcag cagcttctgc cagtccacat cagccgattg tgatccacag ttcggggaag   2880
aactacggct ttaccatccg agccatccgg gtgtatgtgg agacagtga catctataca    2940
gtgcaccata tcgtctggaa tgtagaagaa ggaagtccgg catgccaggc aggactgaag   3000
gctggagatc ttatcactca catcaatgga gaaccagtgc atggacttgt ccacacagaa   3060
gttatagaac tcctactgaa gagtgggaat aaggtgtcaa tcactactac cccatttgaa   3120
aacacatcaa tcaaaactgg accagccag agaaacagct ataagagccg gatggtgagg    3180
cggagcaaga atccaagaa gaaagaaagt ctcgaaagga ggagatctct ttcaaaaag    3240
ctagccaagc agccttctcc tttactccac accagccgaa gtttctcctg cttgaacaga   3300
```

```
tccctgtcat cgggtgagag cctcccaggt tcccccactc atagcttgtc tccccggtct   3360
ccaacaccaa gctaccgctc cacccctgac ttcccatctg gtactaattc ctcccagagc   3420
agctccccta gttctagtgc ccccaattcc ccagcagggt ccgggcacat ccggcccagc   3480
actctccacg gtcttgcacc caaactcggc gggcagcggt accggtccgg aaggcgaaag   3540
tccgccggca acatcccact gtccccgctg gcccggacgc cctctccaac cccgcaaccc   3600
acctccccgc agcggtcacc atcccctctt ctgggacact cactgggcaa ttccaagatc   3660
gcgcaagcct ttcccagcaa gatgcactcc ccgcccacca tcgtcagaca catcgtgagg   3720
cccaagagtg cggagccccc caggtccccg ctgctcaagc gcgtgcagtc cgaggagaag   3780
ctgtcgccct cttacggcag tgacaagaag cacctgtgct cccgcaagca cagcctggag   3840
gtgacccaag aggaggtgca gcgggagcag tcccagcggg aggcgccgct gcagagcctg   3900
gatgagaacg tgtgcgacgt gccgccgctc agccgcgccc ggccagtgga gcaaggctgc   3960
ctgaaacgcc cagtctcccg gaaggtgggc cgccaggagt ctgtggacga cctggaccgc   4020
gacaagctga aggccaaggt ggtggtgaag aaagcagacg gcttcccaga gaaacaggaa   4080
tcccaccaga aatcccatgg acccgggagt gatttggaaa actttgctct gtttaagctg   4140
gaagagagag agaagaaagt ctatccgaag gctgtgaaag ggtcaagtac ttttgaaaac   4200
aaagcgtcta tgcaggaggc gccaccgctg ggcagcctgc tgaaggatgc tcttcacaag   4260
caggccagcg tgcgcgccag cgagggtgcg atgtcggatg ccgggtgcc tgcggagcac   4320
cgccagggtg cgggggactt cagacgggcc cccgctcctg gcaccctcca ggatggtctc   4380
tgccactccc tcgacagggg catctctggg aaggggggaag gcacggagaa gtcctcccag   4440
gccaaggagc ttctccgatg tgaaaagtta gacagcaagc tggccaacat cgattacctc   4500
cgaaagaaaa tgtcacttga ggacaaagag gacaacctct gccctgtgct gaagcccaag   4560
atgacagctg gctcccacga atgcctgcca gggaacccag tccgacccac gggtgggcag   4620
caggagcccc cgccggcttc tgagagccga gcttttgtca gcagcaccca tgcagctcag   4680
atgagtgccg tctcttttgt tcccctcaag gccttaacag gccgggtgga cagtggaacg   4740
gagaagcctg gcttggttgc tcctgagtcc cctgttagga agagccccctc cgagtataag   4800
ctggaaggta ggtctgtctc atgcctgaag ccgatcgagg gcactctgga cattgctctc   4860
ctgtccggac ctcaggcctc caagacagaa ctgccttccc cagagtctgc acagagcccc   4920
agcccaagtg gtgacgtgag ggcctctgtg ccaccagttc tccccagcag cagtgggaaa   4980
aagaacgata ccaccagtgc aagagagctt tctccttcca gcttaaagat gaataaatcc   5040
tacctgctgg agccttggtt cctgcccccc agccgaggtc tccagaattc accagcagtt   5100
tccctgcctg acccagagtt caagagggac aggaaaggtc cccatcctac tgccaggagc   5160
cctggaacag tcatggaaag caatccccaa cagagagagg gcagctcccc taaacaccaa   5220
gaccacacca ctgaccccaa gcttctgacc tgcctggggc agaacctcca cagccctgac   5280
ctggccaggc cacgctgccc gctcccacct gaagcttccc cctcaaggga agccaggc    5340
ctgagggaat cgtctgaaag aggccctccc acagccagaa gcgagcgctc tgctgcgagg   5400
gctgacacat gcagagagcc ctccatggaa ctgtgctttc cagaaactgc gaaaaccagt   5460
gacaactcca aaaatctcct ctctgtggga aggacccacc cagatttcta tacacagacc   5520
caggccatgg agaaagcatg ggcgccgggt gggaaaacga accacaaaga tggcccaggt   5580
gaggcgaggc ccccgcccag agacaactcc tctctgcact cagctggaat tcctgtgag   5640
aaggagctgg gcaaggtgag gcgtggcgtg gaacccaagc ccgaagcgct tcttgccagg   5700
```

```
cggtctctgc agccacctgg aattgagagt gagaagagtg aaaagctctc cagtttccca    5760
tctttgcaga aagatggtgc caaggaacct gaaaggaagg agcagcctct acaaaggcat    5820
cccagcagca tccctccgcc ccctctgacg gccaaagacc tgtccagccc ggctgccagg    5880
cagcattgca gttccccaag ccacgcttct ggcagagagc cgggggccaa gcccagcact    5940
gcagagccca gctcgagccc ccaggaccct cccaagcctg ttgctgcgca cagtgaaagc    6000
agcagccaca agccccggcc tggccctgac ccggggccctc caaagactaa gcaccccgac    6060
cggtccctct cctctcagaa accaagtgtc ggggccacaa agggcaaaga gcctgccact    6120
cagtccctcg gtggctctag cagagagggg aagggccaca gtaagagtgg gccggatgtg    6180
tttcctgcta ccccaggctc ccagaacaaa gccagcgatg ggattggcca gggagaaggt    6240
gggccctctg tcccactgca cactgacagg gctcctctag acgccaagcc acaacccacc    6300
agtggtgggc ggcccctgga ggtgctggag aagcctgtgc atttgccaag gccgggacac    6360
ccagggccta gtgagccagc ggaccagaaa ctgtccgctg ttggtgaaaa gcaaaccctg    6420
tctccaaagc accccaaacc atccactgtg aaagattgcc ccaccctgtg caaacagaca    6480
gacaacagac agacagacaa agcccgagt cagccggccg ccaacaccga cagaagggcg    6540
gaagggaaga aatgcactga agcactttat gctccagcag agggcgacaa gctcgaggcc    6600
ggcctttcct ttgtgcatag cgagaaccgg ttgaaaggcg cggagcggcc agccgcgggg    6660
gtggggaagg gcttccctga ggccagaggg aaagggcccg gtccccagaa gccaccgacg    6720
gaggcagaca agcccaatgg catgaaacgg tcccctcag ccactgggca gagttctttc    6780
cgatccacgg ccctccggga aaagtctctg agctgctcct ccagcttccc tgaaaccagg    6840
gccggagtta gagaggcctc tgcagccagc agcgacacct cttctgccaa ggccgccggg    6900
ggcatgctgg agcttccagc ccccagcaac agggaccata ggaaggctca gcctgccggg    6960
gagggccgaa cccacatgac aaagagtgac tccctgccct ccttccgggt ctccaccctg    7020
cctctggagt cacaccaccc cgacccaaac accatgggcg gggccagcca ccgggacagg    7080
gctctctcgg tgactgccac cgtaggggaa accaaaggga aggaccctgc cccagcccag    7140
cctcccccag ctaggaaaca gaacgtgggc agagacgtga ccaagccatc cccagcccca    7200
aacactgacc gccccatctc tctttctaat gagaaggact ttgtggtacg gcagaggcgg    7260
gggaaagaga gtttgcgtag cagccctcac aaaaaggcct tgtaa                   7305
```

<210> SEQ ID NO 9
<211> LENGTH: 753
<212> TYPE: DNA
<213> ORGANISM: Homo sapiens

<400> SEQUENCE: 9

```
atgggggaga aagtttcgga ggcgccagag ccggtgcccc gcggctgcag tggccacggc      60
agccggactc cagcctctgc gctggtcgcc gcgtcctctc cgggtgcttc ctcggccgag     120
tcctcctcgg gctcagaaac tctgtcgcga gaaggggagc ccggcggctt ctccagagag     180
catcagccgc cgccgccgcc gccgttggga ggcaccctgg gcgccccgggc cccgccgcg     240 tgggctccgg caagcgtgct gctggagcgc ggagtccttg cgctgccgcc gccgcttccc     300
ggaggagctg tgccgccgc gccccggggc agcagcgcgt cccaggagga gcaggacgag     360
gagcttgacc acatattatc ccctccaccc atgccgtttc ggaaatgcag caacccagat     420
gtggcttctg gccctggaaa atcactgaag tataaaagac agctgagtga ggatggaaga     480
cagctaaggc gagggagcct gggaggagcc ctgactggga ggtaccttct tccaaacccg     540
```

-continued

| | |
|---|---|
| gtggcgggac aggcctggcc ggcctctgca gagacgtcca acctcgtgcg catgcgcagc | 600 |
| caggccctgg gccagtcggc gccctcgctc accgccagcc tgaaggagct gagtctcccc | 660 |
| agaagaggaa gtttgataga ttcccagaag tggaattgct tggtcaaacg ccctgtgtgt | 720 |
| ccaaatgctg ggagaacatc accccttgga tga | 753 |

<210> SEQ ID NO 10
<211> LENGTH: 7872
<212> TYPE: DNA
<213> ORGANISM: Homo sapiens

<400> SEQUENCE: 10

| | |
|---|---|
| atgggggaga agtttcgga ggcgccagag ccggtgcccc gcggctgcag tggccacggc | 60 |
| agccggactc cagcctctgc gctggtcgcc gcgtcctctc cgggtgcttc ctcggccgag | 120 |
| tcctcctcgg gctcagaaac tctgtcggag aaggggagc ccggcggctt ctccagagag | 180 |
| catcagccgc cgccgccgcc gccgttggga ggcaccctgg gcgcccgggc gcccgccgcg | 240 |
| tgggctccgg caagcgtgct gctggagcgc ggagtccttg cgctgccgcc gccgcttccc | 300 |
| ggaggagctg tgccgcccgc gccccggggc agcagcgcgt cccaggagga gcaggacgag | 360 |
| gagcttgacc acatattatc ccctccaccc atgccgtttc ggaaatgcag caacccagat | 420 |
| gtggcttctg gccctggaaa atcactgaag tataaaagac agctgagtga ggatggaaga | 480 |
| cagctaaggc gagggagcct ggaggagcc ctgactggga ggtaccttct tccaaacccg | 540 |
| gtggcgggac aggcctggcc ggcctctgca gagacgtcca acctcgtgcg catgcgcagc | 600 |
| caggccctgg gccagtcggc gccctcgctc accgccagcc tgaaggagct gagtctcccc | 660 |
| agaagaggaa gtttttgccg aacaagcaac cggaaaagct taataggcaa tgggcagtca | 720 |
| ccagcattgc ctcgaccaca ctcacctctc tctgctcatg caggaaatag ccctcaagat | 780 |
| agtccaagaa atttctcccc cagtgcctca gcccattttt catttgcacg gaggactgat | 840 |
| ggacgccgct ggtcgttggc ttctctccct tcctctggct atgggacaaa cacacccagc | 900 |
| tctacggtct cttcatcctg ttcctcccag gagaagttgc atcagttacc ataccaacca | 960 |
| acaccagacg agttacactt cttatcaaaa catttctgta ccaccgaaag catcgccact | 1020 |
| gagaacagat gcaggaacac gccgatgcgc cccgttccc gaagtctgag ccctggacgt | 1080 |
| tctcccgcct gctgtgacca tgaaataatt atgatgaacc atgtctacaa agaaaggttc | 1140 |
| ccaaaggcta cagctcagat ggaagaacgt ctaaaggaaa ttatcaccag ctactctcct | 1200 |
| gacaacgttc taccccttagc agatggagtg cttagtttca ctcaccacca gattattgaa | 1260 |
| ctggctcgag attgcttgga taaatcccac cagggcctca tcacctcacg atacttcctt | 1320 |
| gaattacagc acaaattaga taagttgcta caggaggctc atgatcgttc agaaagtgga | 1380 |
| gaattggcat ttattaaaca actagttcga aagatcctaa ttgttattgc ccgccctgct | 1440 |
| cggttattag agtgcctgga atttgatccg gaagaatttt actacctatt ggaagcagca | 1500 |
| gaaggccatg ccaaagaagg acagggtatt aaaaccgaca ttcccaggta catcattagc | 1560 |
| caactgggac tcaataagga tcccttggaa gaaatggctc atttgggaaa ctacgatagt | 1620 |
| gggacagcag aaacaccaga aacagatgaa tcagtgagta gctctaatgc ctccctgaaa | 1680 |
| cttcgaagga aacctcggga aagtgatttt gaaacgatta aattgattag caatggagcc | 1740 |
| tatgggggcag tctactttgt tcggcataaa gaatcccggc agaggtttgc catgaagaag | 1800 |
| attaataaac agaacctcat ccttcgaaac cagatccagc aggcctttgt ggagcggat | 1860 |
| atcctgactt ttgcagaaaa ccccctttgtt gtcagcatgt attgctcctt tgaaacaagg | 1920 |

-continued

```
cgccacttgt gcatggtcat ggaatatgtg aagggggag actgtgctac tttaatgaaa    1980
aacatgggtc ctctccctgt tgatatggcc agaatgtact ttgctgagac ggtcttggcc    2040
ttggaatatt tacataatta tggaattgta cacagggatt tgaaaccaga caacttgttg    2100
gttacctcca tggggcacat aaagctgaca gattttggat tatctaaggt gggactaatg    2160
agcatgacta ccaaccttta cgagggtcat attgagaagg atgctagaga gttcctggat    2220
aaacaggtct gtggcacacc tgaatacatt gcaccagaag tgattctgag cagggttat    2280 ggaaagccgg tggactggtg gccatgggg attatcctct atgaatttct ggttggatgc    2340
gtgccattct ttggggatac tccagaggag ctatttggac aagtcatcag tgatgagatc    2400
aactggcctg agaaggatga ggcacccca cctgatgccc aggatctgat taccttactc    2460
ctcaggcaga atccctgga gaggctggga acaggtggtg catatgaagt caaacagcat    2520
cgattcttcc gttctttaga ctggaacagt ttgctgagac agaaggcaga atttattccc    2580
caactggaat ctgaggatga cacaagttat tttgatactc ggtctgagaa gtatcatcat    2640
atggaaacgg aggaagaaga tgacacaaat gatgaagact taatgtgga aataaggcag    2700 ttttcttcat gttcacacag ttttcaaaa gttttcagca gtatagatcg aatcactcag    2760
aattcagcag aagagaagga agactctgtg gacaaaacca aaagcaccac cttgccatcc    2820
acagaaacac tgagctggag ttcagaatat tctgaaatgc aacagctatc aacatccaac    2880
tcttcagata ctgaaagcaa cagacataaa ctcagttctg cctacttcc caaactggct    2940 atttcaacag agggagagca agatgaagct gcctcctgcc ctggagaccc ccatgaggag    3000
ccaggaaagc cagcccttcc tcctgaagag tgtgcccagg aggagcctga ggtcaccacc    3060
ccagccagca ccatcagcag ctccacccctg tcagttggca gttttcaga gcacttggat    3120 cagataaatg gacgaagcga gtgtgtggac agtacagata attcctcaaa gccatccagt    3180
gaacccgctt ctcacatggc tcggcagcga ttagaaagca cagaaaaaaa gaaaatctcg    3240
gggaaagtca caaagtccct ctctgccagt gctctttccc tcatgatccc aggagatatg    3300
tttgctgttt ccctctgg aagtccaatg tctccccatt ccctgtcctc ggacccttct    3360
tcttcacgag attcctctcc cagccgagat tcctcagcag cttctgccag tccacatcag    3420
ccgattgtga tccacagttc ggggaagaac tacggcttta ccatccgagc catccgggtg    3480
tatgtgggag acagtgacat ctatacagtg caccatatcg tctggaatgt agaagaagga    3540
agtccggcat gccaggcagg actgaaggct ggagatctta tcactcacat caatggagaa    3600
ccagtgcatg gacttgtcca cacagaagtt atagaactcc tactgaagag tgggaataag    3660
gtgtcaatca ctactacccc atttgaaaac acatcaatca aaactggacc agccaggaga    3720
aacagctata agagccggat ggtgaggcgg agcaagaaat ccaagaagaa agaaagtctc    3780
gaaaggagga gatctctttt caaaaagcta gccaagcagc cttctccttt actccacacc    3840
agccgaagtt tctcctgctt gaacagatcc ctgtcatcgg gtgagagcct cccaggttcc    3900
cccactcata gcttgtctcc ccggtctcca acaccaagct accgctccac ccctgacttc    3960
ccatctggta ctaattcctc ccagagcagc tcccctagtt ctagtgcccc caattcccca    4020
gcagggtccg gcacatccg gcccagcact tccacggtc ttgcacccaa actcggcggg    4080
cagcggtacc ggtccggaag gcgaaagtcc gccggcaaca tcccactgtc cccgctggcc    4140
cggacgccct ctccaacccc gcaacccacc tcccgcagc ggtcaccatc ccctcttctg    4200
ggacactcac tgggcaattc caagatcgcg caagcctttc ccagcaagat gcactccccg    4260
cccaccatcg tcagacacat cgtgaggccc aagagtgcgg agccccccag gtccccgctg    4320
```

```
ctcaagcgcg tgcagtccga ggagaagctg tcgccctctt acggcagtga caagaagcac    4380
ctgtgctccc gcaagcacag cctggaggtg acccaagagg aggtgcagcg ggagcagtcc    4440
cagcgggagg cgccgctgca gagcctggat gagaacgtgt gcgacgtgcc gccgctcagc    4500
cgcgcccggc cagtggagca aggctgcctg aaacgcccag tctcccggaa ggtgggccgc    4560
caggagtctg tggacgacct ggaccgcgac aagctgaagg ccaaggtggt ggtgaagaaa    4620
gcagacggct tcccagagaa acaggaatcc caccagaaat cccatggacc cgggagtgat    4680
ttggaaaact ttgctctgtt taagctggaa gagagagaga agaaagtcta tccgaaggct    4740
gtggaaaggt caagtacttt tgaaaacaaa gcgtctatgc aggaggcgcc accgctgggc    4800
agcctgctga aggatgctct tcacaagcag gccagcgtgc gcgccagcga gggtgcgatg    4860
tcggatggcc gggtgcctgc ggagcaccgc cagggtggcg gggacttcag acggccccc     4920
gctcctggca ccctccagga tggtctctgc cactccctcg acaggggcat ctctgggaag    4980
ggggaaggca cggagaagtc ctcccaggcc aaggagcttc tccgatgtga aaagttagac    5040
agcaagctgg ccaacatcga ttacctccga agaaaatgt cacttgagga caaagaggac     5100
aacctctgcc ctgtgctgaa gcccaagatg acagctggct cccacgaatg cctgccaggg    5160
aacccagtcc gacccacggg tgggcagcag gagccccgc cggcttctga gagccgagct     5220
tttgtcagca gcacccatgc agctcagatg agtgccgtct cttttgttcc cctcaaggcc    5280
ttaacaggcc gggtggacag tggaacggag aagcctggct tggttgctcc tgagtcccct    5340
gttaggaaga gcccctccga gtataagctg gaaggtaggt ctgtctcatg cctgaagccg    5400
atcgagggca ctctggacat tgctctcctg tccggacctc aggcctccaa gacagaactg    5460
ccttccccag agtctgcaca gagccccagc ccaagtggtg acgtgagggc ctctgtgcca    5520
ccagttctcc ccagcagcag tgggaaaaag aacgataacc ccagtgcaag agagcttttct   5580
ccttccagct taaagatgaa taaatcctac ctgctggagc cttggttcct gcccccagc     5640
cgaggtctcc agaattcacc agcagtttcc ctgcctgacc cagagttcaa gagggacagg    5700
aaaggtcccc atcctactgc caggagccct ggaacagtca tggaaagcaa tccccaacag    5760
agagagggca gctcccctaa acaccaagac cacaccactg accccaagct tctgacctgc    5820
ctggggcaga acctccacag ccctgacctg gccaggccac gctgcccgct cccacctgaa    5880
gcttcccct caaggagaa gccaggcctg agggaatcgt ctgaaagagg ccctcccaca      5940
gccagaagcg agcgctctgc tgcgagggct gacacatgca gagagccctc catggaactg    6000
tgctttccag aaactgcgaa aaccagtgac aactccaaaa atctcctctc tgtgggaagg    6060
acccacccag atttctatac acagacccag gccatggaga aagcatgggc gccgggtggg    6120
aaaacgaacc acaaagatgg cccaggtgag gcgaggcccc cgcccagaga caactcctct    6180
ctgcactcag ctggaattcc ctgtgagaag gagctgggca aggtgaggcg tggcgtggaa    6240
cccaagcccg aagcgcttct tgccaggcgg tctctgcagc cacctggaat tgagagtgag    6300
aagagtgaaa agctctccag tttcccatct ttgcagaaag atggtgccaa ggaacctgaa    6360
aggaaggagc agcctctaca aaggcatccc agcagcatcc ctccgccccc tctgacggcc    6420
aaagacctgt ccagcccggc tgccaggcag cattgcagtt ccccaagcca cgcttctggc    6480
agagagccgg gggccaagcc cagcactgca gagcccagct cgagccccca ggaccctccc    6540
aagcctgttg ctgcgcacag tgaaagcagc agccacaagc cccggcctgg ccctgacccg    6600
ggccctccaa agactaagca ccccgaccgg tccctctcct ctcagaaacc aagtgtcggg    6660
gccacaaagg gcaaagagcc tgccactcag tccctcggtg gctctagcag agaggggaag    6720
```

```
ggccacagta agagtgggcc ggatgtgttt cctgctaccc caggctccca gaacaaagcc    6780
agcgatggga ttggccaggg agaaggtggg ccctctgtcc cactgcacac tgacagggct    6840
cctctagacg ccaagccaca acccaccagt ggtgggcggc ccctggaggt gctggagaag    6900
cctgtgcatt tgccaaggcc gggacaccca gggcctagtg agccagcgga ccagaaactg    6960
tccgctgttg gtgaaaagca aaccctgtct ccaaagcacc caaaccatc cactgtgaaa    7020 gattgcccca ccctgtgcaa acagacagac aacagacaga cagacaaaag cccgagtcag    7080
ccggccgcca acaccgacag aagggcggaa gggaagaaat gcactgaagc actttatgct    7140
ccagcagagg gcgacaagct cgaggccggc ctttcctttg tgcatagcga gaaccggttg    7200
aaaggcgcgg agcggccagc cgcggggggtg gggaaggggct tccctgaggc cagagggaaa    7260
gggcccggtc cccagaagcc accgacgag gcagacaagc caatggcat gaaacggtcc    7320 ccctcagcca ctgggcagag ttctttccga tccacggccc tcccggaaaa gtctctgagc    7380
tgctcctcca gcttccctga accagggcc ggagttagag aggcctctgc agccagcagc    7440
gacacctctt ctgccaaggc cgccgggggc atgctggagc ttccagcccc cagcaacagg    7500
gaccatagga aggctcagcc tgccggggag ggccgaaccc acatgacaaa gagtgactcc    7560
ctgccctcct tccgggtctc caccctgcct ctggagtcac accaccccga cccaaacacc    7620
atgggcgggg ccagccaccg ggacagggct ctctcggtga ctgccaccgt aggggaaacc    7680
aaagggaagg accctgcccc agcccagcct cccccagcta ggaaacagaa cgtgggcaga    7740
gacgtgacca agccatcccc agccccaaac actgaccgcc ccatctctct ttctaatgag    7800
aaggactttg tggtacggca gaggcgggggg aagagagtt tgcgtagcag ccctcacaaa    7860
aaggccttgt aa                                                        7872
```

<210> SEQ ID NO 11
<211> LENGTH: 7254
<212> TYPE: DNA
<213> ORGANISM: Homo sapiens

<400> SEQUENCE: 11

```
atgaaagccc agcgggaaag gctacagatt ccggggctga ccttggattg ccgaacaagc      60
aaccggaaaa gcttaatagg caatgggcag tcaccagcat tgcctcgacc acactcacct     120
ctctctgctc atgcaggaaa tagccctcaa gatagtccaa gaaatttctc ccccagtgcc     180
tcagcccatt tttcatttgc acggagaaat gacaggactg atggacgccg ctggtcgttg     240
gcttctctcc cttcctctgg ctatgggaca aacacaccca gctctacggt ctcttcatcc     300
tgttcctccc aggagaagtt gcatcagtta ccataccaac caacaccaga cgagttacac     360
ttcttatcaa acatttctg taccaccgaa agcatcgcca ctgagaacag atgcaggaac     420
acgccgatgc gcccccgttc ccgaagtctg agccctggac gttctccgc ctgctgtgac     480 catgaaataa ttatgatgaa ccatgtctac aaagaaaggt tcccaaaggc tacagctcag     540
atggaagaac gtctaaagga aattatcacc agctactctc ctgacaacgt tctacccttg     600
gcagatggag tgcttagttt cactcaccac cagattattg aactggctcg agattgcttg     660
gataaatccc accagggcct catcacctca cgatacttcc ttgaattaca gcacaaatta     720
gataagttgc tacaggaggc tcatgatcgt tcagaaagtg gagaattggc atttattaaa     780
caactagttc gaaagatcct aattgttatt gcccgccctg ctcggttatt agagtgcctg     840
gaatttgatc cggaagaatt ttactaccta ttggaagcag cagaaggcca tgccaaagaa     900
ggacagggta ttaaaaccga cattcccagg tacatcatta gccaactggg actcaataag     960
```

-continued

```
gatcccttgg aagaaatggc tcatttggga aactacgata gtgggacagc agaaacacca    1020
gaaacagatg aatcagtgag tagctctaat gcctccctga aacttcgaag gaaacctcgg    1080
gaaagtgatt ttgaaacgat taaattgatt agcaatggag cctatggggc agtctacttt    1140
gttcggcata agaatcccg gcagaggttt gccatgaaga agattaataa acagaacctc     1200
atccttcgaa accagatcca gcaggccttt gtggagcggg atatcctgac ttttgcagaa    1260 aaccccttg ttgtcagcat gtattgctcc tttgaaacaa ggcgccactt gtgcatggtc     1320
atggaatatg tggaagggg agactgtgct actttaatga aaaacatggg tcctctccct    1380
gttgatatgg ccagaatgta ctttgctgag acggtcttgg ccttggaata tttacataat    1440
tatggaattg tacacaggga tttgaaacca gacaacttgt tggttacctc catggggcac    1500
ataaagctga cagattttgg attatctaag gtgggactaa tgagcatgac taccaacctt    1560
tacgagggtc atattgagaa ggatgctaga gagttcctgg ataaacaggt ctgtggcaca    1620
cctgaataca ttgcaccaga agtgattctg aggcagggtt atggaaagcc ggtggactgg    1680
tgggccatgg ggattatcct ctatgaattt ctggttggat gcgtgccatt ctttggggat    1740
actccagagg agctatttgg acaagtcatc agtgatgaga tcaactggcc tgagaaggat    1800
gaggcacccc cacctgatgc ccaggatctg attaccttac tcctcaggca gaatcccctg    1860
gagaggctgg gaacaggtgg tgcatatgaa gtcaaacagc atcgattctt ccgttctta    1920 gactggaaca gtttgctgag acagaaggca gaatttattc cccaactgga atctgaggat    1980
gacacaagtt attttgatac tcggtctgag aagtatcatc atatggaaac ggaggaagaa    2040
gatgacacaa atgatgaaga ctttaatgtg gaaataaggc agttttcttc atgttcacac    2100
aggttttcaa aagttttcag cagtatagat cgaatcactc agaattcagc agaagagaag    2160
gaagactctg tggacaaaac caaaagcacc accttgccat ccacagaaac actgagctgg    2220
agttcagaat attctgaaat gcaacagcta tcaacatcca actcttcaga tactgaaagc    2280
aacagacata aactcagttc tggcctactt cccaaactgg ctatttcaac agagggagag    2340
caagatgaag ctgcctcctg ccctggagac ccccatgagg agccaggaaa gccagccctt    2400
cctcctgaag agtgtgccca ggaggagcct gaggtcacca ccccagccag caccatcagc    2460
agctccaccc tgtcagttgg cagttttca gagcacttgg atcagataaa tggacgaagc    2520
gagtgtgtgg acagtacaga taattcctca aagccatcca gtgaacccgc ttctcacatg    2580
gctcggcagc gattagaaag cacagaaaaa aagaaaatct cggggaaagt cacaaagtcc    2640
ctctctgcca gtgctctttc cctcatgatc ccaggagata tgtttgctgt ttcccctctg    2700
ggaagtccaa tgtctcccca ttccctgtcc tcggacccttt cttcttcacg agattcctct    2760
cccagccgag attcctcagc agcttctgcc agtccacatc agccgattgt gatccacagt    2820
tcggggaaga actacggctt taccatccga gccatccggg tgtatgtggg agacagtgac    2880
atctatacag tgcaccatat cgtctggaat gtagaagaag aagtccggc atgccaggca    2940 ggactgaagg ctggagatct tatcactcac atcaatggag aaccagtgca tggacttgtc    3000
cacacagaag ttatagaact cctactgaag agtgggaata aggtgtcaat cactactacc    3060
ccatttgaaa acacatcaat caaaactgga ccagccagga gaaacagcta taagagccgg    3120
atggtgaggc ggagcaagaa atccaagaag aaagaaagtc tcgaaggag gagatctctt    3180 ttcaaaaagc tagccaagca gccttctcct ttactccaca ccagccgaag tttctcctgc    3240
ttgaacagat ccctgtcatc gggtgagagc ctcccaggtt cccccactca tagcttgtct    3300
ccccggtctc aacaccaag ctaccgctcc acccctgact tcccatctgg tactaattcc    3360
```

-continued

```
tcccagagca gctcccctag ttctagtgcc cccaattccc cagcagggtc cgggcacatc    3420
cggcccagca ctctccacgg tcttgcaccc aaactcggcg ggcagcggta ccggtccgga    3480
aggcgaaagt ccgccggcaa catcccactg tccccgctgg cccggacgcc ctctccaacc    3540
ccgcaaccca cctccccgca gcggtcacca tcccctcttc tgggacactc actgggcaat    3600
tccaagatcg cgcaagcctt tcccagcaag atgcactccc cgcccaccat cgtcagacac    3660
atcgtgaggc ccaagagtgc ggagcccccc aggtccccgc tgctcaagcg cgtgcagtcc    3720
gaggagaagc tgtcgccctc ttacggcagt gacaagaagc acctgtgctc ccgcaagcac    3780
agcctggagg tgacccaaga ggaggtgcag cgggagcagt cccagcggga ggcgccgctg    3840
cagagcctgg atgagaacgt gtgcgacgtg ccgccgctca gccgcgcccg gccagtggag    3900
caaggctgcc tgaaacgccc agtctcccgg aaggtgggcc gccaggagtc tgtgacgac    3960 ctggaccgcg acaagctgaa ggccaaggtg gtggtgaaga agcagacgg cttcccagag    4020 aaacaggaat cccaccagaa atcccatgga cccgggagtg atttggaaaa ctttgctctg    4080
tttaagctgg aagagagaga gaagaaagtc tatccgaagg ctgtggaaag gtcaagtact    4140
tttgaaaaca aagcgtctat gcaggaggcg ccaccgctgg gcagcctgct gaaggatgct    4200
cttcacaagc aggccagcgt gcgcgccagc gagggtgcga tgtcggatgg ccgggtgcct    4260
gcggagcacc gccagggtgg cggggacttc agacggcccc ccgctcctgg caccctccag    4320
gatggtctct gccactccct cgacaggggc atctctggga aggggaagg cacggagaag    4380 tcctcccagg ccaaggagct tctccgatgt gaaaagttag acagcaagct ggccaacatc    4440
gattacctcc gaaagaaaat gtcacttgag gacaaagagg acaacctctg ccctgtgctg    4500
aagcccaaga tgacagctgg ctcccacgaa tgcctgccag ggaacccagt ccgacccacg    4560
ggtgggcagc aggagccccc gccggcttct gagagccgag cttttgtcag cagcaccat    4620 gcagctcaga tgagtgccgt ctcttttgtt cccctcaagg ccttaacagg ccgggtggac    4680
agtggaacgg agaagcctgg cttggttgct cctgagtccc ctgttaggaa gagccctcc    4740 gagtataagc tggaaggtag gtctgtctca tgcctgaagc cgatcgaggg cactctggac    4800
attgctctcc tgtccggacc tcaggcctcc aagacagaac tgccttcccc agagtctgca    4860
cagagcccca gccaagtggt gacgtgagg gcctctgtgc caccagttct ccccagcagc    4920
agtgggaaaa agaacgatac caccagtgca agagagcttt ctccttccag cttaaagatg    4980
aataaatcct acctgctgga gccttggttc ctgcccccca gccgaggtct ccagaattca    5040
ccagcagttt ccctgcctga cccagagttc aagagggaca ggaaaggtcc ccatcctact    5100
gccaggagcc ctggaacagt catggaaagc aatccccaac agagagaggg cagctcccct    5160
aaacaccaag accacaccac tgaccccaag cttctgacct gctgggggca gaacctccac    5220
agccctgacc tggccaggcc acgctgcccg ctcccacctg aagcttcccc ctcaagggag    5280
aagccaggcc tgagggaatc gtctgaaaga ggccctccca cagccagaag cgagcgctct    5340
gctgcgaggg ctgacacatg cagagagccc tccatggaac tgtgctttcc agaaactgcg    5400
aaaaccagtg acaactccaa aaatctcctc tctgtgggaa ggacccaccc agatttctat    5460
acacagaccc aggccatgga gaaagcatgg gcgccgggtg ggaaaacgaa ccacaaagat    5520
ggcccaggtg aggcgaggcc cccgcccaga gacaactcct ctctgcactc agctggaatt    5580
ccctgtgaga aggagctggg caaggtgagg cgtggcgtgg aacccaagcc cgaagcgctt    5640
cttgccaggc ggtctctgca gccacctgga attgagagtg agaagagtga aaagctctcc    5700
agtttcccat cttttgcagaa agatggtgcc aaggaacctg aaaggaagga gcagcctcta    5760
```

```
caaaggcatc ccagcagcat ccctccgccc cctctgacgg ccaaagacct gtccagcccg    5820
gctgccaggc agcattgcag ttccccaagc cacgcttctg gcagagagcc gggggccaag    5880
cccagcactg cagagcccag ctcgagcccc caggaccctc ccaagcctgt tgctgcgcac    5940
agtgaaagca gcagccacaa gccccggcct ggccctgacc cgggcccctcc aaagactaag    6000
caccccgacc ggtccctctc ctctcagaaa ccaagtgtcg gggccacaaa gggcaaagag    6060
cctgccactc agtccctcgg tggctctagc agagagggga agggccacag taagagtggg    6120
ccggatgtgt ttcctgctac cccaggctcc cagaacaaag ccagcgatgg gattggccag    6180
ggagaaggtg ggccctctgt cccactgcac actgacaggg ctcctctaga cgccaagcca    6240
caacccacca gtggtgggcg gccctggag gtgctggaga agcctgtgca tttgccaagg    6300
ccgggacacc cagggcctag tgagccagcg gaccagaaac tgtccgctgt tggtgaaaag    6360
caaaccctgt ctccaaagca ccccaaacca tccactgtga agattgccc caccctgtgc    6420
aaacagacag acaacagaca gacagacaaa agcccgagtc agccggccgc caacaccgac    6480
agaagggcgg aagggaagaa atgcactgaa gcactttatg ctccagcaga gggcgacaag    6540
ctcgaggccg gcctttcctt tgtgcatagc gagaaccggt tgaaaggcgc ggagcggcca    6600
gccgcggggg tggggaaggg cttccctgag gccagaggga agggccccgg tccccagaag    6660
ccaccgacgg aggcagacaa gcccaatggc atgaaacggt cccctcagc cactgggcag    6720
agttcttttcc gatccacggc cctccccgaa agtctctga gctgctcctc cagcttccct    6780
gaaaccaggg ccggagttag agaggcctct gcagccagca gcgacacctc ttctgccaag    6840
gccgccgggg gcatgctgga gcttccagcc cccagcaaca gggaccatag gaaggctcag    6900
cctgccgggg agggccgaac ccacatgaca aagagtgact ccctgccctc cttccgggtc    6960
tccaccctgc ctctggagtc acaccacccc gacccaaaca ccatgggcgg ggccagccac    7020
cgggacaggg ctctctcggt gactgccacc gtagggggaaa ccaaagggaa ggaccctgcc    7080
ccagcccagc ctcccccagc taggaaacag aacgtgggca gagacgtgac caagccatcc    7140
ccagccccaa acactgaccg ccccatctct cttttctaatg agaaggactt tgtggtacgg    7200
cagaggcggg ggaaagagag tttgcgtagc agccctcaca aaaaggcctt gtaa           7254
```

<210> SEQ ID NO 12
<211> LENGTH: 7089
<212> TYPE: DNA
<213> ORGANISM: Homo sapiens

<400> SEQUENCE: 12

```
atggatatgt ctgaccccaa ttttttggact gtgctctcaa actttacttt gcctcatttg      60
aggagtggga acaggcttcg gcgaacacaa agttgccgaa caagcaaccg gaaaagctta     120
ataggcaatg ggcagtcacc agcattgcct cgaccacact cacctctctc tgctcatgca     180
ggaaatagcc ctcaagatag tccaagaaat ttctccccca gtgcctcagc ccatttttca     240
tttgcacgga ggactgatgg acgccgctgg tcgttggctt ctctcccttc ctctggctat     300
gggacaaaca cacccagctc tacggtctct tcatcctgtt cctcccagga gaagttgcat     360
cagttaccat accaaccaac accagacgag ttacacttct tatcaaaaca tttctgtacc     420
accgaaagca tcgccactga gaacagatgc aggaacacgc cgatgcgccc ccgttcccga     480
agtctgagcc ctggacgttc tcccgcctgc tgtgaccatg aaataattat gatgaaccat     540
gtctacaaag aaaggttccc aaaggctaca gctcagatgg aagaacgtct aaaggaaatt     600
atcaccagct actctcctga caacgttcta cccttagcag atggagtgct tagtttcact     660
```

```
caccaccaga ttattgaact ggctcgagat tgcttggata aatcccacca gggcctcatc      720
acctcacgat acttccttga attacagcac aaattagata agttgctaca ggaggctcat      780
gatcgttcag aaagtggaga attggcattt attaaacaac tagttcgaaa gatcctaatt      840
gttattgccc gccctgctcg gttattagag tgcctgcgaat ttgatccgga agaattttac     900
tacctattgg aagcagcaga aggccatgcc aaagaaggac agggtattaa aaccgacatt      960
cccaggtaca tcattagcca actgggactc aataaggatc ccttggaaga aatggctcat     1020
ttgggaaact acgatagtgg gacagcagaa acaccagaaa cagatgaatc agtgagtagc     1080
tctaatgcct ccctgaaact tcgaaggaaa cctcgggaaa gtgattttga aacgattaaa     1140
ttgattagca atggagccta tggggcagtc tactttgttc ggcataaaga atcccggcag     1200
aggtttgcca tgaagaagat taataaacag aacctcatcc ttcgaaacca gatccagcag     1260
gcctttgtgg agcgggatat cctgactttt gcagaaaacc cctttgttgt cagcatgtat     1320
tgctcctttg aaacaaggcg ccacttgtgc atggtcatgg aatatgtgga aggggagac      1380 tgtgctactt taatgaaaaa catgggtcct ctccctgttg atatggccag aatgtacttt     1440
gctgagacgg tcttggcctt ggaatattta cataattatg gaattgtaca cagggatttg     1500
aaaccagaca acttgttggt tacctccatg ggcacataa agctgacaga ttttggatta      1560
tctaaggtgg gactaatgag catgactacc aaccttacg agggtcatat tgagaaggat      1620
gctagagagt tcctggataa acaggtctgt ggcacacctg aatacattgc accagaagtg     1680
attctgaggc agggttatgg aaagccggtg gactggtggg ccatggggat tatcctctat     1740
gaatttctgg ttggatgcgt gccattcttt ggggatactc cagaggagct atttggacaa     1800
gtcatcagtg atgagatcaa ctggcctgag aaggatgagg caccccccacc tgatgcccag    1860 gatctgatta ccttactcct caggcagaat cccctggaga ggctgggaac aggtggtgca     1920
tatgaagtca acagcatcg attcttccgt tctttagact ggaacagttt gctgagacag      1980
aaggcagaat ttattcccca actggaatct gaggatgaca caagttattt tgatactcgg     2040
tctgagaagt atcatcatat ggaaacggag gaagaagatg acacaaatga tgaagacttt    2100
aatgtggaaa taaggcagtt ttcttcatgt tcacacaggt tttcaaaagt tttcagcagt     2160
atagatcgaa tcactcagaa ttcagcagaa gagaaggaag actctgtgga caaaaccaaa    2220
agcaccacct tgccatccac agaaacactg agctggagtt cagaatattc tgaaatgcaa     2280
cagctatcaa catccaactc ttcagatact gaaagcaaca gacataaact cagttctggc     2340
ctacttccca aactggctat ttcaacagag ggagagcaag atgaagctgc tcctgccct     2400 ggagaccccc atgaggagcc aggaaagcca gcccttcctc ctgaagagtg tgcccaggag    2460
gagcctgagg tcaccacccc agccagcacc atcagcagct ccaccctgtc agatatgttt    2520
gctgtttccc ctctgggaag tccaatgtct ccccattccc tgtcctcgga cccttcttct     2580 tcacagagatt cctctcccag ccgagattcc tcagcagctt ctgccagtcc acatcagccg    2640
attgtgatcc acagttcggg gaagaactac ggctttacca tccgagccat ccgggtgtat     2700
gtgggagaca gtgacatcta tacagtgcac catatcgtct ggaatgtaga agaaggaagt     2760
ccggcatgcc aggcaggact gaaggctgga gatcttatca ctcacatcaa tggagaacca    2820
gtgcatggac ttgtccacac agaagttata gaactcctac tgaagagtgg gaataaggtg    2880
tcaatcacta ctacccccatt tgaaaacaca tcaatcaaaa ctggaccagc caggagaaac    2940
agctataaga gccggatggt gaggcggagc aagaaatcca gaagaaaga aagtctcgaa     3000 aggaggagat ctcttttcaa aaagctagcc aagcagcctt ctcctttact ccacaccagc    3060
```

```
cgaagtttct cctgcttgaa cagatccctg tcatcgggtg agagcctccc aggttccccc    3120
actcatagct tgtctccccg gtctccaaca ccaagctacc gctccacccc tgacttccca    3180
tctggtacta attcctccca gagcagctcc cctagttcta gtgccccaa ttccccagca    3240 gggtccgggc acatccggcc cagcactctc acggtcttg cacccaaact cggcgggcag    3300
cggtaccggt ccggaaggcg aaagtccgcc ggcaacatcc cactgtcccc gctggcccgg    3360
acgccctctc caaccccgca acccacctcc ccgcagcggt caccatcccc tcttctggga    3420
cactcactgg gcaattccaa gatcgcgcaa gcctttccca gcaagatgca ctccccgccc    3480
accatcgtca gacacatcgt gaggcccaag agtgcggagc cccccaggtc cccgctgctc    3540
aagcgcgtgc agtccgagga aagctgtcg ccctcttacg gcagtgacaa gaagcacctg    3600
tgctcccgca agcacagcct ggaggtgacc caagaggagg tgcagcggga gcagtcccag    3660
cgggaggcgc cgctgcagag cctggatgag aacgtgtgcg acgtgccgcc gctcagccgc    3720
gcccggccag tggagcaagg ctgcctgaaa cgcccagtct cccggaaggt gggccgccag    3780
gagtctgtgg acgacctgga ccgcgacaag ctgaaggcca aggtggtggt gaagaaagca    3840
gacggcttcc cagagaaaca ggaatcccac cagaaatccc atggacccgg gagtgatttg    3900
gaaaactttg ctctgtttaa gctggaagag agagagaaga agtctatcc gaaggctgtg    3960 gaaaggtcaa gtactttga aaacaaagcg tctatgcagg aggcgccacc gctgggcagc    4020
ctgctgaagg atgctcttca aagcaggcc agcgtgcgcg ccagcgaggg tgcgatgtcg    4080
gatggccggg tgcctgcgga gcaccgccag ggtggcgggg acttcagacg ggccccgct    4140 cctggcaccc tccaggatgg tctctgccac tccctcgaca ggggcatctc tgggaagggg    4200
gaaggcacgg agaagtcctc ccaggccaag gagcttctcc gatgtgaaaa gttagacagc    4260
aagctggcca acatcgatta cctccgaaag aaaatgtcac ttgaggacaa agaggacaac    4320
ctctgccctg tgctgaagcc caagatgaca gctggctccc acgaatgcct gccagggaac    4380
ccagtccgac ccacgggtgg gcagcaggag ccccgccgg cttctgagag ccgagctttt    4440
gtcagcagca cccatgcagc tcagatgagt gccgtctctt tgttcccct caaggcctta    4500 acaggccggg tggacagtgg aacggagaag cctggcttgg ttgctcctga gtcccctgtt    4560
aggaagagcc cctccgagta aagctggaa ggtaggtctg tctcatgcct gaagccgatc    4620
gagggcactc tggacattgc tctcctgtcc ggacctcagg cctccaagac agaactgcct    4680
tccccagagt ctgcacagag ccccagccca agtggtgacg tgagggcctc tgtgccacca    4740
gttctcccca gcagcagtgg gaaaaagaac gataccacca gtgcaagaga gctttctcct    4800
tccagcttaa agatgaataa atcctacctg ctggagcctt ggttcctgcc ccccagccga    4860
ggtctccaga attcaccagc agtttccctg cctgacccag agttcaagag ggacaggaaa    4920
ggtccccatc ctactgccag gagccctgga acagtcatgg aaagcaatcc caacagaga    4980 gagggcagct cccctaaaca ccaagaccac accactgacc ccaagcttct gacctgcctg    5040
gggcagaacc tccacagccc tgacctggcc aggccacgct gcccgctccc acctgaagct    5100
tccccctcaa gggagaagcc aggcctgagg gaatcgtctg aaagaggccc tcccacagcc    5160
agaagcgagc gctctgctgc gagggctgac acatgcagag agccctccat ggaactgtgc    5220
tttccagaaa ctgcgaaaac cagtgacaac tccaaaaatc tcctctctgt gggaaggacc    5280
cacccagatt tctatacaca gacccaggcc atgagaaag catgggcgcc gggtgggaaa    5340
acgaaccaca agatggccc aggtgaggcg aggcccccgc ccagagacaa ctcctctctg    5400
cactcagctg gaattccctg tgagaaggag ctgggcaagg tgaggcgtgg cgtggaaccc    5460
```

-continued

| | |
|---|---|
| aagcccgaag cgcttcttgc caggcggtct ctgcagccac ctggaattga gagtgagaag | 5520 |
| agtgaaaagc tctccagttt cccatctttg cagaaagatg gtgccaagga acctgaaagg | 5580 |
| aaggagcagc tctacaaag gcatcccagc agcatccctc cgcccctct gacggccaaa | 5640 |
| gacctgtcca gcccggctgc caggcagcat tgcagttccc caagccacgc ttctggcaga | 5700 |
| gagccggggg ccaagcccag cactgcagag cccagctcga gcccccagga ccctcccaag | 5760 |
| cctgttgctg cgcacagtga aagcagcagc cacaagcccc ggcctggccc tgacccgggc | 5820 |
| cctccaaaga ctaagcaccc cgaccggtcc ctctcctctc agaaaccaag tgtcggggcc | 5880 |
| acaaagggca aagagcctgc cactcagtcc ctcggtggct ctagcagaga ggggaagggc | 5940 |
| cacagtaaga gtgggccgga tgtgtttcct gctacccag gctcccagaa caaagccagc | 6000 |
| gatgggattg ccagggagaa aggtgggccc tctgtcccac tgcacactga cagggctcct | 6060 |
| ctagacgcca agccacaacc caccagtggt gggcggcccc tggaggtgct ggagaagcct | 6120 |
| gtgcatttgc caaggccggg cacccaggg cctagtgagc cagcggacca gaaactgtcc | 6180 |
| gctgttggtg aaaagcaaac cctgtctcca aagcacccca aaccatccac tgtgaaagat | 6240 |
| tgccccaccc tgtgcaaaca gacagacaac agacagacag acaaaagccc gagtcagccg | 6300 |
| gccgccaaca ccgacagaag ggcggaaggg aagaaatgca ctgaagcact ttatgctcca | 6360 |
| gcagagggcg acaagctcga ggccggcctt tcctttgtgc atagcgagaa ccggttgaaa | 6420 |
| ggcgcggagc ggccagccgc gggggtgggg aagggcttcc ctgaggccag agggaaggg | 6480 |
| cccggtcccc agaagccacc gacggaggca gacaagccca atggcatgaa cggtcccc | 6540 |
| tcagccactg ggcagagttc tttccgatcc acggcctcc cggaaaagtc tctgagctgc | 6600 |
| tcctccagct tccctgaaac cagggccgga gttagagagg cctctgcagc cagcagcgac | 6660 |
| acctcttctg ccaaggccgc cggggcatg ctggagcttc cagcccccag caacagggac | 6720 |
| cataggaagg ctcagcctgc cggggagggc cgaacccaca tgacaaagag tgactccctg | 6780 |
| ccctccttcc gggtctccac cctgcctctg gagtcacacc ccccgaccc aaacaccatg | 6840 |
| ggcggggcca gccaccggga cagggctctc tcggtgactg ccaccgtagg ggaaaccaaa | 6900 |
| gggaaggacc ctgccccagc ccagcctccc ccagctagga aacagaacgt gggcagagac | 6960 |
| gtgaccaagc catccccagc cccaaacact gaccgcccca tctctctttc taatgagaag | 7020 |
| gactttgtgg tacggcagag gcgggggaaa gagagtttgc gtagcagccc tcacaaaaag | 7080 |
| gccttgtaa | 7089 |

<210> SEQ ID NO 13
<211> LENGTH: 717
<212> TYPE: DNA
<213> ORGANISM: Homo sapiens

<400> SEQUENCE: 13

| | |
|---|---|
| atgggggaga aagtttcgga ggcgccagag ccggtgcccc gcggctgcag tggccacggc | 60 |
| agccggactc cagcctctgc gctggtcgcc gcgtcctctc cgggtgcttc ctcggccgag | 120 |
| tcctcctcgg gctcagaaac tctgtcggag aaggggagc ccggcggctt ctccagagag | 180 |
| catcagccgc cgccgccgcc gccgttggga ggcaccctgg gcgcccgggc gccgccgcg | 240 |
| tgggctccgg caagcgtgct gctggagcgc ggagtccttg cgctgccgcc gccgcttccc | 300 |
| ggaggagctg tgccgcccgc gccccggggc agcagcgcgt cccaggagga gcaggacgag | 360 |
| gagcttgacc acatattatc ccctccaccc atgccgtttc ggaaatgcag caacccagat | 420 |
| gtggcttctg gccctggaaa atcactgaag tataaaagac agctgagtga ggatggaaga | 480 |

| | |
|---|---|
| cagctaaggc gagggagcct gggaggagcc ctgactggga ggtaccttct tccaaacccg | 540 |
| gtggcgggac aggcctggcc ggcctctgca gagacgtcca acctcgtgcg catgcgcagc | 600 |
| caggccctgg gccagtcggc gccctcgctc accgccagcc tgaaggagct gagtctcccc | 660 |
| agaagaggaa gtttccctgt gtgtccaaat gctgggagaa catcacccct tggatga | 717 |

<210> SEQ ID NO 14
<211> LENGTH: 7290
<212> TYPE: DNA
<213> ORGANISM: Homo sapiens

<400> SEQUENCE: 14

| | |
|---|---|
| atggatatgt ctgaccccaa tttttggact gtgctctcaa actttacttt gcctcatttg | 60 |
| aggagtggga acaggcttcg gcgaacacaa agttgccgaa caagcaaccg gaaaagctta | 120 |
| ataggcaatg ggcagtcacc agcattgcct cgaccacact cacctctctc tgctcatgca | 180 |
| ggaaatagcc ctcaagatag tccaagaaat ttctccccca gtgcctcagc ccattttca | 240 |
| tttgcacgga ggactgatgg acgccgctgg tcgttggctt ctctcccttc ctctggctat | 300 |
| gggacaaaca cacccagctc tacggtctct tcatcctgtt cctcccagga gaagttgcat | 360 |
| cagttaccat accaaccaac accagacgag ttacacttct tatcaaaaca tttctgtacc | 420 |
| accgaaagca tcgccactga gaacagatgc aggaacacgc cgatgcgccc ccgttcccga | 480 |
| agtctgagcc ctggacgttc tcccgcctgc tgtgaccatg aaataattat gatgaaccat | 540 |
| gtctacaaag aaaggttccc aaaggctaca gctcagatgg aagaacgtct aaaggaaatt | 600 |
| atcaccagct actctcctga caacgttcta cccttagcag atggagtgct tagtttcact | 660 |
| caccaccaga ttattgaact ggctcgagat tgcttggata atcccaccag ggcctcatc | 720 |
| acctcacgat acttccttga attacagcac aaattagata agttgctaca ggaggctcat | 780 |
| gatcgttcag aaagtggaga attggcattt attaaacaac tagttcgaaa gatcctaatt | 840 |
| gttattgccc gccctgctcg gttattagag tgcctgaat ttgatccgga gaattttac | 900 |
| tacctattgg aagcagcaga aggccatgcc aaagaaggac agggtattaa aaccgacatt | 960 |
| cccaggtaca tcattagcca actgggactc aataaggatc ccttggaaga aatggctcat | 1020 |
| ttgggaaact acgatagtgg acagcagaaa acaccagaaa cagatgaatc agtgagtagc | 1080 |
| tctaatgcct ccctgaaact tcgaaggaaa cctcggaaa gtgattttga aacgattaaa | 1140 |
| ttgattagca atggagccta tgggcagtc tactttgttc ggcataaaga atcccggcag | 1200 |
| aggttttgcca tgaagaagat taataaacag aacctcatcc ttcgaaacca gatccagcag | 1260 |
| gccttttgtgg agcgggatat cctgactttt gcagaaaacc cctttgttgt cagcatgtat | 1320 |
| tgctcctttg aaacaaggcg ccacttgtgc atggtcatgg aatatgtgga agggggagac | 1380 |
| tgtgctactt taatgaaaaa catgggtcct ctccctgttg atatggccag aatgtacttt | 1440 |
| gctgagacgg tcttggcctt ggaatattta cataattatg aattgtaca cagggatttg | 1500 |
| aaaccagaca acttgttggt tacctccatg gggcacataa agctgacaga ttttggatta | 1560 |
| tctaaggtgg gactaatgag catgactacc aacctttacg aggtcatat tgagaaggat | 1620 |
| gctagagagt tcctggataa acaggtctgt ggcacacctg aatacattgc accagaagtg | 1680 |
| attctgaggc agggttatgg aaagccggtg gactggtggg ccatggggat tatcctctat | 1740 |
| gaatttctgg ttgatgcgt gccattcttt ggggatactc cagaggagct atttggacaa | 1800 |
| gtcatcagtg atgagatcaa ctggcctgag aaggatgagg cacccccacc tgatgcccag | 1860 |
| gatctgatta ccttactcct caggcagaat ccctggaga ggctgggaac aggtggtgca | 1920 |

-continued

```
tatgaagtca aacagcatcg attcttccgt tctttagact ggaacagttt gctgagacag    1980
aaggcagaat ttattcccca actggaatct gaggatgaca caagttattt tgatactcgg    2040
tctgagaagt atcatcatat ggaaacggag gaagaagatg acacaaatga tgaagacttt    2100
aatgtggaaa taaggcagtt ttcttcatgt tcacacaggt tttcaaaagt tttcagcagt    2160
atagatcgaa tcactcagaa ttcagcagaa gagaaggaag actctgtgga caaaaccaaa    2220
agcaccacct tgccatccac agaaacactg agctggagtt cagaatattc tgaaatgcaa    2280
cagctatcaa catccaactc ttcagatact gaaagcaaca gacataaact cagttctggc    2340
ctacttccca aactggctat ttcaacagag ggagagcaag atgaagctgc tcctgccct    2400 ggagacccccc atgaggagcc aggaaagcca gcccttcctc ctgaagagtg tgcccaggag    2460
gagcctgagg tcaccacccc agccagcacc atcagcagct ccaccctgtc agttggcagt    2520
ttttcagagc acttggatca gataaatgga cgaagcgagt gtgtggacag tacagataat    2580
tcctcaaagc catccagtga acccgcttct cacatggctc ggcagcgatt agaaagcaca    2640
gaaaaaaaga aaatctcggg gaaagtcaca aagtccctct ctgccagtgc tctttccctc    2700
atgatcccag gagatatgtt tgctgttcc cctctgggaa gtccaatgtc tccccattcc    2760
ctgtcctcgg acccttcttc ttcacgagat tcctctccca gccagagattc ctcagcagct    2820 tctgccagtc cacatcagcc gattgtgatc cacagttcgg ggaagaacta cggctttacc    2880
atccgagcca tccgggtgta tgtgggagac agtgacatct atacagtgca ccatatcgtc    2940
tggaatgtag aagaaggaag tccggcatgc caggcaggac tgaaggctgg agatcttatc    3000
actcacatca atggagaacc agtgcatgga cttgtccaca cagaagttat agaactccta    3060
ctgaagagtg ggaataaggt gtcaatcact actaccccat ttgaaaacac atcaatcaaa    3120
actggaccag ccaggagaaa cagctataag agccggatgg tgaggcggag caagaaatcc    3180
aagaagaaag aaagtctcga aggaggagga tctcttttca aaaagctagc caagcagcct    3240
tctcctttac tccacaccag ccgaagttc tcctgcttga acagatccct gtcatcgggt    3300
gagagcctcc caggttcccc cactcatagc ttgtctcccc ggtctccaac accaagctac    3360
cgctccaccc ctgacttccc atctggtact aattcctccc agagcagctc ccctagttct    3420
agtgccccca ttccccagc agggtccggg cacatccggc ccagcactct ccacggtctt    3480
gcacccaaac tcggcgggca gcggtaccgg tccggaaggc gaaagtccgc cggcaacatc    3540
ccactgtccc cgctggcccg gacgccctct ccaaccccgc aacccacctc cccgcagcgg    3600
tcaccatccc ctcttctggg acactcactg ggcaattcca agatcgcgca agccttccc    3660 agcaagatgc actccccgcc caccatcgtc agacacatcg tgaggcccaa gagtgcggag    3720
ccccccaggt ccccgctgct caagcgcgtg cagtccgagg agaagctgtc gccctcttac    3780
ggcagtgaca agaagcacct gtgctcccgc aagcacagcc tggaggtgac caagaggag    3840 gtgcagcggg agcagtccca gcgggaggcg ccgctgcaga gcctggatga aacgtgtgc    3900 gacgtgccgc cgctcagccg cgcccggcca gtggagcaag ctgcctgaa acgcccagtc    3960 tcccggaagg tgggccgcca ggagtctgtg gacgacctgg accgcgacaa gctgaaggcc    4020
aaggtggtgg tgaagaaagc agacggcttc cagagaaac aggaatccca ccagaaatcc    4080
catggacccg ggagtgattt ggaaaacttt gctctgttta gctggaaga gagagagaag    4140 aaagtctatc cgaaggctgt ggaaaggtca agtactttg aaaacaaagc gtctatgcag    4200
gaggcgccac cgctgggcag cctgctgaag gatgctcttc acaagcaggc cagcgtgcgc    4260
gccagcgagg gtgcgatgtc ggatggccgg gtgcctgcgg agcaccgcca gggtggcggg    4320
```

```
gacttcagac gggcccccgc tcctggcacc ctccaggatg gtctctgcca ctccctcgac    4380
aggggcatct ctgggaaggg ggaaggcacg gagaagtcct cccaggccaa ggagcttctc    4440
cgatgtgaaa agttagacag caagctggcc aacatcgatt acctccgaaa gaaaatgtca    4500
cttgaggaca aagaggacaa cctctgccct gtgctgaagc ccaagatgac agctggctcc    4560
cacgaatgcc tgccagggaa cccagtccga cccacgggtg ggcagcagga gccccgccg     4620
gcttctgaga ccgagctttt tgtcagcagc acccatgcag ctcagatgag tgccgtctct    4680
tttgttcccc tcaaggcctt aacaggccgg gtggacagtg gaacggagaa gcctggcttg    4740
gttgctcctg agtcccctgt taggaagagc ccctccgagt ataagctgga aggtaggtct    4800
gtctcatgcc tgaagccgat cgagggcact ctggacattg ctctcctgtc cggacctcag    4860
gcctccaaga cagaactgcc ttccccagag tctgcacaga gccccagccc aagtggtgac    4920
gtgagggcct ctgtgccacc agttctcccc agcagcagtg ggaaaaagaa cgataccacc    4980
agtgcaagag agctttctcc ttccagctta aagatgaata aatcctacct gctggagcct    5040
tggttcctgc cccccagccg aggtctccag aattcaccag cagtttccct gcctgaccca    5100
gagttcaaga gggacaggaa aggtccccat cctactgcca ggagccctgg aacagtcatg    5160
gaaagcaatc cccaacagag agagggcagc tcccctaaac accaagacca caccactgac    5220
cccaagcttc tgacctgcct ggggcagaac ctccacagcc ctgacctggc caggccacgc    5280
tgcccgctcc cacctgaagc ttccccctca agggagaagc caggcctgag ggaatcgtct    5340
gaaagaggcc ctcccacagc cagaagcgag cgctctgctg cgagggctga cacatgcaga    5400
gagccctcca tggaactgtg cttttccgaa actgcgaaaa ccagtgacaa ctccaaaaat    5460
ctcctctctg tgggaaggac ccacccagat ttctatacac agacccaggc catggagaaa    5520
gcatgggcgc cgggtgggaa aacgaaccac aaagatggcc caggtgaggc gaggcccccg    5580
cccagagaca actcctctct gcactcagct ggaattccct gtgagaagga gctgggcaag    5640
gtgaggcgtg gcgtggaacc caagcccgaa gcgcttcttg ccaggcggtc tctgcagcca    5700
cctggaattg agagtgagaa gagtgaaaag ctctccagtt tcccatcttt gcagaaagat    5760
ggtgccaagg aacctgaaag gaaggagcag cctctacaaa ggcatcccag cagcatccct    5820
ccgccccctc tgacggccaa agacctgtcc agccggctg ccaggcagca ttgcagttcc     5880
ccaagccacg cttctggcag agagccgggg gccaagccca gcactgcaga gcccagctcg    5940
agcccccagg accctcccaa gcctgttgct gcgcacagtg aaagcagcag ccacaagccc    6000
cggcctggcc ctgacccggg ccctccaaag actaagcacc ccgaccggtc cctctcctct    6060
cagaaaccaa gtgtcggggc cacaaagggc aaagagcctg ccactcagtc cctcggtggc    6120
tctagcagag aggggaaggg ccacagtaag agtgggccgg atgtgtttcc tgctacccca    6180
ggctcccaga acaaagccag cgatgggatt ggccaggag aaggtgggcc ctctgtccca     6240
ctgcacactg acagggctcc tctagacgcc aagccacaac ccaccagtgg tgggcggccc    6300
ctggaggtgc tggagaagcc tgtgcatttg ccaaggccgg acacccagg gcctagtgag     6360
ccagcggacc agaaactgtc cgctgttggt gaaaagcaaa ccctgtctcc aaagcacccc    6420
aaaccatcca ctgtgaaaga ttgccccacc ctgtgcaaac agacagacaa cagacagaca    6480
gacaaaagcc cgagtcagcc ggccgccaac accgacagaa gggcggaagg gaagaaatgc    6540
actgaagcac tttatgctcc agcagagggc gacaagctcg aggccggcct ttcctttgtg    6600
catagcgaga accggttgaa aggcgcggag cggccagccg cggggtggg gaagggcttc     6660
cctgaggcca gagggaaagg gcccggtccc cagaagccac cgacggaggc agacaagccc    6720
```

-continued

```
aatggcatga aacggtcccc ctcagccact gggcagagtt ctttccgatc cacggccctc      6780
ccggaaaagt ctctgagctg ctcctccagc ttccctgaaa ccagggccgg agttagagag      6840
gcctctgcag ccagcagcga cacctcttct gccaaggccg ccgggggcat gctggagctt      6900
ccagccccca gcaacaggga ccataggaag gctcagcctg ccggggaggg ccgaacccac      6960
atgacaaaga gtgactccct gccctccttc cgggtctcca ccctgcctct ggagtcacac      7020 cacccccgacc caaacaccat gggcgggggcc agccaccggg acagggctct ctcggtgact    7080
gccaccgtag gggaaaccaa agggaaggac cctgccccag cccagcctcc cccagctagg      7140
aaacagaacg tgggcagaga cgtgaccaag ccatccccag ccccaaacac tgaccgcccc      7200
atctctcttt ctaatgagaa ggactttgtg gtacggcaga ggcgggggaa agagagtttg      7260
cgtagcagcc ctcacaaaaa ggccttgtaa                                       7290
```

<210> SEQ ID NO 15
<211> LENGTH: 2618
<212> TYPE: PRT
<213> ORGANISM: Mus musculus

<400> SEQUENCE: 15

```
Met Gly Glu Lys Val Ser Glu Ala Pro Glu Pro Val Pro Arg Gly Cys
1               5                   10                  15

Ser Gly His Gly Ala Arg Thr Leu Val Ser Ala Ala Val Ser
            20                  25                  30

Ser Glu Gly Ala Ser Ser Ala Glu Ser Ser Ser Gly Ser Glu Thr Leu
        35                  40                  45

Ser Glu Glu Gly Glu Pro Ser Arg Phe Ser Cys Arg Ser Gln Pro Pro
    50                  55                  60

Arg Pro Pro Gly Gly Ala Leu Gly Thr Arg Leu Pro Ala Ala Trp Ala
65                  70                  75                  80

Pro Ala Arg Val Ala Leu Glu Arg Gly Val Pro Thr Leu Pro Leu Pro
                85                  90                  95

His Pro Gly Gly Ala Val Leu Pro Val Pro Gln Val Ser Ser Ala Ser
            100                 105                 110

Gln Glu Glu Gln Asp Glu Glu Leu Asp His Ile Leu Ser Pro Pro
        115                 120                 125

Met Pro Phe Arg Lys Cys Ser Asn Pro Asp Val Ala Cys Gly Leu Gly
    130                 135                 140

Lys Ser Leu Lys Tyr Lys Arg Gln Leu Ser Glu Asp Gly Lys Gln Leu
145                 150                 155                 160

Arg Arg Gly Ser Leu Gly Gly Ala Leu Thr Gly Arg Tyr Leu Leu Pro
                165                 170                 175

Asn Pro Val Ala Gly Gln Ala Trp Pro Ala Ser Ala Glu Thr Ser Asn
            180                 185                 190

Leu Val Arg Met Arg Ser Gln Ala Leu Gly Gln Ser Ala Pro Ser Leu
        195                 200                 205

Thr Ala Ser Leu Lys Glu Leu Ser Leu Pro Arg Arg Gly Ser Leu Cys
    210                 215                 220

Arg Thr Ser Asn Arg Lys Ser Leu Ile Gly Asn Gly Gln Ser Pro Ala
225                 230                 235                 240

Leu Pro Arg Pro His Ser Pro Leu Ser Ala His Ala Gly Asn Ser Pro
                245                 250                 255

Gln Asp Ser Pro Arg Asn Phe Ser Pro Ser Ala Ser Ala His Phe Ser
            260                 265                 270
```

```
Phe Ala Arg Arg Thr Asp Gly Arg Arg Trp Ser Leu Ala Ser Leu Pro
            275                 280                 285
Ser Ser Gly Tyr Gly Thr Asn Thr Pro Ser Ser Thr Val Ser Ser Ser
        290                 295                 300
Cys Ser Ser Gln Glu Lys Leu His Gln Leu Pro Tyr Gln Pro Thr Pro
305                 310                 315                 320
Asp Glu Leu His Phe Leu Ser Lys His Phe Cys Thr Thr Glu Ser Ile
                325                 330                 335
Ala Thr Glu Asn Arg Cys Arg Asn Thr Pro Met Arg Pro Arg Ser Arg
            340                 345                 350
Ser Leu Ser Pro Gly Arg Ser Pro Ala Cys Cys Asp His Glu Ile Ile
        355                 360                 365
Met Met Asn His Val Tyr Lys Glu Arg Phe Pro Lys Ala Thr Ala Gln
370                 375                 380
Met Glu Glu Arg Leu Lys Glu Ile Ile Thr Ser Tyr Ser Pro Asp His
385                 390                 395                 400
Val Leu Pro Leu Ala Asp Gly Val Leu Ser Phe Thr His Gln Ile
                405                 410                 415
Ile Glu Leu Ala Arg Asp Cys Leu Asp Lys Ser His Gln Gly Leu Ile
            420                 425                 430
Thr Ser Arg Tyr Phe Glu Leu Gln His Lys Leu Asp Lys Leu Leu
        435                 440                 445
Gln Glu Ala His Asp Arg Ser Glu Ser Gly Leu Ala Phe Ile Lys
    450                 455                 460
Gln Leu Val Arg Lys Ile Leu Ile Val Ile Ala Arg Pro Ala Arg Leu
465                 470                 475                 480
Leu Glu Cys Leu Glu Phe Asp Pro Glu Glu Phe Tyr Tyr Leu Leu Glu
                485                 490                 495
Ala Ala Glu Gly His Ala Lys Glu Gly Gln Gly Ile Lys Thr Asp Ile
            500                 505                 510
Pro Arg Tyr Ile Ile Ser Gln Leu Gly Leu Asn Lys Asp Pro Leu Glu
        515                 520                 525
Glu Met Ala Gln Leu Gly Asn Tyr Asp Ser Arg Thr Ala Glu Thr Pro
    530                 535                 540
Glu Met Asp Glu Ser Val Ser Ser Ser Asn Thr Ser Leu Arg Leu Arg
545                 550                 555                 560
Arg Lys Pro Arg Glu Ser Asp Phe Glu Thr Ile Lys Leu Ile Ser Asn
                565                 570                 575
Gly Ala Tyr Gly Ala Val Tyr Phe Val Arg His Lys Glu Ser Arg Gln
            580                 585                 590
Arg Phe Ala Met Lys Lys Ile Asn Lys Gln Asn Leu Ile Leu Arg Asn
        595                 600                 605
Gln Ile Gln Gln Ala Phe Val Glu Arg Asp Ile Leu Thr Phe Ala Glu
    610                 615                 620
Asn Pro Phe Val Val Ser Met Tyr Cys Ser Phe Glu Thr Arg Arg His
625                 630                 635                 640
Leu Cys Met Val Met Glu Tyr Val Glu Gly Gly Asp Cys Ala Thr Leu
                645                 650                 655
Met Lys Asn Met Gly Pro Leu Pro Val Asp Met Ala Arg Met Tyr Phe
            660                 665                 670
Ala Glu Thr Val Leu Ala Leu Glu Tyr Leu His Asn Tyr Gly Ile Val
        675                 680                 685
```

```
His Arg Asp Leu Lys Pro Asp Asn Leu Leu Val Thr Ser Met Gly His
    690             695                 700
Ile Lys Leu Thr Asp Phe Gly Leu Ser Lys Val Gly Leu Met Ser Met
705             710                 715                 720
Thr Thr Asn Leu Tyr Glu Gly His Ile Glu Lys Asp Ala Arg Glu Phe
                725                 730                 735
Leu Asp Lys Gln Val Cys Gly Thr Pro Glu Tyr Ile Ala Pro Glu Val
            740                 745                 750
Ile Leu Arg Gln Gly Tyr Gly Lys Pro Val Asp Trp Trp Ala Met Gly
            755                 760                 765
Ile Ile Leu Tyr Glu Phe Leu Val Gly Cys Val Pro Phe Phe Gly Asp
770             775                 780
Thr Pro Glu Glu Leu Phe Gly Gln Val Ile Ser Asp Glu Ile Asn Trp
785             790                 795                 800
Pro Glu Lys Asp Glu Ala Pro Pro Asp Ala Gln Glu Leu Ile Thr
                805                 810                 815
Leu Leu Leu Arg Gln Asn Pro Leu Glu Arg Leu Gly Thr Gly Gly Ala
            820                 825                 830
Tyr Glu Val Lys Gln His Arg Phe Phe Arg Ser Leu Asp Trp Asn Ser
            835                 840                 845
Leu Leu Arg Gln Lys Ala Glu Phe Ile Pro Gln Leu Glu Ser Glu Asp
850             855                 860
Asp Thr Ser Tyr Phe Asp Thr Arg Ser Glu Lys Tyr His His Met Glu
865             870                 875                 880
Thr Glu Glu Glu Asp Asp Thr Asn Asp Glu Asp Phe Thr Val Glu Ile
                885                 890                 895
Arg Gln Phe Ser Ser Cys Ser His Arg Phe Ser Lys Val Phe Ser Ser
                900                 905                 910
Ile Asp Arg Ile Thr Gln Asn Ser Gly Glu Asp Lys Asp Ser Glu
            915                 920                 925
Asp Lys Thr Lys Ser Thr Thr Leu Pro Ser Thr Glu Thr Leu Ser Trp
930             935                 940
Ser Ser Glu Tyr Ser Glu Met Gln Gln Leu Ser Thr Ser Asn Ser Ser
945             950                 955                 960
Asp Thr Glu Ser Asn Arg Cys Lys Leu Ser Ser Gly Leu Leu Pro Lys
                965                 970                 975
Leu Ala Ile Ser Thr Asp Gly Glu Gln Asp Glu Ala Val Pro Cys Ser
            980                 985                 990
Gly Asp Pro Arg Glu Glu Pro Glu Lys Pro Val Pro Pro Ser Glu Glu
            995                 1000                1005
Cys Thr Gln Glu Glu Pro Glu Val Thr Thr Pro Ala Ser Thr Ile Ser
    1010            1015                1020
Ser Ser Thr Leu Ser Val Gly Ser Phe Ser Glu His Leu Asp Gln Ile
    1025            1030                1035                1040
Asn Gly Arg Ser Glu Cys Val Asp Ser Thr Asp Asn Ser Ser Lys Pro
                1045                1050                1055
Ser Ser Glu Pro Thr Ser His Val Ala Arg Gln Arg Leu Glu Ser Thr
            1060                1065                1070
Glu Lys Lys Lys Ile Ser Gly Lys Val Thr Lys Ser Leu Ser Ala Ser
    1075            1080                1085
Ala Leu Ser Leu Met Ile Pro Gly Asp Met Phe Ala Val Ser Pro Leu
    1090            1095                1100
```

```
Gly Ser Pro Met Ser Pro His Ser Leu Ser Ser Asp Pro Ser Ser Ser
1105                1110                1115                1120

Arg Asp Ser Ser Pro Ser Arg Asp Ser Ser Ala Ala Ser Ala Ser Pro
            1125                1130                1135

His Gln Pro Ile Val Ile His Ser Ser Gly Lys Asn Tyr Gly Phe Thr
        1140                1145                1150

Ile Arg Ala Ile Arg Val Tyr Val Gly Asp Ser Asp Ile Tyr Thr Val
    1155                1160                1165

His His Ile Val Trp Asn Val Glu Glu Gly Ser Pro Ala Tyr Gln Ala
1170                1175                1180

Gly Leu Lys Ala Gly Asp Leu Ile Thr His Ile Asn Gly Glu Pro Val
1185                1190                1195                1200

His Gly Leu Val His Thr Glu Val Ile Glu Leu Leu Leu Lys Ser Gly
            1205                1210                1215

Asn Lys Val Ser Ile Thr Thr Thr Pro Phe Glu Asn Thr Ser Ile Lys
        1220                1225                1230

Thr Gly Pro Ala Arg Arg Asn Ser Tyr Lys Gly Arg Met Val Arg Arg
    1235                1240                1245

Ser Lys Lys Ser Lys Lys Lys Glu Ser Leu Glu Arg Arg Arg Ser Leu
1250                1255                1260

Phe Lys Lys Leu Ala Lys Gln Pro Ser Pro Leu Leu His Thr Ser Arg
1265                1270                1275                1280

Ser Phe Ser Cys Leu Asn Arg Ser Leu Ser Ser Gly Glu Ser Leu Pro
            1285                1290                1295

Gly Ser Pro Thr His Ser Leu Ser Pro Arg Ser Pro Thr Pro Ser Tyr
        1300                1305                1310

Arg Ser Thr Pro Asp Phe Pro Ser Gly Thr Asn Ser Ser Gln Ser Ser
    1315                1320                1325

Ser Pro Ser Ser Ser Ala Pro Asn Ser Pro Ala Gly Ser Gly His Ile
1330                1335                1340

Arg Pro Ser Thr Leu His Gly Leu Ala Pro Lys Leu Ser Gly Gln Arg
1345                1350                1355                1360

Tyr Arg Ser Gly Arg Arg Lys Ser Ala Gly Ser Ile Pro Leu Ser Pro
            1365                1370                1375

Leu Ala Arg Thr Pro Ser Pro Thr Pro Gln Pro Thr Ser Pro Gln Arg
        1380                1385                1390

Ser Pro Ser Pro Leu Leu Gly His Ser Leu Gly Asn Ala Lys Ile Thr
    1395                1400                1405

Gln Ala Phe Pro Ser Lys Met His Ser Pro Pro Thr Ile Val Arg His
1410                1415                1420

Ile Val Arg Pro Lys Ser Ala Glu Pro Pro Arg Ser Pro Leu Leu Lys
1425                1430                1435                1440

Arg Val Gln Ser Glu Glu Lys Leu Ser Pro Ser Tyr Gly Ser Asp Lys
            1445                1450                1455

Lys Leu Leu Cys Ser Arg Lys His Ser Leu Glu Val Thr Gln Glu Glu
        1460                1465                1470

Val Gln Arg Glu Gln Cys Gln Arg Glu Val Thr Leu Gln Ser Leu Glu
    1475                1480                1485

Glu Asn Val Cys Asp Ala Pro Ser Leu Ser Arg Ala Arg Pro Val Glu
1490                1495                1500

Gln Gly Cys Leu Lys Arg Pro Val Ser Arg Lys Val Gly Arg Gln Glu
1505                1510                1515                1520
```

-continued

Ser Val Asp Asp Leu Asp Arg Asp Lys Leu Lys Ala Lys Val Val Val
1525                1530                1535

Lys Lys Pro Glu Glu Lys His Glu Ser His Gln Lys Pro His Ser Leu
        1540                1545                1550

Gly Gly Asp Ser Glu Ser Tyr Ala Leu Phe Arg Leu Glu Glu Arg Glu
        1555                1560                1565

Lys Lys Val Tyr Ser Lys Gly Leu Glu Arg Ser Gly His Phe Glu Asn
    1570                1575                1580

Thr Ser Ala Glu Leu Pro Ser Val Gly Ser Leu Leu Lys Asp Thr Leu
1585                1590                1595                1600

His Lys Gln Ala Ser Val Arg Ala Ser Glu Gly Val Thr Ser Asp Gly
            1605                1610                1615

Ala Ala Cys Ser Leu Thr Pro Gly Glu His Ser Gln Ser Leu Gly Asp
            1620                1625                1630

Phe Lys Arg Ala Ser Ala Ser Gly Ile Leu His Asp Ser Val Cys Pro
        1635                1640                1645

Ile Ser Asp Arg Pro Ala Pro Gly Lys Val Glu Tyr Ser Glu Lys Ala
    1650                1655                1660

Ser Gln Ala Lys Glu Leu Leu Arg Ser Glu Lys Leu Asp Ser Lys Leu
1665                1670                1675                1680

Ala Asn Ile Asp Tyr Leu Arg Lys Lys Met Ser Leu Asp Asp Lys Asp
            1685                1690                1695

Asp Ser His Cys Ala Ile Leu Lys Pro Lys Ile Thr Ser Ser Ala His
            1700                1705                1710

Glu Cys Leu Pro Gly Asn Pro Ile Arg Pro Met Ala Gly Gln Gln Glu
        1715                1720                1725

Thr Pro Pro Ala Ser Glu Asn Arg Ala Phe Ile Asn Ser Thr His Thr
    1730                1735                1740

Pro Gln Met Ser Ala Val Ser Phe Val Pro Leu Lys Ala Leu Ala Gly
1745                1750                1755                1760

Arg Val Glu Asn Gly Gly Glu Lys Ala Gly Leu Ala Ala Pro Glu Ser
            1765                1770                1775

Pro Val Arg Lys Ser Pro Ser Glu Tyr Lys Leu Glu Gly Arg Ser Val
            1780                1785                1790

Ser Cys Leu Lys Pro Ile Glu Gly Thr Leu Asp Ile Ala Leu Leu Ser
        1795                1800                1805

Gly Pro His Ala Ser Lys Thr Glu Leu Leu Ser Pro Glu Pro Ala Gln
    1810                1815                1820

Ser Pro Ser Pro Gly Ile Asn Val Gly Pro Cys Val Pro Leu Ala Leu
1825                1830                1835                1840

Pro Gly Ser Ser Gly Lys Lys Gly Asp Ser Thr Ser Leu Arg Glu Pro
            1845                1850                1855

Ser Ser Ala Asn Leu Lys Val Asn Lys Ser Tyr Leu Leu Glu Pro Arg
            1860                1865                1870

Phe Leu Pro Pro Ser Arg Ala Leu Gln Asp Ser Leu Ala Ala Ser Gly
        1875                1880                1885

Pro Glu Pro Lys Ser Lys Pro Glu Arg Lys Leu Ile His Pro Ser Ala
    1890                1895                1900

Arg Ser Pro Ala Thr Val Thr Glu Ser Asn Leu Gln Gln Lys Glu Gly
1905                1910                1915                1920

Gly Pro Ala Thr His Gln Asp Arg Ser Thr Asp Thr Arg Asn Leu Pro
            1925                1930                1935

-continued

Gly Pro Gly Gln Thr Leu His Asn Val Asp Leu Pro Arg Leu Cys Thr
        1940                1945                1950

Arg Ala Pro Leu Pro Pro Glu Gly Thr Pro Ala Lys Glu Lys Pro Cys
    1955                1960                1965

Leu Lys Glu Pro Ser Ala Lys Val Lys Ser Glu Trp Ser Ala Val Arg
    1970                1975                1980

Asp Asp Gly His Arg Asp Pro Cys Ala Lys Leu Cys Pro Ala Glu Thr
1985                1990                1995                2000

Gly Lys Ala Ser Asp Ser Ser Lys Pro Leu Pro Ser Gly Gly Arg Thr
            2005                2010                2015

Gln Pro Asp Phe Tyr Lys Gln Thr Gln Thr Ser Glu Lys Ala Trp Ala
        2020                2025                2030

His Ala Lys Thr Asn His Lys Asp Ser Gln Asp Glu Val Lys Ser Leu
    2035                2040                2045

Ala Arg Glu Asp Ser Ala Ser Leu Leu Tyr Glu Lys Glu Ile Gly Arg
    2050                2055                2060

Ala Arg Lys Gly Pro Glu Pro Lys Pro Glu Val Pro Ala Thr Arg Cys
2065                2070                2075                2080

Pro Pro Gln Pro Pro Gly Ile Glu Gly Glu Lys Arg Glu Lys Leu Ser
            2085                2090                2095

Ala Ala Pro Ser Leu Gln Lys Gln Ala Pro Lys Glu Pro Asp Arg Lys
        2100                2105                2110

Glu Gln Thr Ser Gln Arg Pro Gly Gly Ser Gly Pro Gln Gln Pro Pro
        2115                2120                2125

Pro Thr Lys Glu Leu Ser Asn Ser Ala Ser Trp Gln His Gly Ser Ser
    2130                2135                2140

Pro Ser His Thr Leu Lys Lys Glu Pro Gly Thr Lys Ala Ala Ala Ala
2145                2150                2155                2160

Glu Pro Ser Thr Ser Leu His Asp Thr Pro Arg Ser Ala Thr Ala Thr
            2165                2170                2175

Thr Thr Ala Ile Ala Thr Thr Thr Thr Thr Thr Ser Ala Gly His Ser
        2180                2185                2190

Asp Cys Ser Ser His Lys Ala Arg Pro Gly Pro Asp Pro Ser Pro Ser
        2195                2200                2205

Lys Ser Lys His Gln Asp Arg Ser Leu Ser Ser Gln Lys Leu Ser Ala
    2210                2215                2220

Gly Ser Ala Lys Gly Lys Glu Pro Val Thr Gln Pro Leu Gly Gly Ser
2225                2230                2235                2240

Ile Arg Glu Gly Lys Gly Gly Ser Lys Gly Pro Val Asp Thr Phe Ser
            2245                2250                2255

Ala Val Leu Thr Thr Gln Gly Lys Ala Ser Asp Val Leu Val Gln Gly
        2260                2265                2270

Glu Gly Arg Val Ser Ile Ile Val His Thr Glu Glu Cys Pro Leu Asp
    2275                2280                2285

Ala Lys Leu Lys Asn Thr Asn Gly Gly Cys Pro Pro Glu Met Gln Ala
    2290                2295                2300

Lys His Pro Pro Arg Gln Gly His Leu Ser Glu Ala Ala Asp Gln Lys
2305                2310                2315                2320

Pro Leu Ile Ala Gly Glu Lys Gln Ser Pro Ser Pro Lys His Pro Lys
            2325                2330                2335

Pro Ser Thr Val Lys Asp Tyr Pro Ser Leu Cys Arg Gln Thr Asp Arg
        2340                2345                2350

```
Ser Pro Ser His Gln Ala Thr Thr Gly Asp Arg Lys Ala Glu Gly Lys
        2355                2360                2365

Lys Cys Thr Asp Ala Leu Tyr Val Ala Ala Pro Glu Gly Tyr Lys Pro
    2370                2375                2380

Glu Ala Ser Pro Ser Leu His His Gly Glu Thr Gly Leu Arg Gly Ser
2385                2390                2395                2400

Glu Arg Pro Pro Met Gly Met Gly Lys Gly Phe Ser Glu Pro Lys Gly
            2405                2410                2415

Lys Gly Pro Gly Pro Gln Lys Ser Leu Ala Glu Thr Gly Lys Pro Ser
                2420                2425                2430

Gly Met Lys Arg Ser Pro Ser Ala Thr Val Gln Ser Ser Leu Arg Ser
        2435                2440                2445

Ala Ala Pro Pro Glu Lys Ser Leu Ser Tyr Ser Ala Ser Phe Pro Glu
    2450                2455                2460

Ala Gln Pro Gly Val Arg Glu Val Pro Ala Ala Asn Ser Ser Pro Ser
2465                2470                2475                2480

Ser Ala Lys Ala Thr Gly Gly Thr Ser Glu Phe Pro Ala Pro Ser Ser
            2485                2490                2495

Arg Asp His Arg Lys Leu Gln Ser Gly Gly Asp Gly Arg Ser Gln Met
                2500                2505                2510

Ile Lys Ser Asp Ser Leu Pro Ser Phe Arg Leu Ser Thr Ser Ala Leu
        2515                2520                2525

Glu Ser His Phe Gln Asp Pro Gln Val Pro Ile Ala Ser Gly His Arg
    2530                2535                2540

Gly Arg Ala Leu Ser Val Thr Ala Ala Thr Gly Glu Pro Lys Gly Arg
2545                2550                2555                2560

Glu Leu Ala Gln Pro Pro Val Arg Lys Gln Asn Ala Cys Arg Glu
            2565                2570                2575

Ala Thr Arg Ala Pro Pro Ala Pro Ser Thr Asp Arg Ser Leu Pro Leu
                2580                2585                2590

Ser Ser Glu Lys Asp Phe Val Val Arg Gln Arg Gly Lys Glu Thr
        2595                2600                2605

Leu Arg Ser Ser Pro His Lys Lys Ala Ser
    2610                2615

<210> SEQ ID NO 16
<211> LENGTH: 7857
<212> TYPE: DNA
<213> ORGANISM: Mus musculus

<400> SEQUENCE: 16
atgggggaga aagtttccga ggcgcctgag cccgtgcccc ggggctgcag cggacacggc      60
gcccggaccc tagtctcttc ggcggcagcc gtgtcctcgg agggcgcttc ctcagcggag     120
tcatcctctg gctcggaaac tctgtcggag aaggggagc ccagccgctt ctcctgcagg      180
tcgcagccgc cgcggccgcc gggcggcgcc ctggaaccc ggctacccgc cgcgtgggct      240
cccgcgcgcg tggctctgga gcgtggagtc cctaccctgc cgctgccgca cccgggagga     300
gcggtgctgc cggtgcccca ggtcagcagc gcatcccaag aggagcagga tgaagagctt     360
gaccacatac tgtctccgcc acccatgccg tttcggaaat gcagcaaccc agatgtggcc     420
tgcggcctcg gaaaatcact gaagtacaag agacagctta gtgaggatgg gaagcagctg     480
cggcggggga gctgggagg agccctcaca gggaggtacc tccttccaaa cccggtagca     540
ggacaggcct ggcctgcttc ggcggagacg tccaacctcg tgcgcatgcg cagccaggcc     600
```

```
cttggccaat cggctccctc gctcacagcc agcttgaagg agctgagcct cccccgaaga    660
ggaagtcttt gccgaacaag caaccggaag agtttgatag gcaatggcca gtctccagca    720
ctgcctcgac cacactcacc tctctctgct catgcaggaa atagccctca agacagtcca    780
aggaatttct cccccagtgc ctcagcccat ttctcatttg cgaggagaac ggatgggcgc    840
cgctggtctc tggcttctct cccttcctca ggctatggga caaataccccc aagctccacc    900 gtctcctcat cctgttcttc caggagaag ttgcaccagc taccatacca gccaacccca    960
gatgaattac acttcttatc aaacacttc tgcacaacag aaagtatcgc cactgagaac   1020
cggtgcagaa acacacccat gcgtccacgt tcccggagtc tcagccctgg acggtccccc   1080
gcctgctgtg accatgaaat aattatgatg aaccatgtct acaaagaaag gttcccaaag   1140
gccacagctc agatggaaga gcgtctgaag gagatcatca ccagctactc tccagaccat   1200
gttctcccct tggcagatgg ggtacttagt ttcactcacc atcagatcat tgagctggct   1260
cgggactgtt tggataaatc tcaccagggt ctcatcacgt cgagatactt ttttgagttg   1320
cagcacaaac tggacaagtt gctccaggag gctcacgatc gctctgaaag tggagaactg   1380
gcatttatca agcaactagt ccgaaagatc ctaattgtca ttgcccgccc cgctcggtta   1440
ttggagtgtt tggaatttga tcctgaagaa ttttattacc tattggaagc tgcagaaggc   1500
catgccaaag aaggccaagg aatcaaaact gacatcccta ggtatatcat cagccagctg   1560
ggactcaata aggacccttt agaagaaatg gctcagttgg ggaattacga cagtaggaca   1620
gcagagacac cagagatgga tgagtcagtg agtagctcaa atacttccct gagacttcga   1680
aggaaacccc gagagagtga ttttgaaaca attaaattga tcagcaatgg agcctacggg   1740
gcagtctact ttgttcggca caagagtcc cgccagaggt ttgccatgaa gaagatcaac   1800
aagcagaacc tcatccttcg gaaccagatc cagcaggcct cgtggagcg agacatcctg   1860 actttcgcag agaacccctt tgtggtcagc atgtattgct cctttgaaac gaggcgtcac   1920
ttatgcatgg tcatggagta tgtagaaggg ggagactgtg cgaccctaat gaaaaacatg   1980
ggacctctcc cagttgatat ggccagaatg tatttcgccg agaccgtctt ggccttggag   2040
tacctgcata attaccggaat cgtacacagg gacttgaagc cagacaacct gttggtcacc   2100
tccatggggc acataaaact gactgacttc ggcttgtcta aggtgggatt aatgagcatg   2160
accaccaatc tctatgaagg ccacatagag aaggacgctc gagagttctt agataaacag   2220
gtctgtggta cacctgagta cattgccccc gaggtgattc tgagacaggg ctacgggaaa   2280
cccgtggact ggtgggccat gggcattatc ctctatgaat ttctggtcgg atgtgtgcct   2340
ttctttgggg acactccaga agagctattt ggacaagtca tcagtgatga aatcaactgg   2400
cctgaaaagg acgaggcccc tcctccagac gctcaggagc tgattacctt gctcctcagg   2460
cagaatccgc tggagaggct gggaacaggt ggagcctatg aagtgaagca gcatcgtttc   2520
ttccgctcct tagactggaa cagtttgctg agacagaagg cggaatttat tccccaactg   2580
gaatcggagg atgacacaag ttattttgat actcggtcag agaagtatca tcacatggag   2640
acggaggagg aggacgatac aaacgatgag gacttcaccg tggagataag gcagtttctct   2700 tcctgttcac acaggttttc aaaagttttc agcagtatag atcgcataac tcaaaattca   2760
ggagaagaca aagatgactc tgaggacaag accaaaagca caacgttgcc atccacagag   2820
acactcagct ggagttccga atactctgaa atgcaacagt tatcgacctc caactcttca   2880
gatactgaaa gcaacaggtg caaactcagc tctggcttgc tccccaagct ggctatttcg   2940
acagatgggg aacaagatga ggctgtccct tgctctggag accccagaga ggagccagag   3000
```

```
aaacctgtcc ctccctctga ggagtgtact caggaggagc ccgaggtcac caccccagcc      3060
agcaccatca gcagttccac actgtcagtt ggcagttttt cagagcactt ggatcagata      3120
aatgggcgaa gcgagtgtgt ggacagtaca gataattcct caaagccatc cagtgaaccc      3180
acttctcacg tggctcgaca gcgcttagaa agcacagaga aaaagaaaat ttctgggaaa      3240
gtcacaaagt ccctctcggc cagtgctctg tccctcatga tcccaggaga tatgttcgct      3300
gtatctccat tgggaagccc aatgtcccca cactccctgt cttcagaccc ttcttcttca      3360
cgggattcct ctcccagccg agactcttct gcagcatctg ccagtccgca tcagcccatt      3420
gtcatccaca gctcaggcaa gaactatggg ttcaccatcc gtgctatccg cgtgtacgtg      3480
ggggacagtg acatctacac agtgcaccat atcgtctgga acgtagaaga aggaagtccc      3540
gcataccagg caggactgaa ggccggggat ctgatcacac acatcaacgg agagccggtg      3600
cacggcctcg tccacacgga agttatcgag ctcctgctga agagtgggaa taaggtgtct      3660
atcaccacta ctccatttga aaacacatca atcaaaacgg gaccagccag gagaaacagt      3720
tacaagggcc ggatggtgag acgaagcaag aagtccaaga agaaggagag tctagaaagg      3780
aggagatctc tcttcaagaa gctggccaag cagccttctc ctttgctcca caccagccga      3840
agtttctcct gcttaaaccg gtccctgtca tctggagaga gcctcccggg ttccccaact      3900
cacagcttgt ccccgaggtc tccaacaccc agttatcgtt ctactcccga ttttccgtca      3960
ggtacaaatt cctcccagag cagctcccca agttcaagtg cccccaattc tccagcaggt      4020
tcagggcaca tccggcccag cacctccat ggcctggctc ccaaactcag cgggcagcga      4080
taccgctctg gaagacggaa gtcggctggc agcatccctc tctccccgct ggccaggaca      4140
ccctctccca ctccacagcc tacctctcct cagcgttcac catccccact gttgggacac      4200
tcactgggca atgccaagat cactcaggcc tttcctagca agatgcactc tcccccccaca      4260 atcgtcagac acatcgtgag gcccaagagt gcagagccgc ccgctcccc actgctgaaa      4320 cgggtgcagt cggaggaaaa gttgtcaccc tcctatggca gtgacaagaa gcttctgtgc      4380
tcccgcaagc atagcctaga ggtgacacaa gaggaggtac agagggagca gtgtcagcgg      4440
gaagtgacac tgcagagcct ggaagagaat gtgtgtgacg ctccttccct cagtcgggcc      4500
aggccagtgg agcaaggctg tctgaaacgc cccgtgtccc ggaaggtggg caggcaagag      4560
tctgtggatg acctggaccg ggacaagctg aaagccaagg ttgtcgtaaa gaaaccagaa      4620
gagaaacatg aatcgcacca gaaacctcac agccttggtg gtgattcgga aagctatgct      4680
ctcttcaggc tagaggagag agagaaaaaa gtgtactcca aggggttgga aaggtcaggc      4740
cattttgaaa acacatcagc agagttgcct tctgtgggca gcctgctgaa ggacactctt      4800
cacaagcagg ccagcgtgag ggccagcgag ggggtgacct cagacggggc agcttgcagc      4860
ctgacaccag gggagcacag ccagtctcta ggtgacttta gcgggcctc agcttctggc      4920 attctccatg atagtgtgtg ccccatctct gataggcctg ctcctggaaa ggttgaatac      4980
tcggagaagg cctctcaggc caaagagctc cttcgaagtg aaaaactaga cagcaagctg      5040
gccaatattg attacctcag aaagaaaatg tcattggatg acaaagatga cagccactgt      5100
gccatcctga aacccaagat aacatctagc gcccatgaat gtctgccagg aacccccata      5160
cggcccatgg cagggcaaca agagacccccg ccagcctctg aaaaccgggc attcatcaac      5220
agtacccaca cacctcagat gagtgcagtt tcctttgttc ctctcaaagc cttagctggc      5280
cgggtagaga acgaggggga gaaagcaggc ttagctgctc ccgagtcccc tgtcaggaag      5340
agcccctccg agtataagct agagggcagg tcagtttcat gtctcaagcc gatcgagggc      5400
```

```
acactggaca ttgctctcct gtctggacct cacgcctcca aaacagagtt gctttcccca    5460
gagcctgcac agagtcccag cccaggcatc aacgtgggac catgtgtgcc actagctctt    5520
cctgggagca gtgggaaaaa gggagactcc accagcctga gagagccttc ctcagccaac    5580
ttaaaagtaa ataaatctta tctgctggag cctcggttcc tacccccgag ccgggctctc    5640
caggactctc tcgcagcctc tgggccagaa ccgaagtcaa agccggaaag gaagctcatt    5700
catccttctg ccaggagccc agcaactgtc acagagagca atcttcagca gaaagagggt    5760
ggtcccgcca cacaccaaga ccgctccact gacaccagga acctccctgg cccagggcag    5820
accctacaca atgtggacct acccaggctg tgtacacgtg ccccactccc accggaaggg    5880
acgcccgcaa aggagaagcc atgtctgaag gaaccctctg ccaaggtgaa aagcgagtgg    5940
tctgccgtga gggatgacgg acacagagat ccctgtgcga agctgtgccc ggcagagact    6000
ggtaaagcca gcgacagttc caaacccctg ccttccgggg ggaggaccca acccgatttc    6060
tacaagcaga cccagacttc ggagaaagca tgggcgcatg caaaaacaaa ccacaaagat    6120
agccaagatg aggtgaagtc cctggccagg gaggactcag cttcactttt atatgaaaag    6180
gagataggcc gggcacgaaa aggtcctgaa cccaaaccgg aagttcctgc tacccggtgc    6240
cctcctcagc caccaggaat tgagggtgag aagcgagaaa agctctccgc tgcccccctct    6300
ttgcagaaac aggctcccaa agagccagac aggaaggaac agacttcgca aaggcctgga    6360
ggtagtggcc ctcaacaacc cccacccacc aaagagctgt ctaactcagc atcctggcag    6420
cacggcagtt ctccgagtca cactttaaag aaggagcccg ggaccaaagc tgccgctgca    6480
gaaccaagca ccagccttca tgacactccc cgatctgcta cagccaccac cactgccatt    6540
gccaccacca ccactaccac cagtgccggg cacagtgact gcagtagcca taaggcccgg    6600
cctggccctg accccagccc ttcaaagtct aagcaccaag acaggtccct ctcctcacag    6660
aagctgagtg ctggctctgc aaaaggcaaa gagcctgtca ctcaacccct gggtggttcc    6720
atcagagaag gcaagggtgg cagcaagggt ccagtggaca cattttctgc tgtcctgacc    6780
acccagggca aagcaagtga tgtgcttgtg cagggagaag gtcgggtctc aatcattgtc    6840
cacactgaag agtgtcctct cgatgccaaa ctgaaaaaca ccaatggagg gtgtcccccca    6900
gagatgcagg cgaagcatcc acccagacaa ggacatctca gtgaagcagc agaccagaag    6960
ccactcattg ctggtgagaa gcaaagcccg tctccaaagc atcccaaacc atccactgtg    7020
aaagattacc ccagtctgtg cagacagaca gacagaagcc caagccatca ggctaccact    7080
ggggacagga aggcagaagg aaagaaatgc acagacgcac tttatgtcgc agccccagag    7140
ggctacaagc cagaggccag cccttctctc caccacggcg agaccggact cagaggctca    7200
gagaggccac ccatgggcat ggggaagggc ttctctgagc ccaaggggaa agggccaggt    7260
ccccagaagt cactggctga aacaggcaag cccagcggta tgaaaaggtc accctctgcc    7320
accgtgcaga gctctctccg ctcagctgcc ccccagaaa gtctctgag ttactcagcc    7380
agctttcccg aggcccagcc tggagtgcga gaggtccctg cagccaacag cagcccctca    7440
tctgccaagg ctacagggg gacctcagag ttcccagccc ccagcagcag ggaccacagg    7500
aagcttcagt ctggaggaga cggccgaagc caaatgataa agagtgactc tctgccctcc    7560
ttccgcctct ccacctctgc tctggagtca catttccagg atccacaggt gccatcgca    7620
tcaggccacc gaggcagggc actgtcagta actgctgcca caggagaacc caaagggaga    7680
gagctcgccc agcctccccc agtcaggaaa cagaatgcgt gcagagaggc gaccagagca    7740
```

```
ccccagccc caagcacaga tcgctccctc cctctttcct cagagaaaga cttcgtggtt      7800
cggcagagaa ggggcaagga gaccttaagg agcagtcctc acaaaaaggc ctcctaa        7857

<210> SEQ ID NO 17
<211> LENGTH: 20
<212> TYPE: DNA
<213> ORGANISM: Mus musculus

<400> SEQUENCE: 17
taccctgccg ctgccgcacc                                                   20

<210> SEQ ID NO 18
<211> LENGTH: 24
<212> TYPE: DNA
<213> ORGANISM: Artificial Sequence
<220> FEATURE:
<223> OTHER INFORMATION: MAST4 exon 1 CRISPR F

<400> SEQUENCE: 18
caccggaaac tctgtcggag gaag                                              24

<210> SEQ ID NO 19
<211> LENGTH: 24
<212> TYPE: DNA
<213> ORGANISM: Artificial Sequence
<220> FEATURE:
<223> OTHER INFORMATION: MAST4 exon 1 CRISPR R

<400> SEQUENCE: 19
aaaccttcct ccgacagagt ttcc                                              24

<210> SEQ ID NO 20
<211> LENGTH: 24
<212> TYPE: DNA
<213> ORGANISM: Artificial Sequence
<220> FEATURE:
<223> OTHER INFORMATION: MAST4 exon 15 CRISPR F

<400> SEQUENCE: 20
caccggcaca aagagtcccg ccag                                              24

<210> SEQ ID NO 21
<211> LENGTH: 24
<212> TYPE: DNA
<213> ORGANISM: Artificial Sequence
<220> FEATURE:
<223> OTHER INFORMATION: MAST4 exon 15 CRISPR R

<400> SEQUENCE: 21
aaacctggcg ggactctttg tgcc                                              24

<210> SEQ ID NO 22
<211> LENGTH: 357
<212> TYPE: DNA
<213> ORGANISM: Mus musculus

<400> SEQUENCE: 22
atgggggaga aagtttccga ggcgcctgag cccgtgcccc ggggctgcag cggacacggc       60
gcccggaccc tagtctcttc ggcggcagcc gtgtcctcgg agggcgcttc ctcagcggag      120
tcatcctctg gctcggaaac tctgtcggag gaagggagc ccagccgctt ctcctgcagg      180
tcgcagccgc cgcggccgcc gggcggcgcc ctggaaccc ggctaccgc cgcgtgggct       240
```

```
cccgcgcgcg tggctctgga gcgtggagtc cctaccctgc cgctgccgca cccgggagga      300
gcggtgctgc cggtgcccca ggtcagcagc gcatcccaag aggagcagga tgaagag        357
```

<210> SEQ ID NO 23
<211> LENGTH: 357
<212> TYPE: DNA
<213> ORGANISM: Mus musculus

<400> SEQUENCE: 23

```
atgggggaga aagtttccga ggcgcctgag cccgtgcccc ggggctgcag cggacacggc      60
gcccggaccc tagtctcttc ggcggcagcc gtgtcctcgg agggcgcttc ctcagcggag     120
tcatcctctg gctcggaaac tctgtcggag gaaggggagc ccagccgctt ctcctgcagg     180
tcgcagccgc cgcggccgcc gggcggcgcc ctgggaaccc ggctaccgc cgcgtgggct      240 cccgcgcgcg tggctctgga gcgtggagtc cctaccctgc cgctgccgca cccgggagga     300
gcggtgctgc cggtgcccca ggtcagcagc gcatcccaag aggagcagga tgaagag       357
```

<210> SEQ ID NO 24
<211> LENGTH: 209
<212> TYPE: DNA
<213> ORGANISM: Mus musculus

<400> SEQUENCE: 24

```
ggcagtctac tttgttcggc acaaagagtc ccgccagagg tttgccatga agaagatcaa     60
caagcagaac ctcatccttc ggaaccagat ccagcaggcc ttcgtggagc gagacatcct    120
gactttcgca gagaaccccct tgtggtcag catgtattgc tcctttgaaa cgaggcgtca    180
cttatgcatg gtcatggagt atgtagaag                                      209
```

<210> SEQ ID NO 25
<211> LENGTH: 209
<212> TYPE: DNA
<213> ORGANISM: Mus musculus

<400> SEQUENCE: 25

```
ggcagtctac tttgttcggc acaaagagtc ccgccagagg tttgccatga agaagatcaa     60
caagcagaac ctcatccttc ggaaccagat ccagcaggcc ttcgtggagc gagacatcct    120
gactttcgca gagaaccccct tgtggtcag catgtattgc tcctttgaaa cgaggcgtca    180
cttatgcatg gtcatggagt atgtagaag                                      209
```

<210> SEQ ID NO 26
<211> LENGTH: 20
<212> TYPE: DNA
<213> ORGANISM: Artificial Sequence
<220> FEATURE:
<223> OTHER INFORMATION: Acan Forward

<400> SEQUENCE: 26

```
ggtcactgtt accgccactt                                                 20
```

<210> SEQ ID NO 27
<211> LENGTH: 20
<212> TYPE: DNA
<213> ORGANISM: Artificial Sequence
<220> FEATURE:
<223> OTHER INFORMATION: Acan Reverse

<400> SEQUENCE: 27

```
ccagggagct gatctcgtag                                                 20
```

```
<210> SEQ ID NO 28
<211> LENGTH: 20
<212> TYPE: DNA
<213> ORGANISM: Artificial Sequence
<220> FEATURE:
<223> OTHER INFORMATION: Chad Forward

<400> SEQUENCE: 28
gccaaggacc tgcgctggct                                               20

<210> SEQ ID NO 29
<211> LENGTH: 20
<212> TYPE: DNA
<213> ORGANISM: Artificial Sequence
<220> FEATURE:
<223> OTHER INFORMATION: Chad Reverse

<400> SEQUENCE: 29
gctttcttgg acctcttggt                                               20

<210> SEQ ID NO 30
<211> LENGTH: 20
<212> TYPE: DNA
<213> ORGANISM: Artificial Sequence
<220> FEATURE:
<223> OTHER INFORMATION: Col2a1 Forward

<400> SEQUENCE: 30
gccaagacct gaaactctgc                                               20

<210> SEQ ID NO 31
<211> LENGTH: 20
<212> TYPE: DNA
<213> ORGANISM: Artificial Sequence
<220> FEATURE:
<223> OTHER INFORMATION: Col2a1 Reverse

<400> SEQUENCE: 31
cttgccccac ttaccagtgt                                               20

<210> SEQ ID NO 32
<211> LENGTH: 20
<212> TYPE: DNA
<213> ORGANISM: Artificial Sequence
<220> FEATURE:
<223> OTHER INFORMATION: Col9a1 Forward

<400> SEQUENCE: 32
cgtggatttc caggccgtgg                                               20

<210> SEQ ID NO 33
<211> LENGTH: 20
<212> TYPE: DNA
<213> ORGANISM: Artificial Sequence
<220> FEATURE:
<223> OTHER INFORMATION: Col9a1 Reverse

<400> SEQUENCE: 33
tcgctgtcct tgatcaccag                                               20

<210> SEQ ID NO 34
<211> LENGTH: 20
<212> TYPE: DNA
<213> ORGANISM: Artificial Sequence
<220> FEATURE:
<223> OTHER INFORMATION: Col11a1 Forward
```

```
<400> SEQUENCE: 34
gctaggtgtt cctggtctgc                                              20

<210> SEQ ID NO 35
<211> LENGTH: 20
<212> TYPE: DNA
<213> ORGANISM: Artificial Sequence
<220> FEATURE:
<223> OTHER INFORMATION: Col11a1 Reverse

<400> SEQUENCE: 35
ccactttctc cagctgttcc                                              20

<210> SEQ ID NO 36
<211> LENGTH: 20
<212> TYPE: DNA
<213> ORGANISM: Artificial Sequence
<220> FEATURE:
<223> OTHER INFORMATION: Comp Forward

<400> SEQUENCE: 36
aacggctcgc actgcaccga                                              20

<210> SEQ ID NO 37
<211> LENGTH: 20
<212> TYPE: DNA
<213> ORGANISM: Artificial Sequence
<220> FEATURE:
<223> OTHER INFORMATION: Comp Reverse

<400> SEQUENCE: 37
cccgttgccg gcccagccaa                                              20

<210> SEQ ID NO 38
<211> LENGTH: 20
<212> TYPE: DNA
<213> ORGANISM: Artificial Sequence
<220> FEATURE:
<223> OTHER INFORMATION: Fmod Forward

<400> SEQUENCE: 38
ccagcagtcc acctactacg                                              20

<210> SEQ ID NO 39
<211> LENGTH: 20
<212> TYPE: DNA
<213> ORGANISM: Artificial Sequence
<220> FEATURE:
<223> OTHER INFORMATION: Fmod Reverse

<400> SEQUENCE: 39
tgcctcagct tggagaagac                                              20

<210> SEQ ID NO 40
<211> LENGTH: 20
<212> TYPE: DNA
<213> ORGANISM: Artificial Sequence
<220> FEATURE:
<223> OTHER INFORMATION: Lect1 Forward

<400> SEQUENCE: 40
gttttgctgg aggagagaag                                              20
```

```
<210> SEQ ID NO 41
<211> LENGTH: 20
<212> TYPE: DNA
<213> ORGANISM: Artificial Sequence
<220> FEATURE:
<223> OTHER INFORMATION: Lect1 Reverse

<400> SEQUENCE: 41
cagtgggtgt agctccgcct                                             20

<210> SEQ ID NO 42
<211> LENGTH: 20
<212> TYPE: DNA
<213> ORGANISM: Artificial Sequence
<220> FEATURE:
<223> OTHER INFORMATION: Matn1 Forward

<400> SEQUENCE: 42
ggcaagacct gcaatgtctg                                             20

<210> SEQ ID NO 43
<211> LENGTH: 20
<212> TYPE: DNA
<213> ORGANISM: Artificial Sequence
<220> FEATURE:
<223> OTHER INFORMATION: Matn1 Reverse

<400> SEQUENCE: 43
tagtcctggc tccggccatc                                             20

<210> SEQ ID NO 44
<211> LENGTH: 20
<212> TYPE: DNA
<213> ORGANISM: Artificial Sequence
<220> FEATURE:
<223> OTHER INFORMATION: Matn3 Forward

<400> SEQUENCE: 44
caggaccagg tgaatgaggt                                             20

<210> SEQ ID NO 45
<211> LENGTH: 20
<212> TYPE: DNA
<213> ORGANISM: Artificial Sequence
<220> FEATURE:
<223> OTHER INFORMATION: Matn3 Reverse

<400> SEQUENCE: 45
atctgcattc agagtgtagc                                             20

<210> SEQ ID NO 46
<211> LENGTH: 20
<212> TYPE: DNA
<213> ORGANISM: Artificial Sequence
<220> FEATURE:
<223> OTHER INFORMATION: Matn4 Forward

<400> SEQUENCE: 46
agctcccgca gcgtgcgccc                                             20

<210> SEQ ID NO 47
<211> LENGTH: 20
<212> TYPE: DNA
<213> ORGANISM: Artificial Sequence
<220> FEATURE:
<223> OTHER INFORMATION: Matn4 Reverse
```

<400> SEQUENCE: 47
atgccgcggg cgcgcgcctg                                                    20

<210> SEQ ID NO 48
<211> LENGTH: 20
<212> TYPE: DNA
<213> ORGANISM: Artificial Sequence
<220> FEATURE:
<223> OTHER INFORMATION: Susd5 Forward

<400> SEQUENCE: 48
tctcagaatg gctctcaggg                                                    20

<210> SEQ ID NO 49
<211> LENGTH: 20
<212> TYPE: DNA
<213> ORGANISM: Artificial Sequence
<220> FEATURE:
<223> OTHER INFORMATION: Susd5 Reverse

<400> SEQUENCE: 49
taccactccc cacagctgtt                                                    20

<210> SEQ ID NO 50
<211> LENGTH: 20
<212> TYPE: DNA
<213> ORGANISM: Artificial Sequence
<220> FEATURE:
<223> OTHER INFORMATION: Ucma Forward

<400> SEQUENCE: 50
ggtcaacagc tccaggaaag                                                    20

<210> SEQ ID NO 51
<211> LENGTH: 20
<212> TYPE: DNA
<213> ORGANISM: Artificial Sequence
<220> FEATURE:
<223> OTHER INFORMATION: Ucma Reverse

<400> SEQUENCE: 51
tttctggtgg ctaagcaagg                                                    20

<210> SEQ ID NO 52
<211> LENGTH: 20
<212> TYPE: DNA
<213> ORGANISM: Artificial Sequence
<220> FEATURE:
<223> OTHER INFORMATION: Mmp8 Forward

<400> SEQUENCE: 52
tgatggaccc aatggaatcc                                                    20

<210> SEQ ID NO 53
<211> LENGTH: 20
<212> TYPE: DNA
<213> ORGANISM: Artificial Sequence
<220> FEATURE:
<223> OTHER INFORMATION: Mmp8 Reverse

<400> SEQUENCE: 53
ggggtcacag gctttgggtg                                                    20

```
<210> SEQ ID NO 54
<211> LENGTH: 20
<212> TYPE: DNA
<213> ORGANISM: Artificial Sequence
<220> FEATURE:
<223> OTHER INFORMATION: Mmp9 Forward

<400> SEQUENCE: 54
gacgggtatc ccttcgacgg                                        20

<210> SEQ ID NO 55
<211> LENGTH: 20
<212> TYPE: DNA
<213> ORGANISM: Artificial Sequence
<220> FEATURE:
<223> OTHER INFORMATION: Mmp9 Reverse

<400> SEQUENCE: 55
gtggtggcgc accagcggta                                        20

<210> SEQ ID NO 56
<211> LENGTH: 22
<212> TYPE: DNA
<213> ORGANISM: Artificial Sequence
<220> FEATURE:
<223> OTHER INFORMATION: Gapdh Forward

<400> SEQUENCE: 56
tggcaaagtg gagattgttg cc                                     22

<210> SEQ ID NO 57
<211> LENGTH: 21
<212> TYPE: DNA
<213> ORGANISM: Artificial Sequence
<220> FEATURE:
<223> OTHER INFORMATION: Gapdh Reverse

<400> SEQUENCE: 57
aagatggtga tgggcttccc g                                      21

<210> SEQ ID NO 58
<211> LENGTH: 20
<212> TYPE: DNA
<213> ORGANISM: Artificial Sequence
<220> FEATURE:
<223> OTHER INFORMATION: Hapln1 Forward

<400> SEQUENCE: 58
gggctggact ggtgcaatgc                                        20

<210> SEQ ID NO 59
<211> LENGTH: 20
<212> TYPE: DNA
<213> ORGANISM: Artificial Sequence
<220> FEATURE:
<223> OTHER INFORMATION: Hapln1 Reverse

<400> SEQUENCE: 59
gcaaatatct ggcccacttt                                        20

<210> SEQ ID NO 60
<211> LENGTH: 20
<212> TYPE: DNA
<213> ORGANISM: Artificial Sequence
<220> FEATURE:
<223> OTHER INFORMATION: Hapln3 Forward
```

```
<400> SEQUENCE: 60
tcctttgggg actaccaagg                                              20

<210> SEQ ID NO 61
<211> LENGTH: 20
<212> TYPE: DNA
<213> ORGANISM: Artificial Sequence
<220> FEATURE:
<223> OTHER INFORMATION: Hapln3 Reverse

<400> SEQUENCE: 61
cacccgcccc ttgagggcag                                              20

<210> SEQ ID NO 62
<211> LENGTH: 20
<212> TYPE: DNA
<213> ORGANISM: Artificial Sequence
<220> FEATURE:
<223> OTHER INFORMATION: Prelp Forward

<400> SEQUENCE: 62
gcccacaaca tcctgagaaa                                              20

<210> SEQ ID NO 63
<211> LENGTH: 20
<212> TYPE: DNA
<213> ORGANISM: Artificial Sequence
<220> FEATURE:
<223> OTHER INFORMATION: Prelp Reverse

<400> SEQUENCE: 63
aagcacatca tgaggtccag                                              20

<210> SEQ ID NO 64
<211> LENGTH: 20
<212> TYPE: DNA
<213> ORGANISM: Artificial Sequence
<220> FEATURE:
<223> OTHER INFORMATION: Fbln7 Forward

<400> SEQUENCE: 64
actgggaacc gctgtcagca                                              20

<210> SEQ ID NO 65
<211> LENGTH: 20
<212> TYPE: DNA
<213> ORGANISM: Artificial Sequence
<220> FEATURE:
<223> OTHER INFORMATION: Fbln7 Reverse

<400> SEQUENCE: 65
acatcctcac agctcttccc                                              20

<210> SEQ ID NO 66
<211> LENGTH: 20
<212> TYPE: DNA
<213> ORGANISM: Artificial Sequence
<220> FEATURE:
<223> OTHER INFORMATION: Sdc4 Forward

<400> SEQUENCE: 66
aggtcatcga cccccaggac                                              20
```

<210> SEQ ID NO 67
<211> LENGTH: 20
<212> TYPE: DNA
<213> ORGANISM: Artificial Sequence
<220> FEATURE:
<223> OTHER INFORMATION: Sdc4 Reverse

<400> SEQUENCE: 67
aactcattgg tgggggcttt                                              20

<210> SEQ ID NO 68
<211> LENGTH: 20
<212> TYPE: DNA
<213> ORGANISM: Artificial Sequence
<220> FEATURE:
<223> OTHER INFORMATION: Bgn Forward

<400> SEQUENCE: 68
aagatctcca agatccatga                                              20

<210> SEQ ID NO 69
<211> LENGTH: 20
<212> TYPE: DNA
<213> ORGANISM: Artificial Sequence
<220> FEATURE:
<223> OTHER INFORMATION: Bgn Reverse

<400> SEQUENCE: 69
gcctctgaga tgcgcaggta                                              20

<210> SEQ ID NO 70
<211> LENGTH: 25
<212> TYPE: DNA
<213> ORGANISM: Artificial Sequence
<220> FEATURE:
<223> OTHER INFORMATION: mMAST4 CRISPR exon 1 sgRNA F

<400> SEQUENCE: 70
caccgtaccc tgccgctgcc gcacc                                        25

<210> SEQ ID NO 71
<211> LENGTH: 25
<212> TYPE: DNA
<213> ORGANISM: Artificial Sequence
<220> FEATURE:
<223> OTHER INFORMATION: mMAST4 CRISPR exon 1 sgRNA R

<400> SEQUENCE: 71
aaacggtgcg gcagcggcag ggtac                                        25

<210> SEQ ID NO 72
<211> LENGTH: 357
<212> TYPE: DNA
<213> ORGANISM: Mus musculus

<400> SEQUENCE: 72
atgggggaga aagtttccga ggcgcctgag cccgtgcccc ggggctgcag cggacacggc    60
gcccggaccc tagtctcttc ggcggcagcc gtgtcctcgg agggcgcttc ctcagcggag   120
tcatcctctg gctcggaaac tctgtcggag gaaggggagc ccagccgctt ctcctgcagg   180
tcgcagccgc cgcggccgcc gggcggcgcc ctgggaaccc ggctaccgc cgcgtgggct    240 cccgcgcgcg tggctctgga gcgtggagtc cctaccctgc cgctgccgca cccgggagga   300
gcggtgctgc cggtgcccca ggtcagcagc gcatcccaag aggagcagga tgaagag     357

```
<210> SEQ ID NO 73
<211> LENGTH: 38
<212> TYPE: DNA
<213> ORGANISM: Artificial Sequence
<220> FEATURE:
<223> OTHER INFORMATION: hMAST4 CR#1 R

<400> SEQUENCE: 73
taatacgact cactatagga gtgtggtcga ggcaatgc                            38

<210> SEQ ID NO 74
<211> LENGTH: 35
<212> TYPE: DNA
<213> ORGANISM: Artificial Sequence
<220> FEATURE:
<223> OTHER INFORMATION: hMAST4 CR#1 R

<400> SEQUENCE: 74
ttctagctct aaaacgcatt gcctcgacca cactc                               35

<210> SEQ ID NO 75
<211> LENGTH: 38
<212> TYPE: DNA
<213> ORGANISM: Artificial Sequence
<220> FEATURE:
<223> OTHER INFORMATION: hMAST4 CR#2 F

<400> SEQUENCE: 75
taatacgact cactataggt aactcgtctg gtgttggt                            38

<210> SEQ ID NO 76
<211> LENGTH: 35
<212> TYPE: DNA
<213> ORGANISM: Artificial Sequence
<220> FEATURE:
<223> OTHER INFORMATION: hMAST4 CR#2 R

<400> SEQUENCE: 76
ttctagctct aaaacaccaa caccagacga gttac                               35

<210> SEQ ID NO 77
<211> LENGTH: 38
<212> TYPE: DNA
<213> ORGANISM: Artificial Sequence
<220> FEATURE:
<223> OTHER INFORMATION: hMAST4 CR#3 F

<400> SEQUENCE: 77
taatacgact cactatagag caaccggaaa agcttaat                            38

<210> SEQ ID NO 78
<211> LENGTH: 35
<212> TYPE: DNA
<213> ORGANISM: Artificial Sequence
<220> FEATURE:
<223> OTHER INFORMATION: hMAST4 CR#3 R

<400> SEQUENCE: 78
ttctagctct aaaacattaa gcttttccgg ttgct                               35

<210> SEQ ID NO 79
<211> LENGTH: 629
<212> TYPE: DNA
<213> ORGANISM: Homo sapiens
```

<400> SEQUENCE: 79

```
ttatcacttg tgtgtatggc atgttacata tttgcactca agcgctggaa gaaggcattt      60
gattattgct ccactggtgg tgaggaatat tgatggtgtt gtgctatatg aatacattat     120
attttctaat attcaagagg tagccacccc tcaaatatta gtgaatgcat aattgtaata     180
attttaacaa taacatgagc agataggttg ctcaacctgg tccatgtcta ccgggaacat     240
ggttgaacat tattgatgct atattctttt taaactttgt ttttctttc ttttgatag      300
ttgccgaaca agcaaccgga aaagcttaat aggcaatggg cagtcaccag cattgcctcg     360
accacactca cctctctctg ctcatgcagg taattggtta ccatttcttg agttttgttt     420
tatttcttta tttgttggtt ttttaaaata attaatgcat tttgatattt ggtatgtctt     480
cacatgttat ctttgttttc ctgctgtttt atccctaagt tgttctttgc gatatgttag     540
cccagatctt atcctctctg tttcagtgtt tggactctaa aatacagaat tccttttat     600
atggggtctc tttttaatta tttctttct                                       629
```

<210> SEQ ID NO 80
<211> LENGTH: 638
<212> TYPE: DNA
<213> ORGANISM: Homo sapiens

<400> SEQUENCE: 80

```
tccagagaga aaactatctt ttgggaaatt ataaacaaat gaggcaaaat atggaaagca      60
ttttgaactc tgagagagaa catcaagtta tacatttagg cagtcgttct tataacttta     120
acatgaaaaa gaaacaataa aaatggtggt attgtccaag tttaactcat cgatctctcc     180
tgttcatttg aagagtttct ttctgaggta gttatgtgac ctcactttgg ttttttcag     240
tcatcctgtt cctcccagga gaagttgcat cagttaccat accaaccaac accagacgag     300
ttacacttct tatcaaaaca tttctgtacc accgaaagca tcgccactga aacagatgc     360
aggaacacgc cgatgcgccc ccgttcccga agtctgaggt gtgtgggcct ggctgaaaac     420
cattacttag ttggattctc tattttcaaa cattttgagt gaacacttcg gtcctttagg     480
tcatatgtgt gttaactgac ttgcaaacta ttacaaatat agtgtgatgt ttccatgtac     540
acataatatt gttaattacc attgaaaggc atcttataag tttccttttc agttctcaca     600
atttgctgat tgcagcagta gtaatcacga tggtcttg                            638
```

<210> SEQ ID NO 81
<211> LENGTH: 629
<212> TYPE: DNA
<213> ORGANISM: Homo sapiens

<400> SEQUENCE: 81

```
ttatcacttg tgtgtatggc atgttacata tttgcactca agcgctggaa gaaggcattt      60
gattattgct ccactggtgg tgaggaatat tgatggtgtt gtgctatatg aatacattat     120
attttctaat attcaagagg tagccacccc tcaaatatta gtgaatgcat aattgtaata     180
attttaacaa taacatgagc agataggttg ctcaacctgg tccatgtcta ccgggaacat     240
ggttgaacat tattgatgct atattctttt taaactttgt ttttctttc ttttgatag      300
ttgccgaaca agcaaccgga aaagcttaat aggcaatggg cagtcaccag cattgcctcg     360
accacactca cctctctctg ctcatgcagg taattggtta ccatttcttg agttttgttt     420
tatttcttta tttgttggtt ttttaaaata attaatgcat tttgatattt ggtatgtctt     480
cacatgttat ctttgttttc ctgctgtttt atccctaagt tgttctttgc gatatgttag     540
```

```
cccagatctt atcctctctg tttcagtgtt tggactctaa aatacagaat tccttttttat    600 atggggtctc tttttaatta tttctttct                                       629
```

<210> SEQ ID NO 82
<211> LENGTH: 20
<212> TYPE: DNA
<213> ORGANISM: Artificial Sequence
<220> FEATURE:
<223> OTHER INFORMATION: HumanAcan RT Forward

<400> SEQUENCE: 82

```
gaatcaactg ctgcagacca                                                  20
```

<210> SEQ ID NO 83
<211> LENGTH: 20
<212> TYPE: DNA
<213> ORGANISM: Artificial Sequence
<220> FEATURE:
<223> OTHER INFORMATION: HumanAcan RT Reverse

<400> SEQUENCE: 83

```
gtgccagatc atcaccacac                                                  20
```

<210> SEQ ID NO 84
<211> LENGTH: 20
<212> TYPE: DNA
<213> ORGANISM: Artificial Sequence
<220> FEATURE:
<223> OTHER INFORMATION: HumanCol9a1 RT Forward

<400> SEQUENCE: 84

```
cgtggatttc caggccgtgg                                                  20
```

<210> SEQ ID NO 85
<211> LENGTH: 20
<212> TYPE: DNA
<213> ORGANISM: Artificial Sequence
<220> FEATURE:
<223> OTHER INFORMATION: HumanCol9a1 RT Reverse

<400> SEQUENCE: 85

```
tcgctgtcct tgatcaccag                                                  20
```

<210> SEQ ID NO 86
<211> LENGTH: 22
<212> TYPE: DNA
<213> ORGANISM: Artificial Sequence
<220> FEATURE:
<223> OTHER INFORMATION: HumanGapdh RT Forward

<400> SEQUENCE: 86

```
tggcaaagtg gagattgttg cc                                               22
```

<210> SEQ ID NO 87
<211> LENGTH: 21
<212> TYPE: DNA
<213> ORGANISM: Artificial Sequence
<220> FEATURE:
<223> OTHER INFORMATION: HumanGapdh RT Reverse

<400> SEQUENCE: 87

```
aagatggtga tgggcttccc g                                                21
```

```
<210> SEQ ID NO 88
<211> LENGTH: 23
<212> TYPE: DNA
<213> ORGANISM: Artificial Sequence
<220> FEATURE:
<223> OTHER INFORMATION: MAST4 Exon 1 targeting sequence

<400> SEQUENCE: 88
ggaaactctg tcggaggaag ggg                                        23

<210> SEQ ID NO 89
<211> LENGTH: 23
<212> TYPE: DNA
<213> ORGANISM: Artificial Sequence
<220> FEATURE:
<223> OTHER INFORMATION: MAST4 Exon 15 targetting sequence

<400> SEQUENCE: 89
ggcacaaaga gtcccgccag agg                                        23

<210> SEQ ID NO 90
<211> LENGTH: 20
<212> TYPE: DNA
<213> ORGANISM: Artificial Sequence
<220> FEATURE:
<223> OTHER INFORMATION: Primer amplifying Exon 1 (F)

<400> SEQUENCE: 90
ctgtggtcca acctctgtca                                            20

<210> SEQ ID NO 91
<211> LENGTH: 20
<212> TYPE: DNA
<213> ORGANISM: Artificial Sequence
<220> FEATURE:
<223> OTHER INFORMATION: Primer amplifying Exon 1 (R)

<400> SEQUENCE: 91
atcggctcag tgacacttcc                                            20

<210> SEQ ID NO 92
<211> LENGTH: 29
<212> TYPE: DNA
<213> ORGANISM: Mus musculus
<220> FEATURE:
<223> OTHER INFORMATION: MAST4 (w/t)

<400> SEQUENCE: 92
gccgcacccg ggaggagcgg tgctgccgg                                  29

<210> SEQ ID NO 93
<211> LENGTH: 27
<212> TYPE: DNA
<213> ORGANISM: Mus musculus
<220> FEATURE:
<223> OTHER INFORMATION: MAST4 (k/o)

<400> SEQUENCE: 93
gccgcccggg aggagcggtg ctgccgg                                    27
```